United States Patent
Lerner et al.

(10) Patent No.: US 10,975,152 B2
(45) Date of Patent: Apr. 13, 2021

(54) TRKB AGONIST ANTIBODIES AND METHODS FOR TREATING AN OCULAR DEGENERATIVE DISORDER CHARACTERIZED BY DEGENERATION OF RETINAL GANGLION CELLS (RGCS)

(71) Applicants: The Scripps Research Institute, La Jolla, CA (US); Zebra Biologies, Inc., Concord, MA (US)

(72) Inventors: Richard A. Lerner, La Jolla, CA (US); Ronald M. Lindsay, Concord, MA (US); Jia Xie, San Diego, CA (US)

(73) Assignees: The Scripps Research Institute, La Jolla, CA (US); Zebra Biologies, Inc., Concord, MA (US)

( * ) Notice: Subject to any disclaimer, the term of this patent is extended or adjusted under 35 U.S.C. 154(b) by 0 days.

(21) Appl. No.: 16/098,226

(22) PCT Filed: May 2, 2017

(86) PCT No.: PCT/US2017/030570
§ 371 (c)(1),
(2) Date: Nov. 1, 2018

(87) PCT Pub. No.: WO2017/192538
PCT Pub. Date: Nov. 9, 2017

(65) Prior Publication Data
US 2019/0177418 A1   Jun. 13, 2019

Related U.S. Application Data

(60) Provisional application No. 62/331,046, filed on May 3, 2016.

(51) Int. Cl.
| | | |
|---|---|---|
| *C07K 16/00* | (2006.01) | |
| *A61K 38/00* | (2006.01) | |
| *A61K 39/00* | (2006.01) | |
| *G01N 33/53* | (2006.01) | |
| *C07K 16/28* | (2006.01) | |
| *C07K 16/24* | (2006.01) | |
| *A61P 27/06* | (2006.01) | |
| *A61P 27/02* | (2006.01) | |
| *A61P 27/00* | (2006.01) | |
| *A61P 25/02* | (2006.01) | |
| *A61P 25/28* | (2006.01) | |
| *A61K 9/00* | (2006.01) | |
| *C12N 15/85* | (2006.01) | |
| *A61K 39/395* | (2006.01) | |

(52) U.S. Cl.
CPC ........ *C07K 16/2863* (2013.01); *A61K 9/0048* (2013.01); *A61P 25/02* (2018.01); *A61P 25/28* (2018.01); *A61P 27/00* (2018.01); *A61P 27/02* (2018.01); *A61P 27/06* (2018.01); *C07K 16/241* (2013.01); *C07K 16/2878* (2013.01); *C12N 15/85* (2013.01); *A61K 39/395* (2013.01); *A61K 39/39533* (2013.01); *A61K 2039/505* (2013.01); *C07K 2317/21* (2013.01); *C07K 2317/31* (2013.01); *C07K 2317/51* (2013.01); *C07K 2317/515* (2013.01); *C07K 2317/52* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/624* (2013.01); *C07K 2317/70* (2013.01); *C07K 2317/75* (2013.01); *C07K 2317/76* (2013.01)

(58) Field of Classification Search
CPC .............. A61K 2300/00; A61K 38/185; A61K 2039/505; A61K 39/395; A61K 38/177; A61K 35/30; A61K 45/06; A61K 9/0085; C07K 16/2863; C07K 2317/75; C07K 2317/92; C07K 2317/52; C07K 2317/55; C07K 2317/34; C07K 2317/31; C07K 2317/33; C07K 2317/522; C07K 2317/524; C07K 2317/56; C07K 2317/565; C07K 2317/567; C07K 2317/622; C07K 14/705; C07K 14/47; C07K 14/48; C07K 14/71; C07K 14/475; C07K 16/00; C07K 16/18; C07K 16/28; C07K 16/22; C07K 16/2803; G01N 2800/28; G01N 2333/48; G01N 2333/50575; G01N 2333/70575; A61P 25/28; A61P 25/02; C12N 2501/13; C12Y 207/10001
See application file for complete search history.

(56) References Cited

PUBLICATIONS

Rudikoff et al., Proc Natl Acad Sci USA 1982; 79:1979-1983.*
MacCallunn et al., J. Mol. Biol., 1996; 262: 732-745.*
Pascalis et al., The Journal of Immunology, 2002; 169: 3076-3084.*
Casset et al., BBRC, 2003; 307:198-205.*
Vajdos et al., J. Mol. Med., 2002; 320: 415-428.*
Holm et al., Mol. Immunol., 2007; 44: 1075-1084.*

(Continued)

*Primary Examiner* — Chang-Yu Wang
(74) *Attorney, Agent, or Firm* — Hugh Wang; Thomas Fitting

(57) ABSTRACT

The invention provides TrkB agonist antibodies or antigen-binding fragments that specifically enhance TrkB signaling activities. The invention also provides therapeutic methods of using such antibodies for promoting survival and regeneration of retinal ganglion cells, and for treating or preventing subjects suffering from or at risk of developing various neurodegenerative conditions such as glaucoma.

10 Claims, 9 Drawing Sheets
Specification includes a Sequence Listing.

(56) References Cited

PUBLICATIONS

Chen et al., J. Mol. Bio., 1999; 293: 865-881.*
Wu et al.,J. Mol. Biol.,1999; 294: 151-162.*
Burgess et al., J of Cell Bio. 1990, 111:2129-2138.*
Bowie et al., Science, 1990, 247:1306-1310.*
Pawson et al., Science, 2003, 300:445-452.*
Alaoui-Ismaili et al., Cytokine Growth Factor Rev. 2009; 20:501-507.*
Guo et al., PNAS 2004; 101:9205-9210.*

* cited by examiner

TRKB AGONIST ANTIBODIES AND METHODS FOR TREATING AN OCULAR DEGENERATIVE DISORDER CHARACTERIZED BY DEGENERATION OF RETINAL GANGLION CELLS (RGCS)

CROSS-REFERENCE TO RELATED APPLICATIONS

The subject patent application claims the benefit of priority to U.S. Provisional Patent Application No. 62/331,046 (filed May 3, 2016). The full disclosure of the priority application is incorporated herein by reference in its entirety and for all purposes.

BACKGROUND OF THE INVENTION

The Trk family of receptors are important in physiological and disease processes in both neuronal and non-neuronal tissues. Amongst these receptor kinases, TrkB plays a key role in signaling for brain derived neurotrophic factor (BDNF), neurotrophin-3 (NT3) and neurotrophin-4 (NT4), which are indispensable for the differentiation, survival and function of neurons in both the peripheral and central nervous systems. Binding of a neurotrophin to a Trk receptor extracellular domain initiates a signal transduction pathway, which leads to dimerization and autophosphorylation of the receptor. Autophosphorylation of TrkB leads to activation of signaling pathways including mitogen-activated protein kinase (MAPK), phospholipase C-γ and phosphatidylinositol-3 kinase (PI3-K).

Both BDNF and TrkB have been shown to play critical roles in the survival of retinal ganglion cells in the retina. It has been suggested that aberrant TrkB signaling and its compromise contribute to the development of various neuropathies and degenerative conditions such as glaucoma. Glaucoma is the second most common eye disease leading to blindness, affects >60M people worldwide with a US prevalence of approximately 2.3M diagnosed cases. Primarily a "plumbing" problem that leads to elevated intra-ocular pressure (IOP), glaucoma results in damage to retinal ganglion cells (RGCs) and their axons that convey all visual stimuli to the brain. While numerous drugs and devices are approved to lower TOP, as yet no drugs have been developed that prevents, slows or reverses RGC or other retinal neuronal cell atrophy and loss that would stave off blindness that eventually occurs in >10% of glaucoma patients. The ability to specifically modulate TrkB signaling can be critical in various pathological scenarios associated with this pathway.

There is a strong need in the art for means for promoting TrkB and BDNF signaling activities in the treatment of various retinal diseases and disorders, especially neuropathies including glaucoma. For example, current glaucoma treatment options reduce TOP but do not reverse RGC degeneration. The instant invention is directed to addressing these and other needs.

SUMMARY OF THE INVENTION

In one aspect, the invention provides TrkB agonist antibodies or antigen-binding fragments that specifically bind to tropomyosin receptor kinase B (TrkB) with the same binding specificity as that of a second antibody. The second antibody contains heavy chain CDRs 1-3 and light chain CDRs 1-3 sequences that are respectively identical to (1) VSDNSGAWN (SEQ ID NO:65), YRSKWYT (SEQ ID NO:66), VRGYYYAFHI (SEQ ID NO:67), SLRTYY (SEQ ID NO:68), GKN, and SSRDSSRSHHLL (SEQ ID NO:73); (2) GYSFTSYW (SEQ ID NO:46), IYPGDSDT (SEQ ID NO:47), ARQGASSTSYDY (SEQ ID NO:48), QSISSY (SEQ ID NO:49), AAS, and QQANSFPVA (SEQ ID NO:50); (3) GFIFSRYN (SEQ ID NO:51), INTDGSVI (SEQ ID NO:52), VRQMLF (SEQ ID NO:53), SGINVGTYR (SEQ ID NO:54), YKSDSDK (SEQ ID NO:55), and ALWHSSAWV (SEQ ID NO:56); (4) GFIFSRYN (SEQ ID NO:51), INTDGSVI (SEQ ID NO:52), VRQMLF (SEQ ID NO:53), SGINVGAYR (SEQ ID NO:57), YKTDSDK (SEQ ID NO:58), and AIWHSSAWV (SEQ ID NO:56); (5) GFIFSRYN (SEQ ID NO:51), INTDGSVI (SEQ ID NO:52), VRQMLF (SEQ ID NO:53), SGINVGAYR (SEQ ID NO:57), YKSDSDK (SEQ ID NO:55), AIWHSSAWV (SEQ ID NO:56); (6) GFIFSRYN (SEQ ID NO:51), INTDGSVI (SEQ ID NO:52), VRQMLF (SEQ ID NO:53), SGINVGTYR (SEQ ID NO:54), YKSDSDK (SEQ ID NO:55), and AIWHSSACV (SEQ ID NO:59); (7) GFIFSRYN (SEQ ID NO:51), INTDGSVI (SEQ ID NO:52), ARQLLY (SEQ ID NO:60), SGINVGAYR (SEQ ID NO:57), YKSDSDK (SEQ ID NO:61), AIWHSSAWV (SEQ ID NO:56); (8) GYSFTSYW (SEQ ID NO:46), IYPGDSDT (SEQ ID NO:47), ATRVLPAGHF (SEQ ID NO:62), NIGDKF (SEQ ID NO:63), YDS, and QVWDNSSNQGV (SEQ ID NO:64); (9) VSDNSGAWN (SEQ ID NO:65), YRSKWYT (SEQ ID NO:66), VRGYYYAFHI (SEQ ID NO:67), SLRTYY (SEQ ID NO:68), GKN, and NSRDGSGNNVV (SEQ ID NO:69); or (10) GYTFTSYA (SEQ ID NO:70), INNTGNP (SEQ ID NO:71), ASRLAAAGFDY (SEQ ID NO:72), SGINVGTYR (SEQ ID NO:54), YKSDSDK (SEQ ID NO:55), and AIWHSSAWV (SEQ ID NO:56).

Some antibodies or antigen-binding fragments of the invention harbor a heavy chain variable region sequence and a light chain variable region sequence, one or both of which are identical to a heavy chain variable region sequence and a light chain variable region sequence respectively shown in (1) SEQ ID NO:38 and SEQ ID NO:39; (2) SEQ ID NO:14 and SEQ ID NO: 15; (3) SEQ ID NO:16 and SEQ ID NO:17; (4) SEQ ID NO:18 and SEQ ID NO: 19; (5) SEQ ID NO:20 and SEQ ID NO:21; (6) SEQ ID NO:22 and SEQ ID NO:23; (7) SEQ ID NO:24 and SEQ ID NO:25; (8) SEQ ID NO:26 and SEQ ID NO:27; (9) SEQ ID NO:28 and SEQ ID NO:29; (10) SEQ ID NO:30 and SEQ ID NO:31; (11) SEQ ID NO:32 and SEQ ID NO:33; (12) SEQ ID NO:34 and SEQ ID NO:35; or (13) SEQ ID NO:36 and SEQ ID NO:37. Some antibodies or antigen-binding fragments contain a heavy chain variable region sequence and a light chain variable region sequence respectively shown in (1) SEQ ID NO:38 and SEQ ID NO:39; (2) SEQ ID NO:14 and SEQ ID NO: 15; (3) SEQ ID NO:16 and SEQ ID NO: 17; (4) SEQ ID NO:18 and SEQ ID NO:19; (5) SEQ ID NO:20 and SEQ ID NO:21; (6) SEQ ID NO:22 and SEQ ID NO:23; (7) SEQ ID NO:24 and SEQ ID NO:25; (8) SEQ ID NO:26 and SEQ ID NO:27; (9) SEQ ID NO:28 and SEQ ID NO:29; (10) SEQ ID NO:30 and SEQ ID NO:31; (11) SEQ ID NO:32 and SEQ ID NO:33; (12) SEQ ID NO:34 and SEQ ID NO:35; or (13) SEQ ID NO:36 and SEQ ID NO:37.

Some antibodies or antigen-binding fragments of the invention contain heavy chain CDRs 1-3 and light chain CDRs 1-3 sequences that are substantially identical, respectively, to (1) VSDNSGAWN (SEQ ID NO:65), YRSKWYT (SEQ ID NO:66), VRGYYYAFHI (SEQ ID NO:67), SLRTYY (SEQ ID NO:68), GKN, and SSRDSSRSHHLL (SEQ ID NO:73); (2) GYSFTSYW (SEQ ID NO:46), IYPGDSDT (SEQ ID NO:47), ARQGASSTSYDY (SEQ ID NO:48), QSISSY (SEQ ID NO:49), AAS, and QQANSFPVA (SEQ ID NO:50); (3) GFIFSRYN (SEQ ID NO:51), INTDGSVI (SEQ ID NO:52), VRQMLF (SEQ ID NO:53), SGINVGTYR (SEQ ID NO:54), YKSDSDK (SEQ ID NO:55), and AIWHSSAWV (SEQ ID NO:56); (4) GFIFSRYN (SEQ ID NO:51), INTDGSVI (SEQ ID NO:52), VRQMLF (SEQ ID NO:53), SGINVGAYR (SEQ ID NO:57), YKTDSDK (SEQ ID NO:58), and AIWHSSAWV (SEQ ID NO:56); (5) GFIFSRYN (SEQ ID NO:51), INTDGSVI (SEQ ID NO:52), VRQMLF (SEQ ID NO:53), SGINVGAYR (SEQ ID NO:57), YKSDSDK (SEQ ID NO:55), AIWHISSAWV (SEQ ID NO:56); (6) GFIFSRYN (SEQ ID NO:51), INTDGSVI (SEQ ID NO:52), VRQMLF (SEQ ID NO:53), SGINVGTYR (SEQ ID NO:54), YKSDSDK (SEQ ID NO:55), and AIWHSSACV (SEQ ID NO:59); (7) GFIFSRYN (SEQ ID NO:51), INTDGSVI (SEQ ID NO:52), ARQLLY (SEQ ID NO:60), SGINVGAYR (SEQ ID NO:57), YKSDSDK (SEQ ID NO:61), AIWHSSAWV (SEQ ID NO:56); (8) GYSFTSYW (SEQ ID NO:46), IYPGDSDT (SEQ ID NO:47), ATRVLPAGHF (SEQ ID NO:62), NIGDKF (SEQ ID NO:63), YDS, and QVWDNSSNQGV (SEQ ID NO:64); (9) VSDNSGAWN (SEQ ID NO:65), YRSKWYT (SEQ ID NO:66), VRGYYYAFHI (SEQ ID NO:67), SLRTYY (SEQ ID NO:68), GKN, and NSRDGSGNNVV (SEQ ID NO:69); or (10) GYTFTSYA (SEQ ID NO:70), INTNTGNP (SEQ ID NO:71), ASRLAAAGFDY (SEQ ID NO:72), SGINVGOTYR (SEQ ID NO:54), YKSDSDK (SEQ ID NO:55), and AIWHSSAWV (SEQ ID NO:56). Some antibodies or antigen-binding fragments harbor a heavy chain CDR sequence selected from the group consisting of SEQ ID NOs:46-48, 51-53, 60, 62, 65-67, and 70-72. Some of these molecules further contain a light chain CDR sequence selected from the group consisting of SEQ ID NOs:49, 50, 54-59, 61, 63, 64, 68, 69 and 73. Some of these molecules contain heavy chain CDRs 1-3 sequences that are respectively identical to (1) SEQ ID Nos:70-72, (2) SEQ ID NOs:46-48, (3) SEQ ID NOs:51-53, (4) SEQ ID Nos:51, 52, 60, (5) SEQ ID Nos:46, 47, and 62, or (6) SEQ ID Nos:65-67. Some of these antibodies or antigen-binding fragments harbor heavy chain CDRs 1-3 and light chain CDRs 1-3 sequences respectively shown in (1) SEQ ID Nos:65-68, GKN, and SEQ ID NO:73; (2) SEQ ID NOs:46-49, AAS, and SEQ ID NO:50; (3) SEQ ID NOs:51-56; (4) SEQ ID Nos:51-53, 57, 58, and 56; (5) SEQ ID Nos:51-53, 57, 55, and 56; (6) SEQ ID Nos:51-55 and 59; (7) SEQ ID Nos:51, 52, 60, 57, 61 and 56; (8) SEQ ID Nos:46, 47, 62, 63, YDS and SEQ ID NO:64; (9) SEQ ID Nos:65-68, GKN, and SEQ ID NO:69; or (10) SEQ ID Nos:70-72 and 54-56.

Some antibodies or antigen-binding fragments of the invention contain a light chain CDR sequence selected from the group consisting of SEQ ID NOs:49, 50, 54-59, 61, 63, 64, 68, 69 and 73, and sequences AAS, YDS and GKN. Some of these molecules additionally contain a heavy chain CDR sequence selected from the group consisting of SEQ ID NOs:46-48, 51-53, 60, 62, 65-67, and 70-72. Some of these molecules contain light chain CDRs 1-3 sequences that are respectively identical to (1) SEQ ID NO:68, GKN and SEQ ID NO:73; (2) SEQ ID NO:49, AAS, and SEQ ID NO:50; (3) SEQ ID NOs:54-56; (4) SEQ ID NOs:57, 58 and 56; (5) SEQ ID NOs:57, 55 and 56; (6) SEQ ID NOs:54, 55 and 59; (7) SEQ ID NOs:57, 61 and 56; (8) SEQ ID NO:63, YDS and SEQ ID NO:64; or (9) SEQ ID NO:68, GKN and SEQ ID NO:69.

Some antibodies or antigen-binding fragments of the invention contain a heavy chain variable region that is substantially identical to SEQ ID NO:14, 16, 18, 20, 22, 24, 26, 28, 30, 32, 34, 36 or 38. Some antibodies or antigen-binding fragments are scFv fragments, which contains a linker sequence that connects the heavy chain and light chain variable region sequences. Some exemplary linker sequences are shown in SEQ ID NOs:40-45. Some scFv fragments of the invention contain a sequence as shown in any one of SEQ ID NOs:1-13.

The antibodies or antigen-binding fragments of the invention can be in any antibody structure format, e.g., IgA1, IgA2, IgD, IgE, IgG1, IgG2, IgG3, IgG4, IgM, F(ab)2, Fv, scFv, IgGACH2, F(ab')2, scFv2CH3, Fab, VL, VH, scFv4, scFv3, scFv2, dsFv, Fv, scFv-Fc, (scFv)2, a non-depleting IgG, a diabody, and a bivalent antibody. The molecules can also be conjugated to a synthetic molecule. In some embodiments, the invention provides bispecific compounds (e.g., bispecific antibodies) that contain a TrkB agonist antibody or antigen-binding fragment described herein.

In another aspect, the invention provides polynucleotides that encode the variable region of the heavy chain and/or light chain of an antibody or antigen-binding fragment of the invention, as well as vectors that harbor such polynucleotides. In another aspect, the invention provides pharmaceutical compositions or kits that contain a therapeutically effective amount of an antibody or antigen-binding fragment described herein, or a polynucleotide or vector expressing the antibody.

In still another aspect, the invention provides methods for promoting survival, synaptic function or regeneration of retinal ganglion cells, motor neurons or central nervous system (CNS) neurons in a subject. Also provided are methods for treating or preventing an ocular degenerative condition, a motor neuron disease or a central nervous system (CNS) degenerative disease in a subject. These therapeutic methods of the invention entail administering to the subject a pharmaceutical composition that contains a therapeutically effective amount of a TrkB agonist antibody or antigen-binding fragment, or a polynucleotide or expression vector encoding the antibody as described herein. In various embodiments, the pharmaceutical composition can be administered to one or both eyes of the subject. Typically, the administered pharmaceutical composition further contains a pharmaceutically acceptable carrier. The subjects suitable for the methods can be one who suffers from or is at risk of developing an ocular degenerative disorder, a motor neuron disease or a central nervous system (CNS) degenerative disease. The ocular degenerative disorder suitable for the methods of the invention can be, e.g., glaucoma, optic nerve injury, optic neuritis, optic neuropathy, central retinal artery occlusion, central retinal vein occlusion, diabetic neuropathy, age-related macular degeneration (AMD), anterior ischemic ocular neuropathy (AION), or diabetic retinopathy. Examples of motor neuron diseases suitable for treatment with methods of the invention include, e.g., ALS, idiopathic motor neuropathy, hereditary spastic paraplegia (HSP), primary lateral sclerosis (PLS), progressive muscular atrophy (PMA), progressive bulbar palsy (PBP) and pseudobulbar palsy, Bell's palsy, or spinal muscular atrophies (SMA). Examples of CNS degenerative diseases that can be treated with methods of the invention include, e.g., Alzheimer's Disease, Parkinson's Disease, or Huntington's Disease.

A further understanding of the nature and advantages of the present invention may be realized by reference to the remaining portions of the specification and claims.

DETAILED DESCRIPTION

I. Overview

Figure 1:
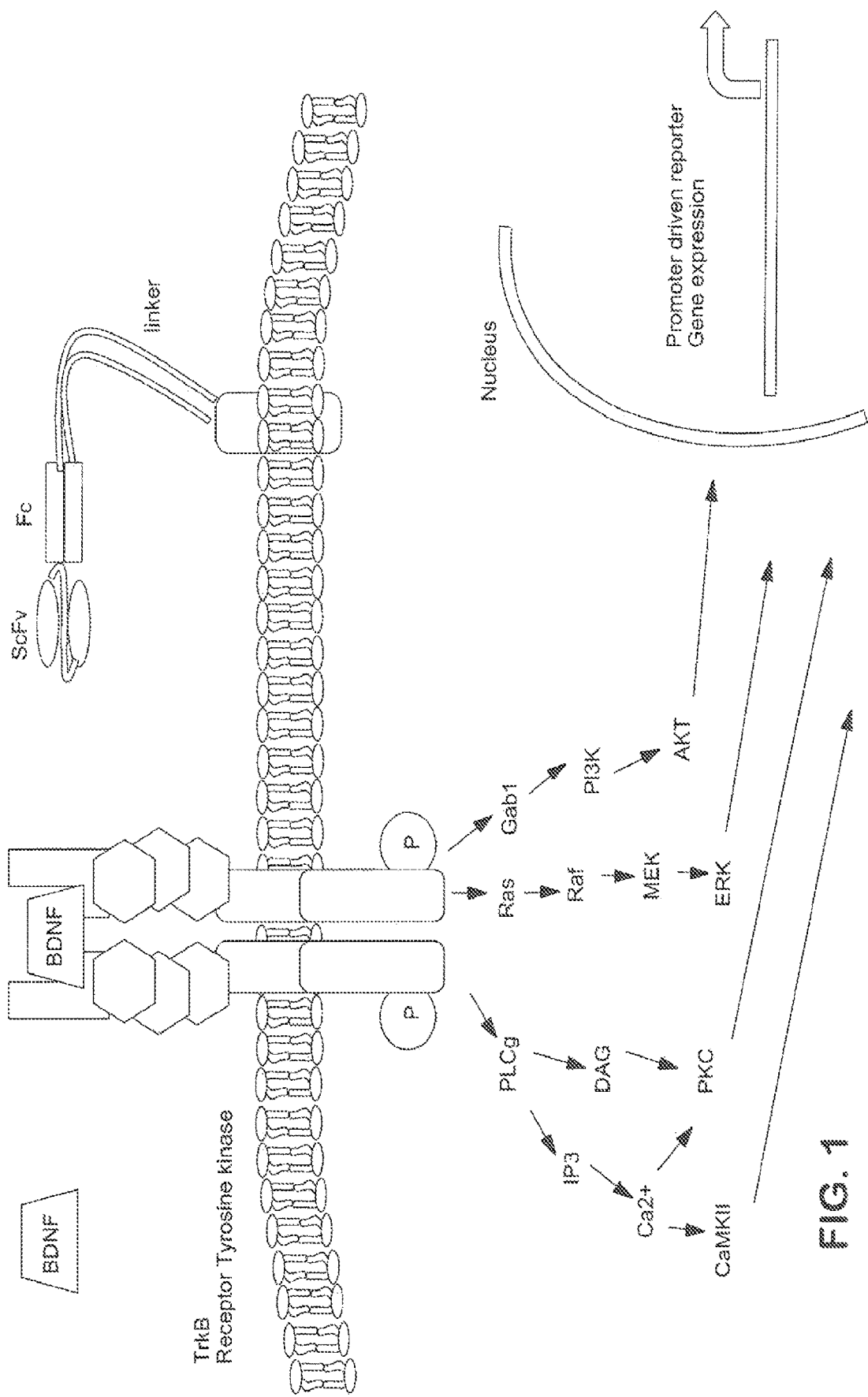
FIG. 1 illustrates the scheme for the construction of a human TrkB reporter for selecting TrkB agonist Abs.

The invention is predicated in part on the development by the present inventors of TrkB activating Antibodies which demonstrated utilities in neuroprotective and neuroregenerative treatment of retinal disorders such as glaucoma. Neuroprotection and neuroregeneration activities of BDNF were evidenced herein by that BDNF greatly slows RGC dendritic retraction, and that BDNF can reverse RGC dendritic degeneration. Importantly, the inventors demonstrated that the TrkB agonist antibodies of the invention showed equal or better properties than BDNF as a neuroprotectant for RGCs.

As detailed herein, the inventors have generated a family of fully human agonist antibodies by selecting rare activating agonist antibodies from combinatorial libraries. In exemplified studies, the TrkB agonist antibodies were shown to be able to mimic the efficacy of BDNF in maintaining or regenerating the dendritic arbor of RGCs that rapidly retracts in axotomized adult mammalian retina. Specifically, relative to BDNF, the antibodies were shown to be potent and selective in both TrkB cell lines and BDNF responsive primary neuronal cultures. The antibodies were also found to be equivalent to BDNF in activating TrkB signal transduction, and also have cross-species activity (e.g., human and mouse). In situ, the antibodies were found to be active in slowing and restoring RGC degeneration in an adult mouse retinal explant assay. Furthermore, assessed via a rat model of hypertensive glaucoma, the TrkB agonist Abs showed a regenerative effect on dendritic arbors of retinal ganglion neurons.

Compared to BDNF, the TrkB agonist antibodies of the invention also have greatly improved biophysical properties (e.g., unlike BDNF these antibodies are not "sticky" proteins) and have much longer half-lives (e.g., better pharmacokldnetics) in human subjects than BDNF itself. In addition, all currently approved treatments for glaucoma are focused on reducing intraocular pressure (IOP) in the anterior chamber of the eye. However, these treatments alone are insufficient to halt the progression of the disease. In contrast, the disease-modifying neuroprotective activities of the TrkB agonist antibodies disclosed herein can reduce RGC dendritic and cell body atrophy or loss and thus slow disease progression. The neuroregenerative activities of the antibodies can also restore the functional integrity of impaired RGCs.

In accordance with these studies, the present invention provides monoclonal antibodies and related antigen-binding fragments that specifically activate the TrkB tyrosine kinase receptor and promote survival or regeneration of RGCs. Also provided in the invention are methods of using these antibody agents in therapeutic applications for treating various neurodegenerative diseases including retinal degenerative disorders that are associated with RGC death or degeneration, or ocular diseases that are mediated by abnormal or impaired TrkB signaling activities, e.g., glaucoma.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4$^{th}$ ed., 2000). In addition, the following definitions are provided to assist the reader in the practice of the invention.

The term "antibody" or "antigen-binding fragment" refers to polypeptide chain(s) which exhibit a strong monovalent, bivalent or polyvalent binding to a given antigen, epitope or epitopes. Unless otherwise noted, antibodies or antigen-binding fragments used in the invention can have sequences derived from any vertebrate species, including camelid, avian or pisces species. They can be generated using any suitable technology, e.g., hybridoma technology, ribosome display, phage display, gene shuffling libraries, semi-synthetic or fully synthetic libraries or combinations thereof. Unless otherwise noted, the term "antibody" as used in the present invention includes intact antibodies, antigen-binding polypeptide fragments and other designer antibodies that are described below or well known in the art (see, e.g., Serafini, J Nucl. Med. 34:533-6, 1993).

An intact "antibody" typically comprises at least two heavy (H) chains (about 50-70 kD) and two light (L) chains (about 25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Each heavy chain of an antibody is comprised of a heavy chain variable region ($V_H$) and a heavy chain constant region. The heavy chain constant region is comprised of three domains, $C_{H1}$, $C_{H2}$ and $C_{H3}$. Each light chain is comprised of a light chain variable region ($V_L$) and a light chain constant region. The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system and the first component (Clq) of the classical complement system.

The $V_H$ and $V_L$ regions of an antibody can be further subdivided into regions of hypervariability, also termed complementarity determining regions (CDRs), which are interspersed with the more conserved framework regions (FRs). Each $V_H$ and $V_L$ is composed of three CDRs and four FRs, arranged from amino-terminus to carboxyl-terminus in the following order. FR1, CDR1, FR2, CDR2, FR3, CDR3, FR4. The locations of CDR and FR regions and a numbering system have been defined by, e.g., Kabat et al., *Sequences of Proteins of Immunological Interest*, U.S. Department of Health and Human Services, U.S. Government Printing Office (1987 and 1991).

Binding affinity is generally expressed in terms of equilibrium association or dissociation constants ($K_a$ or $K_d$, respectively), which are in turn reciprocal ratios of dissociation and association rate constants ($k_{off}$ and $k_{on}$, respectively). Thus, equivalent affinities may correspond to different rate constants, so long as the ratio of the rate constants remains the same.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "contacting" has its normal meaning and refers to combining two or more agents (e.g., polypeptides or phage), combining agents and cells, or combining two populations of different cells. Contacting can occur in vitro, e.g., mixing an antibody and a cell or mixing a population of antibodies with a population of cells in a test tube or growth medium. Contacting can also occur in a cell or in situ, e.g., contacting two polypeptides in a cell by coexpression in the cell of recombinant polynucleotides encoding the two polypeptides, or in a cell lysate. Contacting can also occur in vivo inside a subject, e.g., by administering an agent to a subject for delivery the agent to a target cell.

The term "epitope" refers to any antigenic determinant on an antigen to which the paratope of an antibody binds, and is made up of one or more segments of amino acids. An epitope can be a linear or conformational epitope, and can be continuous or discontinuous. Typically, linear epitopes are continuous, i.e., made up of one continuous stretch of amino acids. Conformational epitopes can be discontinuous i.e., made up of two or more discontinuous segments of amino acids that come together to form an epitope when the antigen is folded. Methods for determining whether antibodies binds to the same epitope are known in the art. Epitopes can be defined or mapped by standard methods well known in art. For example, epitopes can be mapped using assays, such as ELISA assays, utilizing peptide libraries or site-directed mutagenesis of the antigen (such as alanine-scanning of the antigen).

As used herein, "binds to the same epitope" with reference to two or more antibodies means that the antibodies compete for binding to an antigen and bind to the same, overlapping or encompassing continuous or discontinuous segments of amino acids. Those of skill in the art understand that the phrase "binds to the same epitope" does not necessarily mean that the antibodies bind to exactly the same amino acids. The precise amino acids to which the antibodies bind can differ. For example, a first antibody can bind to a segment of amoni acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

Antibody competition assays can be used to determine whether an antibody "binds to the same epitope" as another antibody. Such assays are well known on the art. Typically, competition of 70% or more, such as 70%, 71%, 72%, 73%, 74%, 75%, 80%, 85%, 90%, 95% or more, of an antibody known to interact with the epitope by a second antibody under conditions in which the second antibody is in excess and the first saturates all sites, is indicative that the antibodies "bind to the same epitope." To assess the level of competition between two antibodies, for example, radioimmunoassays or assays using other labels for the antibodies, such as biotin can be used. For example, an antigen can be incubated with a saturanting amount of a first antibody or antigen-binding fragment thereof conjugated to a labeled compound (e.g., $^3H$, $^{125}I$ or biotin) in the presence the same amount of a second unlabeled antibody. The amount of labeled antibody that is bound to the antigen in the presence of the unlabeled blocking antibody is then assessed and compared to binding in the absence of the unlabeled blocking antibody. Competition is determined by the percentage change in binding signals in the presence of the unlabeled blocking antibody compared to the absence of the blocking antibody. Thus, if there is a 70% inhibition of binding of the labeled antibody in the presence of the blocking antibody compared to binding in the absence of the blocking antibody, then there is competition between the two antibodies of 70%. Thus, reference to competition between a first and second antibody of 70% or more, such as 70%, 71%, 72%, 73%, 74%, 75%, 80%, 85%, 90%, 95% or more, means that the first antibody inhibits binding of the second antibody (or vice versa) to the antigen by 70%, 71%, 72%, 73%, 74%, 75%, 80%, 85%, 90%, 95% or more (compared to binding of the antigen by the second antibody in the absence of the first antibody). Thus, inhibition of binding of a first antibody to an antigen by a second antibody of 70%, 71%, 72%, 73%, 74%, 75%, 80%, 85%, 90%, 95% or more indicates that the two antibodies bind to the same epitope. The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, PASTA, and TFASTA in the Wisconsin Genetics Software Package, Genetics Computer Group, Madison, Wis.); or by manual alignment and visual inspection (see, e.g., Brent et al., *Current Protocols in Molecular Biology*, John Wiley & Sons, Inc. (ringbou ed., 2003)). Two examples of algorithms that are suitable for determining percent sequence identity and sequence similarity are the BLAST and BLAST 2.0 algorithms, which are described in Altschul et al, Nuc. Acids Res. 25:3389-3402, 1977; and Altschul et al., J. Mol. Biol. 215:403-410, 1990, respectively.

As used herein, ocular degenerative conditions or disorders refer to eye diseases that are characterized by or associated with degeneration or death of retinal ganglion cells (RGCs), or ocular disorders that are mediated by or associated with impaired TrkB signaling activities. They encompass various clinical presentations and etiologies. Examples of these disorders include glaucoma, optic nerve injury, optic neuritis, optic neuropathies, central retinal artery occlusion, and central retinal vein occlusion.

Glaucoma is an exemplary ocular degenerative condition which is characterized by pathological changes in the optic nerve, visible on the optic disk, and corresponding visual field loss, resulting in blindness if untreated. Glaucoma is associated with increased intraocular pressure, but other factors are involved. Glaucoma includes the more common type of open-angle glaucoma and less common types such as closed-angle glaucoma and normal-tension glaucoma. Current therapies for glaucoma are directed at decreasing intraocular pressure. Medical therapy includes topical ophthalmic drops or oral medications that reduce the production or increase the outflow of intraocular fluid. However, these drug therapies for glaucoma are sometimes associated with significant side effects, such as headache, blurred vision, allergic reactions, death from cardiopulmonary complications and potential interactions with other drugs. Surgical therapies also are used, but they also have numerous disadvantages and modest success rates.

A motor neuron disease (MND) is any of several neurological disorders that selectively affect motor neurons, the cells that control voluntary muscles of the body. They include, e.g., amyotrophic lateral sclerosis (ALS), hereditary spastic paraplegia (HSP), primary lateral sclerosis (PLS), progressive muscular atrophy (PMA), progressive bulbar palsy (PBP) and pseudobulbar palsy. Spinal muscular atrophies are also sometimes included in the group. Motor neuron diseases are neurodegenerative in nature and cause increasing disability and eventually death. The TrkB agonist antibodies disclosed herein can be employed to treat or ameliorate symptoms of any of these disorders, e.g., ALS.

The term "subject" refers to human and non-human animals (especially non-human mammals). The term "subject" is used herein, for example, in connection with therapeutic and diagnostic methods, to refer to human or animal subjects. Animal subjects include, but are not limited to, animal models, such as, mammalian models of conditions or disorders associated with degeneration or death of retinal ganglion cells. Other specific examples of non-human subjects include, e.g, cows, horses, sheep, pigs, cats, dogs, mice, rats, rabbits, guinea pigs, monkeys.

The term "target," "target molecule," or "target cell" refers to a molecule or biological cell of interest that is to be analyzed or detected, e.g., a eukaryotic cell the death of which is to be modulated.

The terms "treat," "treating." "treatment," and "therapeutically effective" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated.

Tropomyosin receptor kinase B (TrkB), also known as Tyrosine receptor kinase B, BDNF/NT-3 growth factors receptor or type 2 neurotrophic receptor tyrosine kinase, is a protein that in humans is encoded by the NTRK2 gene. TrkB is a receptor for brain-derived neurotrophic factor (BDNF). Klein et al., Cell 61: 647-56, 1990; and Squinto et al, Cell 65: 885-93, 1991. TrkB is the high affinity catalytic receptor for several "neurotrophins", which are small protein growth factors that induce the survival and differentiation of distinct cell populations. The neurotrophins that activate TrkB are: BDNF (Brain Derived Neurotrophic Factor), neurotrophin-4 (NT-4), and neurotrophin-3 (NT-3). As such, TrkB mediates the multiple effects of these neurotrophic factors, which includes neuronal differentiation and survival. Research has shown that activation of the TrkB receptor can lead to down regulation of the KCC2 chloride transporter in cells of the CNS.

A "vector" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

III. TrkB Agonist Antibodies and Related Antigen-Binding Molecules

The invention provides antibodies or antigen-binding fragments that specifically bind to TrkB (e.g., human TrkB) and activate the TrkB signaling pathway. Preferably, TrkB agonist antibodies of the invention have the same binding specificity as that of an TrkB agonist antibody exemplified herein (e.g., antibody NFAT-85 or antibody CRE-30 show in Table 1). Thus, the invention encompasses antibodies or antigen-binding fragments with the same binding specificity as that of an antibody having heavy chain CDRs 1-3 and light chain CDRs 1-3 sequences that are respectively identical to (1) VSDNSGAWN (SEQ ID NO:65), YRSKWYT (SEQ ID NO:66), VRGYYYAFHI (SEQ ID NO:67), SLRTYY (SEQ ID NO:68), GKN, and SSRDSSRSHHLL (SEQ ID NO:73); (2) GYSFTSYW (SEQ ID NO:46), IYPGDSDT (SEQ ID NO:47), ARQGASSTSYDY (SEQ ID NO:48), QSISSY (SEQ ID NO:49), AAS, and QQANSFPVA (SEQ ID NO:50); (3) GFIFSRYN (SEQ ID NO:51), INTDGSVI (SEQ ID NO:52), VRQMLF (SEQ ID NO:53), SGINVGTYR (SEQ ID NO:54), YKSDSDK (SEQ ID NO:55), and AIWHSSAWV (SEQ ID NO:56); (4) GFIFSRYN (SEQ ID NO:51), INTDGSVI (SEQ ID NO:52), VRQMLF (SEQ ID NO:53), SGINVGAYR (SEQ ID NO:57), YKTDSDK (SEQ ID NO:58), and AIWHSSAWV (SEQ ID NO:56); (5) GFIFSRYN (SEQ ID NO:51), INTDGSVI (SEQ ID NO:52), VRQMLF (SEQ ID NO:53), SGINVGAYR (SEQ ID NO:57), YKSDSDK (SEQ ID NO:55), AIWHSSAWV (SEQ ID NO:56); (6) GFIFSRYN (SEQ ID NO:51), INTDGSVI (SEQ ID NO:52), VRQMLF (SEQ ID NO:53), SGINVGTYR (SEQ ID NO:54), YKSDSDK (SEQ ID NO:55), and AIWHSSACV (SEQ ID NO:59); (7) GFIFSRYN (SEQ ID NO:51), INTDGSVI (SEQ ID NO:52), ARQLLY (SEQ ID NO:60), SGINVGAYR (SEQ ID NO:57), YKSDSDK (SEQ ID NO:61), AIWHSSAWV (SEQ ID NO:56); (8) GYSFTSYW (SEQ ID NO:46), IYPGDSDT (SEQ ID NO:47), ATRVLPAGHF (SEQ ID NO:62), NIGDKF (SEQ ID NO:63), YDS, and QVWDNSSNQGV (SEQ ID NO:64); (9) VSDNSGAWN (SEQ ID NO:65), YRSKWYT (SEQ ID NO:66), VRGYYYAFHI (SEQ ID NO:67), SLRTYY (SEQ ID NO:68), GKN, and NSRDGSGNNVV (SEQ ID NO:69); or (10) GYTFTSYA (SEQ ID NO:70), INTNTGNP (SEQ ID NO:71), ASRLAAAGFDY (SEQ ID NO:72), SGINVGTYR (SEQ ID NO:54), YKSDSDK (SEQ ID NO:55), and AIWHSSAWV (SEQ ID NO:56).

Some antibodies of the invention can compete with the exemplified antibodies for binding to TrkB. Some antibodies of the invention bind to the same epitope as that recognized by one of the TrkB antibodies exemplified herein. Some antibodies of the invention bind to the same epitope on TrkB with the same or similar affinity as that of one of the TrkB antibodies exemplified herein. Upon binding to TrkB, some antibodies of the invention are capable of modulating one or more of TrkB biological activities or generating cellular responses (e.g., activation of MAPK, phospholipase C-γ and/or PI3-K signaling pathways) in the same or similar manner as that by one of the TrkB antibodies exemplified herein.

Antibodies of the invention include intact antibodies (e.g., IgG1 antibodies), antibody fragments or antigen-binding fragments (e.g., scFv antibodies exemplified herein) which contain the antigen-binding portions of an intact antibody that retain capacity to bind the cognate antigen. A typical intact antibody interacts with target antigen predominantly through amino acid residues that are located in the six heavy and light chain complementarity determining regions (CDR's). The functional TrkB agonist antibodies of the invention encompass antibodies or antigen-binding fragments having at least one of their heavy chain CDR sequences and light chain CDR sequences that is the same as or substantially identical to the corresponding CDR sequence of exemplified TrkB agonist antibodies. In some embodiments, the TrkB agonists of the invention are antibody fragments or antigen-binding molecules that are derived from the exemplified antibodies. Examples of such antibody fragments include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an intact antibody; (v) disulfide stabilized Fvs (dsFvs) which have an interchain disulfide bond engineered between structurally conserved framework regions; (vi) a single domain antibody (dAb) which consists of a $V_H$ or $V_L$ domain (see, e.g., Ward et al., Nature 341:544-546, 1989); and (vii) an isolated complementarity determining region (CDR) as a linear or cyclic peptide.

Antibodies of the invention also encompass single chain antibodies. The term "single chain antibody" refers to a polypeptide comprising a $V_H$ domain and a $V_L$ domain in polypeptide linkage, generally linked via a spacer peptide or linker sequence, and which may comprise additional domains or amino acid sequences at the amino- and/or carboxyl-termini. For example, a single-chain antibody may comprise a tether segment for linking to the encoding polynucleotide. As an example, a single chain variable region fragment (scFv) is a single-chain antibody. Compared to the $V_L$ and $V_H$ domains of the Fv fragment which are coded for by separate genes, a scFv has the two domains joined (e.g., via recombinant methods) by a synthetic linker. This enables them to be made as a single protein chain in which the $V_L$ and $V_H$ regions pair to form monovalent molecules. Some scFv TrkB agonist antibodies of the invention are shown in listed in Table 1. The $V_L$ and $V_H$ sequences, as well as the connecting linker sequence, of these scFV antibodies are indicated in Table 2.

As exemplified herein, the scFv TrkB agonist antibodies can be fused to the Fc domain of an IgG to provide scFv-Fc fusion molecules. Fusion with an Fc-domain provides a number of beneficial biological and pharmacological properties. For example, the presence of the Fc domain can markedly increase the plasma half-life of the hybrid molecule, which prolongs therapeutic activity, owing to its interaction with the salvage neonatal Fc-receptor, as well as to the slower renal clearance for larger sized molecules. Further, addition of the Fc region also can improve the solubility and stability of the fused partner, and allows for easy cost-effective purification by protein-G/A affinity chromatography during manufacture. Hybrid or fusion molecules containing an scFv antibody fragment and a fusion partner such as Fc domain can be readily generated in accordance with standard recombination techniques, routinely practiced protein synthesis methods or the protocols described herein.

Antibodies of the present invention also encompass single domain antigen-binding units which have a camelid scaffold. Animals in the camelid family include camels, llamas, and alpacas. Camelids produce functional antibodies devoid of light chains. The heavy chain variable ($V_H$) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies.

In addition to the TrkB agonist antibodies exemplified herein which were initially identified via functional screening, various other antibodies or antigen-binding fragments of the invention can also be produced by enzymatic or chemical modification of the intact antibodies, or synthesized de novo using recombinant DNA methodologies, or identified using phage display libraries. As exemplification, the specific scFv antibodies shown in Table 1 can be readily converted into scFv-Fc fusions via standard recombinant techniques, e.g., by cloning into a pFUSE IgG backbone vector described herein. Additional methods that may be employed for generating the other TrkB agonist antibodies or antigen-binding molecules of the invention are all well known in the art. For example, single chain antibodies can be identified using phage display libraries or ribosome display libraries, gene shuffled libraries (see, e.g., McCafferty et al., Nature 348:552-554, 1990; and U.S. Pat. No. 4,946,778). In particular, scFv antibodies can be obtained using methods described in, e.g., Bird et al., Science 242: 423-426, 1988; and Huston et al., Proc. Natl. Acad. Sci. USA 85:5879-5883, 1988. Fv antibody fragments can be generated as described in Skerra and Plückthun, Science 240:1038-41, 1988. Disulfide-stabilized Fv fragments (dsFvs) can be made using methods described in, e.g., Reiter et al., Int. J. Cancer 67:113-23, 1996. Similarly, single domain antibodies (dAbs) can be produced by a variety of methods described in, e.g., Ward et al., Nature 341:544-546, 1989; and Cai and Garen, Proc. Natl. Acad. Sci. USA 93:6280-85, 1996. Camelid single domain antibodies can be produced using methods well known in the art, e.g., Dumoulin et al., Nat. Struct. Biol. 11:500-515, 2002; Ghahromudi et al., FEBS Letters 414:521-526, 1997; and Bond et al., J. Mol. Biol. 332:643-55, 2003. Other types of antigen-binding fragments (e.g., Fab, F(ab')2 or Fd fragments) can also be readily produced with routinely practiced immunology methods. See, e.g., Harlow & Lane, *Using Antibodies, A Laboratory Manual*, Cold Spring Harbor Laboratory Press, Cold Spring Harbor, N.Y., 1998.

In some embodiments, the antibodies or antigen binding fragments of the invention have its heavy chain CDR1, CDR2 and CDR3 sequences and/or its light chain CDR1, CDR2 and CDR3 sequences that are substantially identical to that of the antibodies shown in Table 1. The light chain and heavy chain CDR sequences of the exemplified antibodies are all indicated in Table 2. In some of these embodiments, the antibodies or antigen-binding fragments have heavy chain CDR1-3 sequences and light chain CDR1-3 sequences that are substantially identical to (1) SEQ ID NOs:46-49, AAS, and SEQ ID NO:50; (2) SEQ ID NOs:51-56; (3) SEQ ID NOs:51-53, 57, 58, and 56; (4) SEQ ID NOs:51-53, 57, 55, and 56; (5) SEQ ID NOs:51-55 and 59; (6) SEQ ID NOs:51, 52, 60, 57, 61 and 56; (7) SEQ ID NOs:46, 47, 62, 63, YDS and SEQ ID NO:64; (8) SEQ ID NOs:65-68, GKN, and SEQ ID NO:69; (9) SEQ ID NOs:70-72 and 54-56; or (10) SEQ ID NOs:65-68, GKN, and SEQ ID NO:73. In some of these embodiments, the percentage of sequence identity can be at least 91%, at least 92%, at least 93%, at least 94%, at least 95%, at least 96%, at least 97%, at least 98%, or at least 99%, or even 100%. Thus, some antibodies or antigen binding fragments of the invention have heavy chain CDRs 1-3 and/or light chain CDRs 1-3 sequences that are at least 90% identical, respectively, to the corresponding CDRs of one of the exemplified antibodies. Some of these antibodies contain heavy chain CDR sequences and/or light chain CDR sequences that are at least 95% identical, respectively, to the corresponding CDRs of the exemplified antibody. In some other antibodies or antigen binding fragments of the invention, the heavy chain CDR sequences and/or light chain CDR sequences are at least 95% identical, respectively, to the corresponding CDRs of one of the exemplified antibodies. In some embodiments, the heavy chain CDR1-CDR3 and light chain CDR1-CDR3 sequences of the antibody are respectively identical to the sequences shown in (1) SEQ ID NOs:46-49, AAS, and SEQ ID NO:50; (2) SEQ ID NOs:51-56; (3) SEQ ID NOs:51-53, 57, 58, and 56; (4) SEQ ID NOs:51-53, 57, 55, and 56; (5) SEQ ID NOs:51-55 and 59; (6) SEQ ID NOs:51, 52, 60, 57, 61 and 56; (7) SEQ ID NOs:46, 47, 62, 63, YDS and SEQ ID NO:64; (8) SEQ ID NOs:65-68, GKN, and SEQ ID NO:69; (9) SEQ ID NOs:70-72 and 54-56; or (10) SEQ ID NOs:65-68, GKN, and SEQ ID NO:73.

In other embodiments, the antibodies or antigen-binding fragments that specifically bind to human TrkB contain (a) a heavy chain variable region that is substantially identical to SEQ ID NO:14, 16, 18, 20, 22, 24, 26, 28, 30, 32, 34, 36 or 38, (b) a light chain variable region that is substantially identical to SEQ ID NO: 15, 17, 19, 21, 23, 25, 27, 29, 31, 33, 35, 37 or 39, or (c) both a heavy chain variable region of (a) and a light chain variable region of (b). In some embodiments, the antibody comprises both a heavy chain of (a) and a light chain of (b). In some embodiments, the antibody or antigen-binding fragment contains (a) a heavy chain variable domain having at least 90% identity to any one of SEQ ID NOs:14, 16, 18, 20, 22, 24, 26, 28, 30, 32, 34, 36 and 38, (b) a light chain variable domain having at least 90% sequence identity to any one of SEQ ID NOs:15, 17, 19, 21, 23, 25, 27, 29, 31, 33, 35, 37 and 39, or (c) both a heavy chain of (a) and a light chain of (b). In some embodiments, the antibody or antigen-binding fragment contains a light chain variable domain having at least 90% identity to any one of SEQ ID NOs:15, 17, 19, 21, 23, 25, 27, 29, 31, 33, 35, 37 and 39. In some of these embodiments, the percentage of sequence identity can be at least 91%, at least 92%, at least 930%, at least 94%, at least 95%, at least 96%, at least 97%, at least 98%, or at least 99%, or even 100%. In some embodiments, the light chain variable domain has at least 95% identity to any one of SEQ ID NOs:15, 17, 19, 21, 23, 25, 27, 29, 31, 33, 35, 37 and 39. In some embodiments, the light chain variable domain has 100% identity to any one of SEQ ID NOs:15, 17, 19, 21, 23, 25, 27, 29, 31, 33, 35, 37 and 39. In some other embodiments, the antibody or antigen-binding fragment contains a heavy chain variable domain having at least 90% identity to any one of SEQ ID NOs:14, 16, 18, 20, 22, 24, 26, 28, 30, 32, 34, 36 and 38. In other embodiments, the percentage identity can be at least 91%, at least 92%, at least 93%, at least 94%, at least 95%, at least 96%, at least 97%, at least 98%, or at least 99%, or even 100%. In some embodiments, the heavy chain variable domain has at least 95% identity to any one of SEQ ID NOs:14, 16, 18, 20, 22, 24, 26, 28, 30, 32, 34, 36 and 38. In some embodiments, the heavy chain variable domain has 100% identity to any one of SEQ ID NOs:14, 16, 18, 20, 22, 24, 26, 28, 30, 32, 34, 36 and 38.

In addition to a heavy chain as described above, the antibody or antigen-binding fragment of the invention can further comprise a light chain selected from a Fab library using sequential naive chain shuffling. Likewise, in addition to a light chain as described above, the antibody of the invention can further comprise a heavy chain selected from a Fab library using sequential naive chain shuffling. In some embodiments, the antibody or antigen-binding fragment of the invention can contain any heavy chain as described herein (e.g., heavy chains shown in SEQ ID NOs:14, 16, 18, 20, 22, 24, 26, 28, 30, 32, 34, 36 and 38) in combination with any suitable light chain, such as those exemplified herein. Likewise, the antibody can comprise any of the light chains as described above (e.g., light chains shown in 15, 17, 19, 21, 23, 25, 27, 29, 31, 33, 35, 37 and 39) in combination with any suitable heavy chain, such as those exemplified herein. For example, in some preferred embodiments, the antibody contains a heavy chain variable region sequence and a light chain variable region sequence that are at least 90% identical, respectively, to SEQ ID NOs: 14 and 15, SEQ ID NOs:16 and 17, SEQ ID NOs:18 and 19, SEQ ID NOs:20 and 21, SEQ ID NOs:22 and 23, SEQ ID NOs:24 and 25, SEQ ID NOs:26 and 27, SEQ ID NOs:28 and 29, SEQ ID NOs:30 and 31, SEQ ID NOs:32 and 33, SEQ ID NOs:34 and 35, SEQ ID NOs:36 and 37, or SEQ ID NOs:38 and 39. In some embodiments, the antibody can contain the heavy chain and light chain sequences respectively shown in SEQ ID NOs: 14 and 15, SEQ ID NOs:16 and 17, SEQ ID NOs:18 and 19, SEQ ID NOs:20 and 21, SEQ ID NOs:22 and 23, SEQ ID NOs:24 and 25, SEQ ID NOs:26 and 27, SEQ ID NOs:28 and 29, SEQ ID NOs:30 and 31, SEQ ID NOs:32 and 33, SEQ ID NOs:34 and 35, SEQ ID NOs:36 and 37, or SEQ ID NOs:38 and 39. In the various embodiments, percent (%) identity of peptide sequences can be calculated, for example, as 100×[(identical positions)/min (TGA, TOB)], where TGA and TGB are the sum of the number of residues and internal gap positions in peptide sequences A and B in the alignment that minimizes TGA and TGB. See, e.g., Russell et al, J. Mol. Biol., 244: 332-350 (1994).

The antibody or antigen-binding fragment of the invention can be any antibody including a full length antibody or an antibody fragment that specifically recognizes or binds to the extracellular domain of TrkB (e.g., human TrkB) with the same specificity as one of the TrkB agonist antibodies exemplified herein (Table 1). The TrkB antibodies of the invention are preferably monoclonal. They can be recombinant, chimeric, humanized or fully human antibodies. Furthermore, the antibody can be of any isotype including without limitation IgA, IgD, IgE, IgG, or IgM. Thus, for example, the antibody can be any IgA such as IgA1 or IgA2, or any IgG such as IgG1, IgG2, IgG3, IgG4, or synthetic IgG. The antibody can also be any antibody fragment having specificity for the extracellular domain of human TrkB, such as F(ab)2, Fv, scFv, IgGACH2, F(ab')2, scFv2CH3, Fab, VL, VH, scFv4, scFv3, scFv2, dsFv, Fv, scFv-Fc, (scFv)2, a diabody, and a bivalent antibody. The antibody can be any modified or synthetic antibody, including, but not limited to, non-depleting IgG antibodies, CARs, or other Pc or Fab variants of antibodies.

In some embodiments, the invention provides antibodies or antigen-binding fragments that are conservatively modified variants of the anti-TrkB antibodies exemplified herein. Typically, the variable regions of these variants have an amino acid sequence that is identical to one of these exemplified sequences except for conservative substitutions at one or more amino acid residues. In some embodiments, the antibody or antigen-binding fragment of the invention specifically binds to TrkB and contains (a) at least one HCDR having a sequence selected from the group consisting of SEQ ID NOs:46-48, 51-53, 60, 62, 65-67, and 70-72; and/or (b) at least one LCDR having a sequence selected from the group consisting of SEQ ID NOs:49, 50, 54-59, 61, 63, 64, 68, 69 and 73, and sequences AAS, YDS and GKN. The invention also provides TrkB agonist antibodies that specifically bind to TrkB and contain one or more variants of the foregoing CDR sequences or substantially identically CDR sequences. The variant CDR sequences in these antibodies can include 1, 2, or 3 substitutions, insertions, deletions, or combinations thereof in a sequence selected from the group consisting of SEQ ID NOs:46-73 and sequences AAS, YDS and GKN. For example, a recombinant chimeric or humanized antibody (or fragment thereof) can include one, two, three, four, five, or six of the foregoing CDR sequences.

In some embodiments, the TrkB agonist antibodies or antigen-binding fragments of the invention include three CDR sequences of the same light or heavy chain of the antibodies in Table 1. These include, e.g., light chain CDRs shown in (1) SEQ ID NO:49, AAS, and SEQ ID NO:50, (2) SEQ ID NOs:54-56, (3) SEQ ID NOs:57, 58 and 56, (4) SEQ ID NOs:57, 55 and 56, (5) SEQ ID NOs:54, 55 and 59, (6) SEQ ID NOs:57, 61 and 56, (7) SEQ ID NO:63, YDS and SEQ ID NO:64, (8) SEQ ID NO:68, GKN and SEQ ID NO:69, and (9) SEQ ID NO:68, GKN and SEQ ID NO:73; or heavy chain CDRs shown in (1) SEQ ID NOs:46-48, (2) SEQ ID NOs:51-53, (3) SEQ ID NOs:51, 52, 60, (4) SEQ ID NOs:46, 47, and 62, (5) SEQ ID NOs:65-67, and (6) SEQ ID NOs:70-72. In some embodiments, the TrkB agonist antibodies or antigen-binding fragments of the invention can contain six CDR sequences of the same antibody, e.g., (1) SEQ ID NOs:46-49, AAS, and SEQ ID NO:50 (antibody CRE-6); (2) SEQ ID NOs:51-56 (antibody CRE-30 or CRE-83); (3) SEQ ID NOs:51-53, 57, 58, and 56 (antibody CRE-31 or CRE-53); (4) SEQ ID NOs:51-53, 57, 55, and 56 (antibody CRE-39 or NFAT-79); (5) SEQ ID NOs:51-55 and 59 (antibody CRE-87); (6) SEQ ID NOs:51, 52, 60, 57, 61 and 56 (antibody CRE-93); (7) SEQ ID NOs:46, 47, 62, 63, YDS and SEQ ID NO:64 (antibody NFAT-27); (8) SEQ ID NOs:65-68, GKN, and SEQ ID NO:69 (antibody NFAT-40); (9) SEQ ID NOs:70-72 and 54-56 (antibody NFAT-44); or (10) SEQ ID NOs:65-68, GKN, and SEQ ID NO:73 (antibody NFAT-85).

In some embodiments, the invention provides antibodies or antigen-binding fragments with avidity for TrkB of about 10 µM or less, 5 µM or less, 2 µM or less, 1 µM or less, 500 nM or less, 400 nM or less, 300 nM or less, or 200 nM or less. In some embodiments, the antibodies or antigen-binding fragments bind to TrkB with an avidity of about 100 nM or less, about 75 nM or less, about 50 nM or less, about 25 nM or less, about 10 nM or less, or about 5 nM or less. In some embodiments, the antibodies or antigen-binding fragments bind to TrkB with an avidity of about 1 nM or less, about 800 pM or less, about 700 pM or less, about 600 pM or less, about 500 pM or less, about 400 pM or less, about 300 pM or less, about 200 pM or less, or about 100 pM or less. Avidity can be measured using art-known techniques, such as ELISA or surface plasmon resonance.

The antibody of the invention can be produced by any suitable technique, for example, using any suitable eukaryotic or non-eukaryotic expression system. In certain embodiments, the antibody is produced using a mammalian expression system. Some specific techniques for generating the antibodies or antigen-binding fragments of the invention are exemplified herein. In some embodiments, the antibodies or antigen-binding fragments of the invention can be produced using a suitable non-eukaryotic expression system such as a bacterial expression system. Bacterial expression systems can be used to produce fragments such as a F(ab)2, Fv, scFv, IgGACH2, F(ab')2, scFv2CH3, Fab, VL, VH, scFv4, scFv3, scFv2, dsFv, Fv, scFv-Fc, (scFv)2, and diabodies. Techniques for altering DNA coding sequences to produce such fragments are known in the art.

The antibodies or antigen-binding fragments of the invention can be conjugated to a synthetic molecule using any type of suitable conjugation. Recombinant engineering and incorporated selenocysteine (e.g., as described in U.S. Pat. No. 8,916,159 issued on Dec. 23, 2014) can be used to conjugate a synthetic molecule. Other methods of conjugation can include covalent coupling to native or engineered lysine side-chain amines or cysteine side-chain thiols. See, e.g., Wu et al., Nat. Biotechnol, 23: 1 137-1 146 (2005). The synthetic molecule can be any molecule such as one targeting a molecule of interest (e.g., a cell surface receptor). In some embodiments, the synthetic molecule for conjugation to the antibody is a protein (e.g., an antibody) or an RNA or DNA aptamer. In some embodiments, a TrkB agonist antibody (e.g., a scFv molecule) of the invention is present as a component in a bispecific molecule or multispecific molecule. Typically, the bispecific or multispecific compounds of the invention contain the TrkB agonist antibody or antigen-binding fragment that is covalently or non-covalently conjugated to at least one other binding moiety that specifically recognizes a target of interest (e.g., TrkC or TNFα). The binding moiety can be a molecule of any chemical nature, e.g., another antibody or antigen binding fragment, a polypeptide or peptide agent, or a small molecule agent. In some embodiments, the multispecific molecules of the invention are bispecific antibodies that contain the TrkB agonist antibody and another antibody or antigen-binding fragment that is well known in the art, e.g., TNFα antibody adalimumab as exemplified herein. IN various embodiments, the other binding moiety in these bispecific or multiple specific molecules can be edrecolomab, capromab, ibritumomab, blinatumomab, abciximab, rituximab, basiliximab, infliximab, cetuximab, brentuximab, siltuximab, palivizumab, trastuzumab, alemtuzumab, omalizumab, bevacizumab, natalizumab, ranibizumab, eculizumab, certolizumab, pertuzumab, obinutuzumab, pembrolizumab, vedolizumab, elotuzumab, idarucizumab, mepolizumab, adalimumab, panitumumab, canakinumab, golimumab, ofatumumab, ustekinumab, denosumab, belimumab, ipilimumab, raxibacumab, nivolumab, ramucirumab, alirocumab, daratumumab, evolocumab, necitumumab, and secukinumab. In some other embodiments, the multispecific molecules of the invention are bispecific small molecule-antibody conjugates. Relative to a monospecific antibody, such bispecific compounds can lead to enhanced drug efficacy and/or desired targeting manipulation.

IV. Polynucleotides, Vectors and Cells for Producing TrkB Antibodies

The invention provides substantially purified polynucleotides (DNA or RNA) that are identical or complementary to sequences encoding polypeptides comprising segments or domains of the antibody chains or antigen-binding molecules described herein. In some embodiments, the polynucleotides of the invention encode the heavy chain and/or light chain domains sequences shown in Table 1. When expressed from appropriate expression vectors, polypeptides encoded by these polynucleotides are capable of exhibiting antigen binding capacity. Also provided in the invention are polynucleotides which encode at least one CDR region and usually all three CDR regions from the heavy or light chain of the antibodies described herein. Some other polynucleotides encode all or substantially all of the variable region sequence of the heavy chain and/or the light chain of the exemplified antibodies. For example, some of these polynucleotides encode the amino acid sequence of the heavy chain variable region shown in any one SEQ ID NO:14, 16, 18, 20, 22, 24, 26, 28, 30, 32, 34, 36 or 38, and/or the amino acid sequence of the light chain variable region shown in anyone SEQ ID NO:15, 17, 19, 21, 23, 25, 27, 29, 31, 33, 35, 37 or 39. Because of the degeneracy of the code, a variety of nucleic acid sequences will encode each of the immunoglobulin amino acid sequences.

The polynucleotides of the invention can encode only the variable region sequence of an exemplified antibody. They can also encode both a variable region and a constant region of the antibody. Some of polynucleotide sequences of the invention nucleic acids encode a mature heavy chain variable region sequence that is substantially identical (e.g., at least 80%, 90%, or 99%) to the mature heavy chain variable region sequence shown in any one SEQ ID NOs: 14, 16, 18, 20, 22, 24, 26, 28, 30, 32, 34, 36 or 38. Some other polynucleotide sequences encode a mature light chain variable region sequence that is substantially identical to the mature light chain variable region sequence shown in any one SEQ ID NOs: 15, 17, 19, 21, 23, 25, 27, 29, 31, 33, 35, 37 or 39. Some of the polynucleotide sequences encode a polypeptide that comprises variable regions of both the heavy chain and the light chain of one of the exemplified antibody. Some other polynucleotides encode two polypeptide segments that respectively are substantially identical to the variable regions of the heavy chain and the light chain of one of the exemplified antibodies.

The polynucleotide sequences can be produced by de novo solid-phase DNA synthesis or by PCR mutagenesis of an existing sequence (e.g., sequences as described in the Examples below) encoding an exemplified functional antibody. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., *PCR Technology: Principles and Applications for DNA Amplification*, H. A. Erlich (Ed.), Freeman Press, NY, N.Y., 1992; *PCR Protocols: A Guide to Methods and Applications*, Innis et al. (Ed.), Academic Press, San Diego, Calif., 1990; Mattila t al., Nucleic Acids Res. 19:967, 1991; and Eckert et al., PCR Methods and Applications 1:17, 1991.

Also provided in the invention are expression vectors and host cells for producing the functional antibodies described herein. Specific examples of lentiviral based vectors for expressing the antibodies are described in the Examples below. Various other expression vectors can also be employed to express the polynucleotides encoding the functional antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat. Genet. 15:345, 1997). For example, nonviral vectors useful for expression of the antibody polynucleotides and polypeptides in mammalian (e.g., human)

cells include pCEP4, pREP4, pThioHis A, B & C, pcDNA3.1/His, pEBVHis A, B & C (Invitrogen, San Diego, Calif.), MPSV vectors, and numerous other vectors known in the art for expressing other proteins. Other useful nonviral vectors include Sleeping Beauty, PiggyBack and other transposon systems. Useful viral vectors include vectors based on lentiviruses or other retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a functional antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a functional antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al, Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted functional antibody sequences. More often, the inserted functional antibody sequences are linked to a signal sequences before inclusion in the vector. Vectors to be used to receive sequences encoding the functional antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the functional antibody chains can be either prokaryotic or eukaryotic. In some preferred embodiments, mammalian host cells are used to express and produce the antibody polypeptides of the present invention. For example, they can be either a hybridoma cell line expressing endogenous immunoglobulin genes or a mammalian cell line harboring an exogenous expression vector. These include any normal mortal or normal or abnormal immortal animal or human cell. In addition to the cell lines exemplified herein, a number of other suitable host cell lines capable of secreting intact immunoglobulins are also known in the art. These include, e.g., the CHO cell lines, various HEK 293 cell lines, various Cos cell lines, HeLa cells, myeloma cell lines, transformed B-cells and hybridomas. The use of mammalian tissue cell culture to express polypeptides is discussed generally in, e.g., Winnacker, *From Genes to Clones*, VCH Publishers, N.Y., N.Y., 1987. Expression vectors for mammalian host cells can include expression control sequences, such as an origin of replication, a promoter, and an enhancer, and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, EF1α and human UbC promoters exemplified herein, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transformation is commonly utilized for prokaryotic cells, whereas calcium phosphate treatment or electroporation may be used for other cellular hosts (see generally Sambrook et al., *Molecular Cloning: A Laboratory Manual*, Cold Spring Harbor Press ($3^{rd}$ ed., 2001)). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate for the cell type.

V. Therapeutic Applications

The TrkB antibodies disclosed herein can be used in various therapeutic applications. Some methods of the invention are directed to induce activation or enhance signaling activities of the TrkB signaling pathway in a TrkB expressing cell, e.g., retinal ganglion cell. These methods can be employed for in vitro or in vivo modification of the cell. In these methods, a therapeutically effective amount of a TrkB agonist of the invention is typically contacted with the cell. Some other methods of the invention are directed to promoting regeneration or survival of retinal ganglion cells in a mammalian subject. For example, these methods can be used for restoring, improving or preserving visual function of the eyes of a subject afflicted with or at risk of developing an ocular degenerative condition. Some other methods of the invention relate to treating or preventing a subject having or at risk of developing an ocular degenerative condition. In these methods, a pharmaceutical composition containing a therapeutically effective amount of a TrkB agonist of the invention is administered to the subject. In addition to pharmaceutical compositions containing a TrkB antibody of the invention, therapeutic applications of the invention can also utilize the polynucleotides or vectors discussed herein that encode and express the antibodies. For example, compositions that harbor the antibody-encoding polynucleotides or vectors of the invention can be employed in gene therapy for various neurodegenerative diseases descried herein.

Many ocular degenerative conditions are suitable for therapeutic or prophylactic treatment with the therapeutic methods of the invention. These include any ocular disease or disorder that is characterized by or associated with degeneration or death of retinal ganglion cells (RGCs). Specific examples of such diseases or conditions include, e.g., glaucoma, optic nerve injury, optic neuritis, optic neuropathies, central retinal artery occlusion, and central retinal vein occlusion. Other ocular disorders that may be amenable for treatment with the therapeutic antibody compositions of the invention include, e.g., diabetic neuropathy, macular degeneration including both the wet and dry forms of age-related macular degeneration (AMD), anterior ischemic ocular neuropathy (AION), ischemic retinopathy, diabetic retinopathy, retinopathy of prematurity, retinitis pigmentosa, and retinal degeneration.

In some embodiments, the invention provides methods for enhancing TrkB signaling activities in cells that express TrkB (e.g., retinal ganglion cells) by contacting the cells with an antibody or antigen-binding fragment of the invention. In some related embodiments, the TrkB agonists of the invention can be used for promoting the survival or regeneration of retinal ganglion cells in a subject. In these embodiments, functional integrity of retinal ganglion cells can be preserved or restored as a result of updated TrkB signaling activities that are elicited by the administered TrkB agonist agents. In various embodiments, the administered TrkB agonist antibody or antigen-binding fragment can be a naked (unconjugated) molecule or an antibody molecule conjugated to a synthetic molecule, e.g., a targeting moiety or another therapeutic agent. The methods can be used to upregulate TrkB signaling in the cells in vitro or in a subject (i.e., in vivo). The contacted TrkB-expressing cells can be present in, for example, a cell culture or animal model of a disorder associated with aberrant or impaired TrkB signaling activation or signaling activities or a disease characterized by degeneration or death of retinal ganglion cells.

In some other embodiments, the invention provides methods for treating a subject that is in need of enhanced TrkB signaling. This includes subjects who have, are suspected to have, or are at risk of developing a disease associated with impaired TrkB signaling activities or a disease that can be treated via enhanced TrkB signaling, e.g, motor neuron diseases such as amyotrophic lateral sclerosis (ALS). In some embodiments, the invention provides methods for promoting survival, regeneration and synaptic function of motor neurons. These methods can be employed for treating subjects afflicted with various motor neuron diseases including ALS, idiopathic motor neuropathies, hereditary spastic paraplegia (HSP), primary lateral sclerosis (PLS), progressive muscular atrophy (PMA), progressive bulbar palsy (PBP) and pseudobulbar palsy, Bells palsy, or spinal muscular atrophies (SMA). In some other embodiments, the invention provides methods for promoting survival, regeneration and synaptic function of central nervous system (CNS) neurons. These methods can be readily employed for treating subjects who are suffering from CNS degenerative diseases. Many CNS degenerative diseases or disorders are suitable for treatment with the therapeutic compositions of the invention. These include, e.g., Alzheimer's Disease, Parkinson's Disease, Huntington's Disease and Tourette's syndrome.

Some therapeutic methods of the invention are specifically directed to treating subjects having or are at risk of developing an ocular disorder characterized by degeneration or death of retinal ganglion cells. These include a number of ocular degenerative conditions, e.g., glaucoma, optic nerve injury, optic neuritis, optic neuropathies, central retinal artery occlusion, central retinal vein occlusion, diabetic neuropathy, macular degeneration including both the wet and dry forms of age-related macular degeneration (AMD), anterior ischemic ocular neuropathy (AION), and diabetic retinopathy.

In generally, the various therapeutic methods described herein involve administering to the subject a pharmaceutical composition that contains a therapeutically effective amount of an isolated or purified TrkB agonist antibody or antigen-binding fragment (or a polynucleotide or vector expressing the antibody) of the invention. The antibody can be any anti-TrkB agonist antibody of the invention as described herein in Table 1 or a derivative therefrom, e.g., an antibody derived from antibody NFAT-85 and/or having the same binding specificity as that of NFAT-85. Thus, the administered antibody can be a synthetic, a chimeric, a humanized, or a fully human antibody or antigen-binding fragment. It can be F(ab)2, Fv, scFv, IgGACH2, F(ab')2, scFv2CH3, Fab, VL, VH, scFv4, scFv3, scFv2, dsFv, Fv, or (scPFv)2. In some embodiments, the method includes administering an IgG, an scFv, a dsFv, a F(ab')2, a diabody, or a bivalent antibody. In some embodiments, the administered antibody or antigen-binding fragment can be conjugated to another therapeutic agent (e.g., a known drug or compound for treating ocular degenerative conditions) or other agents (e.g., a targeting agent).

The TAB agonist antibodies of the invention can be used in combination with other known agents for promoting TrkB signaling and for treating ocular degenerative conditions. Such known TrkB agonist compounds include, e.g., neurotrophic factor BDNF and neurotrophic factor mimetics. Specific examples of known TrkB agonist compounds include, e.g., L-783,281 adenosine, COS 21680, and etc. See, e.g., Pollack et al. Cunr. Drug Targ-CNS and Neurol. Disorders 1:59-80 2002. The TrkB agonist compounds can also be small molecules that mimic critical regions of neurotrophins. For example, the small molecule can be a mimetic of a BDNF β-turn loop. Particular examples of such small molecule mimetics that may be used according to the invention are described in, e.g., U.S. Published Application No. 2007/0060526. Preferably, the TrkB agonist antibodies and the other known TrkB agonist compounds used in the methods of the invention are selective for TrkB and activate TrkB to a greater extent than TrkA or TrkC. In some embodiments, the employed agents are specific for TrkB and do not activate TrkA or TrkC.

In some therapeutic applications, the TrkB agonist antibodies of the invention can be used in combination with other known medications or regiments for treating optic neuropathies or retinal degenerative disorders such as glaucoma. For example, the antibodies can be used together with any of the existing IOP lowering drugs. These known drugs include, e.g., prostaglandin analogues such as Xalatan (latanoprost) and Lumigan (bimatroprost), Beta blockers such as timolol, betaxolol and metipranolol. In addition to therapeutic IOP lowering drugs, there are many approved drainage devices which can be used in combination with antibodies of the invention.

In some embodiments, the TrkB agonist antibody or antigen-binding molecules of the invention can be conjugated to a targeting moiety when employed in the therapeutic methods described herein. The targeting moieties can be a protein or a peptide which directs localization to a certain part of the body, e.g., to the brain or compartments therein. In some embodiments, the TrkB antibody agonists can be attached or fused to a brain targeting moiety. The brain targeting moieties can be attached covalently (e.g., direct, translational fusion, or by chemical linkage either directly or through a spacer molecule, which can be optionally cleavable) or non-covalently attached (e.g., through reversible interactions such as avidin, biotin, protein A, IgG, etc.). A brain targeting moiety conjugated to a TrkB antibody agonist of the invention can enhances brain delivery of the TrkB agonist. A number of agents can be employed as the brain targeting moiety in the practice of the invention. These include polypeptides or antibody fragments which can deliver a fused protein or therapeutic agent through the blood brain barrier (BBB). Examples of such agents include single domain antibody FC5 (Abulrob et al. J. Neurochem. 95, 1201-1214, 2005); mAB 83-14, a monoclonal antibody to the human insulin receptor (Pardridge et al. Pharmacol. Res. 12, 807-816, 1995); the B2, B6 and B8 peptides which bind to the human transferrin receptor (hTfR) (Xia et al. J. Virol. 74, 11359-11366, 2000); the OX26 monoclonal antibody to the transferrin receptor (Pardridge et al. J. Pharmacol. Exp. Ther. 259, 66-70, 1991); and several polypeptides described in U.S. Pat. No. 6,306,365.

VI. Pharmaceutical Compositions and Combinations

The invention provides methods of using a TrkB agonist of the invention in the manufacture of a medicament for treating ocular degenerative disorders such as glaucoma. Subjects in need of treatment or alleviation of such a condition can be administered with a TrkB agonist of the invention alone. However, the administration of a pharmaceutical composition that contains the TrkB agonist and a pharmaceutically acceptable carrier is more preferred. Examples of TrkB agonist of the inventions that can be employed in the pharmaceutical compositions include any of the TrkB agonist antibodies or antigen-binding molecules described herein. Exemplary compositions include one or more of antibodies that have mature heavy chain and light chain variable domain sequences respectively shown in SEQ TD NOs:14 and 15, SEQ ID NOs:16 and 17, SEQ ID NOs:18 and 19, SEQ ID NOs:20 and 21, SEQ ID NOs:22 and 23, SEQ ID NOs:24 and 25, SEQ ID NOs:26 and 27, SEQ ID NOs:28 and 29, SEQ ID NOs:30 and 31, SEQ ID NOs:32 and 33, SEQ ID NOs:34 and 35, SEQ ID NOs:36 and 37, or SEQ ID NOs:38 and 39. In some embodiments, the antibody can contain the heavy chain and light chain sequences respectively shown in SEQ ID NOs:14 and 15, SEQ ID NOs:16 and 17, SEQ ID NOs:18 and 19, SEQ ID NOs:20 and 21, SEQ ID NOs:22 and 23, SEQ ID NOs:24 and 25, SEQ ID NOs:26 and 27, SEQ ID NOs:28 and 29, SEQ ID NOs:30 and 31, SEQ ID NOs:32 and 33, SEQ ID NOs:34 and 35, SEQ ID NOs:36 and 37, or SEQ ID NOs:38 and 39. Other antibodies suitable for the pharmaceutical compositions of the invention include those having a mature chain sequence as shown in SEQ ID NOs:14, 16, 18, 20, 22, 24, 26, 28, 30, 32, 34, 36 or 38 and/or a mature light chain sequence as shown in SEQ ID NOs:15, 17, 19, 21, 23, 25, 27, 29, 31, 33, 35, 37 or 39.

Additional exemplary therapeutic compositions of the invention can contain an antibody having one, two, three, four, five, or six CDRs selected from the group consisting of SEQ ID NOs:46-73 and sequences AAS, YDS and GKN. In some embodiments, however, the antibody includes three CDR sequences of the same exemplified light or heavy chains shown in Table 1. In some embodiments, the pharmaceutical composition includes an antibody having six CDR sequences of the same antibody exemplified in Table 1, e.g., (1) SEQ ID NOs:46-49, AAS, and SEQ ID NO:50 (antibody CRE-6); (2) SEQ ID NOs:51-56 (antibody CRE-30 or CRE-83); (3) SEQ ID NOs:51-53, 57, 58, and 56 (antibody CRE-31 or CRE-53); (4) SEQ ID NOs:51-53, 57, 55, and 56 (antibody CRE-39 or NFAT-79); (5) SEQ ID NOs:51-55 and 59 (antibody CRE-87); (6) SEQ ID NOs:51, 52, 60, 57, 61 and 56 (antibody CRE-93); (7) SEQ ID NOs:46, 47, 62, 63, YDS and SEQ ID NO:64 (antibody NFAT-27); (8) SEQ ID NOs:65-68, GKN, and SEQ ID NO:69 (antibody NFAT-40); (9) SEQ ID NO:70-72 and 54-56 (antibody NFAT-44); or (10) SEQ ID NOs:65-68, GKN, and SEQ ID NO:73 (antibody NFAT-85). Still another exemplary pharmaceutical composition includes a dsFv fragment, which can include one or more modifications to the amino acid sequence as appropriate and understood by one of ordinary skill in the art.

The invention also provides for a pharmaceutical combination, e.g. a kit. Such pharmaceutical combination can contain an active agent which is a TrkB agonist disclosed herein, in free form or in a composition, one or more inactive agents or other components, as well as instructions for administration of the agents. In some embodiments, therapeutic kits of the invention can contain one or more doses of a TrkB agonist (e.g., antibody NFAT-85) present in a pharmaceutical composition described herein, a suitable device for intravitreal injection of the pharmaceutical composition, and an instruction detailing suitable subjects and protocols for carrying out the injection.

The pharmaceutical compositions that comprise a TrkB agonist antibody can be prepared in various forms. Suitable solid or liquid pharmaceutical preparation forms are, e.g., granules, powders, tablets, coated tablets, (micro)capsules, suppositories, syrups, emulsions, suspensions, creams, aerosols, drops or injectable solution in ampule form and also preparations with protracted release of active compounds. The antibody compositions of the invention can also be prepared and administered to subjects in the form of surfactants. The pharmaceutical compositions of the invention can be prepared in accordance with the standard protocols well known in the art, e.g., *Remington: The Science and Practice of Pharmacy*, Gennaro (ed.), Lippincott Williams & Wilkins (20$^{th}$ ed., 2003). The pharmaceutical compositions typically contain an effective amount of the TrkB agonist antibody that is sufficient to lessen or ameliorate symptoms of an ocular degenerative disorder. In addition to the TrkB agonist antibody, the pharmaceutical compositions can also contain certain pharmaceutically acceptable carriers which enhance or stabilize the composition, or facilitate preparation of the composition. For example, the TrkB agonist antibody can be complexed with carrier proteins such as ovalbumin or serum albumin prior to their administration in order to enhance stability or pharmacological properties. The various forms of pharmaceutical compositions can also contain excipients and additives and/or auxiliaries such as disintegrants, binders, coating agents, swelling agents, lubricants, flavorings, sweeteners and elixirs containing inert diluents commonly used in the art, such as purified water.

Pharmaceutically acceptable carriers are determined in part by the particular composition being administered as well as by the particular method used to administer the composition. They should also be both pharmaceutically and physiologically acceptable in the sense of being compatible with the other ingredients and not injurious to the subject. The carrier may take a wide variety of forms depending on the form of preparation desired for administration, e.g., oral, sublingual, rectal, nasal, intravenous, or parenteral. For example, examples of non-aqueous solvents are propylene glycol, polyethylene glycol, vegetable oils such as olive oil, and injectable organic esters such as ethyl oleate. Carriers for occlusive dressings can be used to increase skin permeability and enhance absorption. Liquid dosage forms for oral administration may generally comprise a liposome solution containing the liquid dosage form.

For therapeutic or prophylactic applications, a pharmaceutical composition containing a TrkB agonist antibody can be administered locally or systemically in a therapeutically effective amount or dose. For example, they may be administered parenterally, enterically, by injection, rapid infusion, nasopharyngeal absorption, dermal absorption, and orally. However, in preferred embodiments, local administration of the composition is desired in order to achieve the intended therapeutic effect. In some of these embodiments, the compositions can be administered to the subject in need of treatment via intravitreal injection. This can be performed in accordance with standard procedures known in the art. See, e.g., Russelakis-Carnmeiro et al., Neuropathol. Appl. Neurobiol. 25:196-206, 1999; and Wray et al., Arch. Neurol. 33:183-5, 1976. Other local administration routes that may be used for delivering a pharmaceutical composition of the invention to the eyes of a subject include, e.g., intraocular, intraorbital, subconjuctival, subretinal or transscleral routes. It is contemplated that local modes of administration may reduce or eliminate the incidence of potential side effects (e.g., systemic toxicity) that may occur during systemic administration. In some other embodiments, a pharmaceutical composition of the invention may also be administered to patients systemically, e.g., by oral or parenteral routes. Parenteral routes include, for example, intravenous, intrarterial, intramuscular, intradermal, subcutaneous, intranasal and intraperitoneal routes.

A therapeutically effective amount means an amount that that is sufficient to reduce or inhibit the symptoms of the disorder or condition to be treated in a subject. In the practice of the present invention, the amount of the administered TrkB agonist antibody should be effective for slowing, stopping or reversing ocular degeneration, e.g., degeneration or death of RGCs. Such effective amount will vary from subject to subject depending on the ocular disorder afflicted by the subject, stage and severity of the disorder, the subject's general conditions (such as height, weight, age, and health), the particular compound administered, and other factors. For a given TrkB agonist antibody, one skilled in the art can easily identify the effective amount of the compound by using routinely practiced pharmaceutical methods. Typically, dosages used in vitro may provide useful guidance in the amounts useful for in situ administration of the pharmaceutical composition, and animal models may be used to determine effective dosages for treatment of particular disorders in human subjects. More often, a suitable therapeutic dose can be determined by clinical studies on mammalian species to determine maximum tolerable dose and on normal human subjects to determine safe dosage.

In general, except under certain circumstances when higher dosages may be required, the preferred dosage of a TrkB agonist antibody usually lies within the range of from about 0.001 to about 1000 mg, more usually from about 0.01 to about 500 mg per day. As a general rule, the quantity of a TrkB agonist antibody administered is the smallest dosage which effectively and reliably prevents or minimizes the conditions of the subjects. Also, the dosages to be administered and frequency of administration can vary depending on whether the treatment is prophylactic or therapeutic. In prophylactic applications, a relatively lower dosage may be administered at relatively infrequent intervals over a long period of time. Some subjects may continue to receive treatment for the rest of their lives. In therapeutic applications, a relatively higher dosage at relatively short intervals may be required until progression of the disease is reduced or terminated, and preferably until the subject shows partial or complete amelioration of symptoms of the ocular vascular disease. Thereafter, the subject can be administered a prophylactic regime. As is readily apparent, the above dosage ranges are intended to provide general guidance and support for the teachings herein, but are not intended to limit the scope of the invention. Additional guidance for preparation and administration of the pharmaceutical compositions of the invention has also been described in the art. See, e.g., *Goodman & Gilman's The Pharmacological Bases of Therapeutics*, Hardman et al, eds., McGraw-Hill Professional ($10^{th}$ ed., 2001); *Remington: The Science and Practice of Pharmacy*, Gennaro, ed., Lippincott Williams & Wilkins ($20^{th}$ ed., 2003); and *Pharmaceutical Dosage Forms and Drug Delivery Systems*, Ansel et al. (eds.), Lippincott Williams & Wilkins ($7^{th}$ ed., 1999).

EXAMPLES

The following examples are provided to further illustrate the invention but not to limit its scope. Other variants of the invention will be readily apparent to one of ordinary skill in the art and are encompassed by the appended claims.

Example 1 Development of TrkB Agonist Abs

Cell Lines:

The specific TrkB agonist antibodies exemplified herein were selected and identified via a function-based screen of a combinatorial library of scFv antibodies. Detailed procedures for carrying out the screen are described in Zhang et al., Proc. Natl. Acad. Sci. USA 109:15728-33, 2012; and Zhang at al., Chem. Biol. 20:734-41, 2013. Briefly, a two-stage process was employed. First, a reporter cell line was generated by transfecting human TrkB into CHO cells using a lentiviral vector. Cells were also transfected with a reporter cassette using an NFAT promoter linked to a GFP reporter, such that, upon activation with the cognate ligand, BDNF, a fluorescent signal is generated. Second, a $10^{11}$ scFv phage library was used to pan the etco domain of human TrkB. Positives (hits) from the panning process were cloned into a lentiviral vector and clones were infected into the reporter cell at a multiplicity of infection (MOI) of ~1 (FIG. 1). In a second screen, instead of using NFAT activation as readout, the reporter cassette utilized the CRE promoter linked to the GFP reporter.

Figure 2:
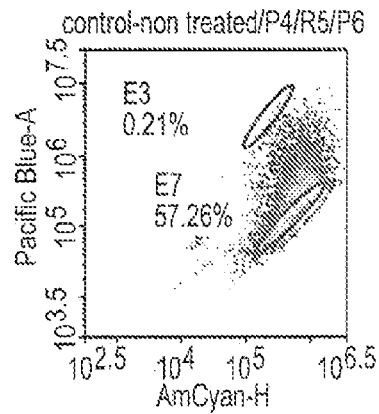
FIG. 2 shows activities of several unpurified scFv-Fc TrkB agonist antibodies in culture supernatant examined via a TrkB reporter cell line.
Figure 2:
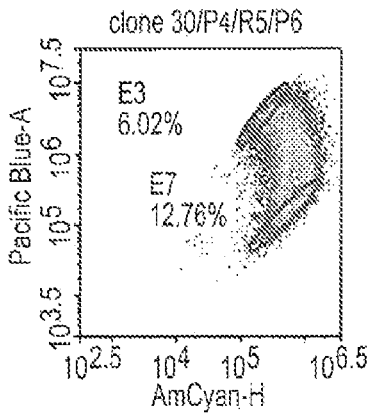
Figure 2:
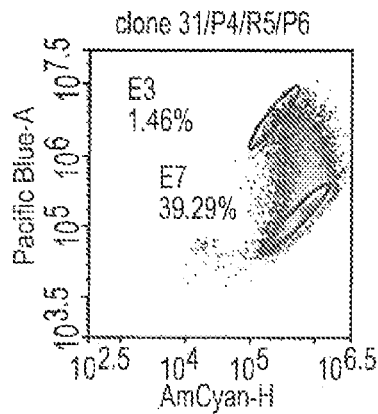
Figure 2:
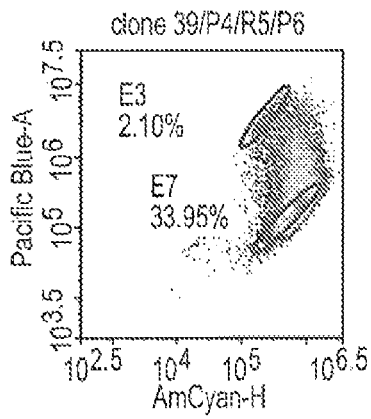
Figure 2:
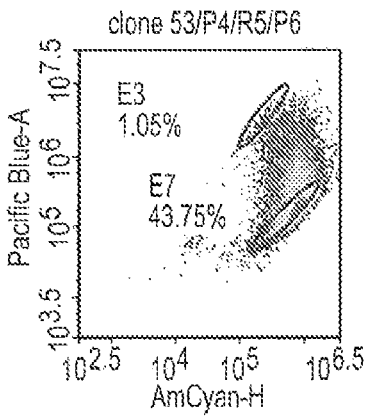
Figure 2:
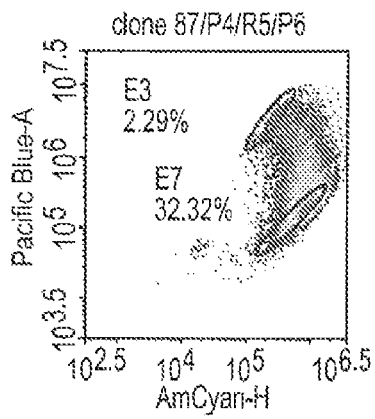

Hits from this functional selection were harvested and three rounds of infection/selection yielded multiple scFv clones upon deep sequencing. The scFv sequences were cloned into a pFUSE IgG backbone (human $IgG_1$) to generate scFv-Fc fusion antibodies. In a preliminary study of the activities of the selected TrkB antibodies, the ScFv-Fc constructs were transfected into HEK293 cells. Following 2 days of culturing, the supernatant of each cultured clone was used to examine the effect on activating a TrkB reporter cell line. Results from the study are shown in FIG. 2. As shown in the figure, the identified TrkB scFv agonist antibodies (e.g., scFv CRE-30) showed varying degree of activities in activating the TrkB reporter cell line.

Figure 3:
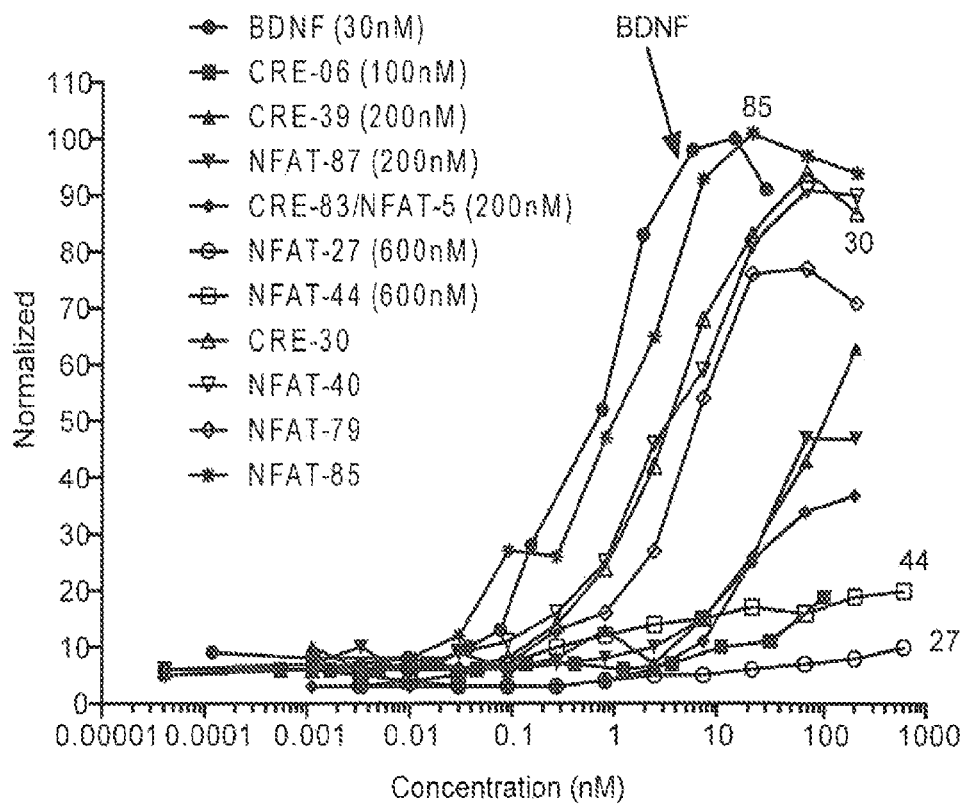
FIG. 3 shows activities of a number of TrkB agonist IgG antibodies in TrkB reporter cell assay.
Figure 4:
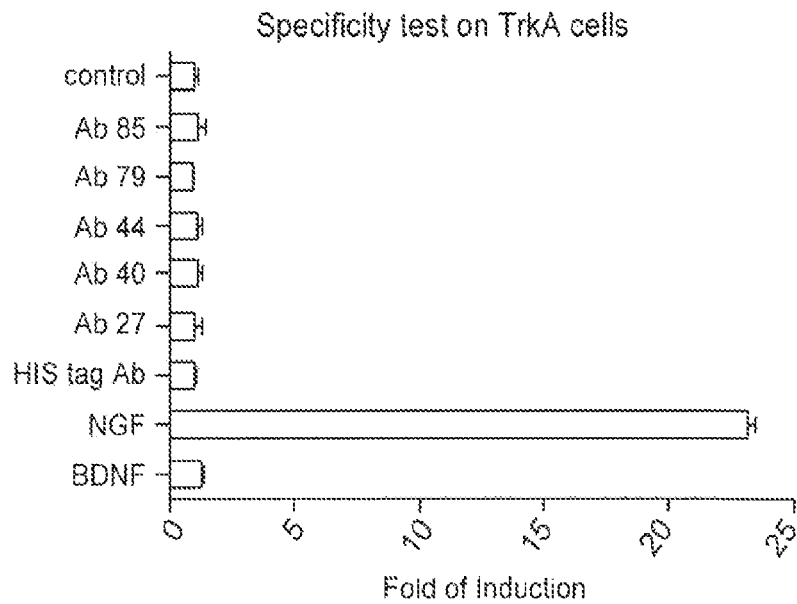
FIG. 4 shows selectivity of the identified TrkB agonist antibodies—the lack of effect on TrkA.

To further characterize activities of the identified antibodies, the selected scFv-Fc antibodies were purified using a Protein G affinity column and tested in the reporter cell assay to measure potency relative to BDNF (FIG. 3). As indicated in the figure, several Abs were full agonists as compared to BDNF while others showed partial agonism. Of the Abs purified and tested, potencies varied from 0.3-30 nM. Ab NFAT-85 showed the highest potency ($EC_{50}$=1 nM) and displayed full efficacy. All TrkB agonist Abs were tested for selectivity in a TrkA reporter cell. FIG. 4 shows that neither BDNF nor any of the Abs activated TrkA while NGF gave the expected robust response, confirming selectivity.

Amino acid sequences of some of the selected TrkB agonist scFv antibodies are shown in Table 1. Identified antibody clones from the "CRE" reporter screen are denoted "CRE-" in the table, and antibodies identified from the "NFAT" reporter screen are designated "NFAT-". The heavy chain and light chain variable region sequences and other sequence elements (e.g., CDRs) of the scFv antibodies are designated by the sequence identifiers listed in Table 2.

TABLE 1

TrkB agonist scFV antibodies identified from functional screen

CRE-6 (SEQ ID NO: 1)
MAQVQLVQSGAEVKKPGESLKISCKGSGYSFTSYWIGWVRQMPGKGLEWMGIIYP
GDSDTRYSFSFQGQVTISADKSISTAYLQWRSLKASDTAMYYCARQGASSTSYDYW
GQGPRSPSPQSGGGSGGGGSGGGGSEIVLTQSPSSLSASVGDRVTITCRASQSISSYLN
WYQQKPGKAPKLLIYAASSLQNGVPSRFSGSGSGTDFTLTISSLQPEDFATYYCQQA
NSFPVAFGQGTKVEIKR

CRE-30 (SEQ ID NO: 2)
MAQVQLVESGAALVQPGGSLRLSCAASGFIFSRYNMNWVRQAPGKRPEWISFINTD
GSVIHYADSVEGRFTVSRDNVNNSLYLQMNDLRDDDTAVYYCVRQMLFWGQGTL
VTVSSGGGGGGSQAVLTQPSSLSASPGASASLTCTLRSGINVGTYRIYWYQQKPGSP
PQYLLRYKSDSDKHQGSGVPSRFSGSKAASANAGILLISGLQSEDEADYYCAIWHSS
AWVFGGGTQLTVL

CRE-31 (SEQ ID NO: 3)
MAQVQLVQSGAALVQPGGSLRLSCAASGFIFSRYNMNWVRQAPGKRPEWISFINTD
GSVIHYADSVEGRFTVSRDNVNNSLYLQMNDLRDDDTAVYYCVRQMLFWGQGTL
VTVSSGGGGSQAVLTQPSSLSASPGASVSLTCTLRSGINVGAYRVYWYQQKPGSPPQ
FLLRYKTDSDKQQGSGVSSRFSGSRDASANAGILLISGLRSEDEADYYCAIWHSSAW
VFGGGTQLTVL

CRE-39 (SEQ ID NO: 4)
MAQVQLQESGAALVQPGGSLRLSCAASGFIFSRYNMNWVRQAPGKRPEWISFINTD
GSVIHYADSVEGRFSVSRDNVNNSLYLQMNDLRDDDTAVYYCVRQMLFWGQGTT
VTVSSGGGGGSQAVLTQPSSLSASPGASVSLTCTLRSGINVGAYRIYWYQQKPGSPP
QFLLRYKSDSDKQQGSGVPSRFSGSRDASANAGILLISGLRSEDEADYYCAIWHSSA
WVFGGGTQLTVL

CRE-53 (SEQ ID NO: 5)
MAQVQLVESGAALVQPGGSLRLSCAASGFIFSRYNMNWVRQAPGKRPEWISFINTD
GSVIHYADSVEGRFTVSRDNVNNSLYLQMNDLRDDDTAVYYCVRQMLFWGQGTT
VTVSSGSGGGSQAVLTQPSSLSASPGASVSLTCTLRSGINVGAYRVYWYQQKPGSP
PQFLLRYKTDSDKQQGSGVPSRFSGSRDASANAGILLISGLRSEDEADYYCAIWHSS
AWVFGGGTKLTVL

CRE-83 (SEQ ID NO: 6)
MAQVQLVESGAALVQPGGSLRLSCAASGFIFSRYNMNWVRQAPGKRPEWISFINTD
GSVIHYADSVEGRFTVSRDNVNNSLYLQMNDLRDDDTAVYYCVRQMLFWGQGTL
VTVSSGGGGGGSQAVLTQPSSLSASPGASASLTCTLRSGINVGTYRIYWYQQKPGSP
PQYLLRYKSDSDKQQGSGVPSRFSGSRDASANAGILLISGLRSEDEADYYCAIWHSS
AWVFGGGTKLTVL

CRE-87 (SEQ ID NO: 7)
MAQVQLVESGAALVQPGGSLRLSCAASGFIFSRYNMNWVRQAPGKRPEWISFINTD
GSVIHYADSVEGRFTVSRDNVNNSLYLQMNDLRDDDTAVYYCVRQMLFWGQGTL
VTVSSGGGGGGSQAVLTQPSSLSASPGASASLTCTLRSGINVGTYRIYWYQQKPGSP
PQYLLRYKSDSDKQQGSGVPSRFSGSRDASANAGILLISGLRSEDEADYYCAIWHSS
ACVFGGGTKLTVL

CRE-93 (SEQ ID NO: 8)
MAQVQLQESGAALVQPGGSLRLSCAASGFIFSRYNMNWVRQAPGKRPEWISFINTD
GSVIHYADSVEGRFSVSRDNVNNSLYLQMNDLRDDDTAVYYCARQLLYWGQGTV
VTVSSGGGGGSQAVLTQPSSLSASPGASVSLTCTLRSGINVGAYRIYWYQQKPGSPP
QFLLRYKSGSDKHQGSGVPSRFSGSKDASANAGILLISGLRSEDEADYYCAIWHSSA
WVFGGGTQLTVL

NFAT-27 (SEQ ID NO: 9)
QVQLVQSGAEVKKPGESLKISCKGSGYSFTSYWIGWVRQMPGKGLEWMGIIYPGDS
DTRYSPSFQGQVTISVDNSVSTTYLQLNNLQASDTAMYYCATRVLPAGHFYTLDVW
GQGTLVTVSSGGGGSGGGGSGGGGSSYVLTQPPSVSVAPGETAILTCVGNNIGDKFV

TABLE 1-continued

TrkB agonist scFV antibodies identified from functional screen

HWYQQKPGQAPVLVMY<u>YDS</u>DRPSGIPERFSGSNSGNTATLTISRVEAGDEGEYYC<u>Q
WVDNSSNQGV</u>FGGGTQLTVL

NFAT-40 (SEQ ID NO: 10)
MAQVQLQQSGPGLVKPSQTLSLTCVISGDS<u>VSDNSGAWN</u>WIRQSPSRGLEWLGRTY
YRSK<u>WYT</u>DYADSVKSRITIIPDIPKNQFSLHLNSVTPEDTAVYYC<u>VRGYYYAFHI</u>WG
QGTMVTVS*SGSGGGGSS*SELTQDPAVSVALGQTVRITCQGD<u>SLRTYY</u>ASWYQQKPG
QAPLLVIY<u>GKN</u>NRPSGIPDRFSGSSSGNTASLTITGAQAEDEADYYC<u>NSRDGSGNNV
V</u>FGGGTKLTVL

NFAT-44 (SEQ ID NO: 11)
MAQVQLVQSGSELKKPGASVKVSCKAS<u>GYTFTSYA</u>MNWVRQAPGQGLEWMGW<u>I
NTNTGNP</u>TYAQGFTGRFVFSLDTSVSTAYLQISSLKAEDTAVYYC<u>ASRLAAAGFDY</u>
WGQGTLVTVS*SGGGGSGGGGSGGGGS*QAVLTQPSSLSASPGASASLTCTLR<u>SGINVG
TYRI</u>YWYQQKPGSPPQYLLR<u>YKSDSDK</u>QQGSGVPSRFSGSKDASANAGILLISGLRS
EDEADYYC<u>AIWHSSAWV</u>FGGGTQLTVL

NFAT-79 (SEQ ID NO: 12)
MAQVQLVESGAALVQPGGSLRLSCAAS<u>GFIFSRYN</u>MNWVRQAPGKRPEWISF<u>INTD
GSVI</u>HYADSVEGRFTVSRDNVNNSLYLQMNDLRDDDTAVYYC<u>VRQMLF</u>WGQGTL
VTVS*SGSGGGGS*QAVLTQPSSLSASPGASVSLTCTLR<u>SGINVGAYRI</u>YWYQQKPGSP
PQYLLR<u>YKSDSDK</u>QQGSGVPSRFSGSKDASANAGILLISGLRSEDEADYYC<u>AIWHSS
AWV</u>FGGGTKLTVL

NFAT-85 (SEQ ID NO :13)
MAQVQLQQSGPGLVKPSQTLSLTCVISGDS<u>VSDNSGAWN</u>WIRQSPSRGLEWLGRTY
YRSK<u>WYT</u>DYADSVKSRITIIPDIPKNQFSLHLNSVTPEDTAVYYC<u>VRGYYYAFHI</u>WG
QGTMVTVS*SGSGGGGSS*SELTQDPAVSVALGQTVRITCQGD<u>SLRTYY</u>ASWYQQKPG
QAPVLVAA<u>GKN</u>NRPSGIPDRFSASSSGNTASLTITGAQAEDEADYYC<u>SSRDSSRSHH
LL</u>FGGGTKVTVL

Each scFV sequence includes the heavy chain variable region sequence connected to the light chain variable region sequence via a GS rich linker (italicized) The heavy chain CDR sequences are underlined, and the light chain CDR sequences double underlined,

TABLE 2

Sequence components of TrkB agonist scFV antibodies

| scFv (SEQ ID NO:) | H chain variable region (SEQ ID NO:) | L chain variable region (SEQ ID NO:) | Linker (SEQ ID NO:) | HCDRs 1-3 (SEQ ID NOs:) | LCDRs 1-3 (SEQ ID NOs:) |
|---|---|---|---|---|---|
| CRE-6 (1) | 14 | 15 | 40 | 46, 47, 48 | 49, AAS, 50 |
| CRE-30 (2) | 16 | 17 | 41 | 51, 52, 53 | 54, 55, 56 |
| CRE-31 (3) | 18 | 19 | 42 | 51, 52, 53 | 57, 58, 56 |
| CRE-39 (4) | 20 | 21 | 43 | 51, 52, 53 | 57, 55, 56 |
| CRE-53 (5) | 22 | 23 | 44 | 51, 52, 53 | 57, 58, 56 |
| CRE-83 (6) | 24 | 25 | 41 | 51, 52, 53 | 54, 55, 56 |
| CRE-87 (7) | 26 | 27 | 41 | 51, 52, 53 | 54, 55, 56 |
| CRE-93 (8) | 28 | 29 | 43 | 51, 52, 60 | 57, 61, 56 |
| NFAT-27 (9) | 30 | 31 | 45 | 46, 47, 62 | 63, YDS, 64 |
| NFAT-40 (10) | 32 | 33 | 44 | 65, 66, 67 | 68, GKN, 69 |
| NFAT-44 (11) | 34 | 35 | 45 | 70, 71, 72 | 54, 55, 56 |
| NFAT-79 (12) | 36 | 37 | 44 | 51, 52, 53 | 57, 55, 56 |
| NFAT-85 (13) | 38 | 39 | 44 | 65, 66, 67 | 68, GKN, 73 |

Example 2. Function of TrkB Agonist Antibodies in Signal Transduction

Figure 5:
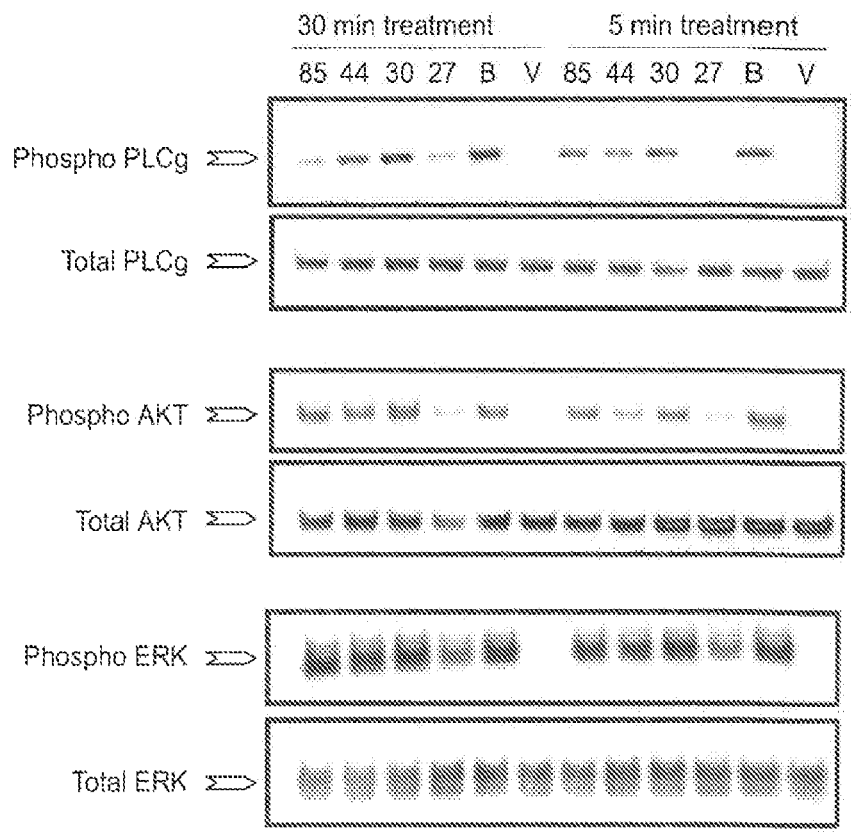
FIG. 5 shows that signaling of TrkB agonist Abs resulted in activation of P-PLCγ, P-Akt and P-MAPK in TrkB reporter cells.

Additional characterization of TrkB signaling by agonist Abs was carried out in the CHO reporter cell and compared to that of BDNF. Agonist Abs stimulated phosphorylation of P-PLCγ, P-Akt and P-MAPK signaling at 5 and 30 min, albeit to varying degrees (Figure B5); the levels and time course varied compared to BDNF but signal strength tended to correlate with effects on fluorescent signal in the reporter cell (see FIG. 5).

Figure 6:
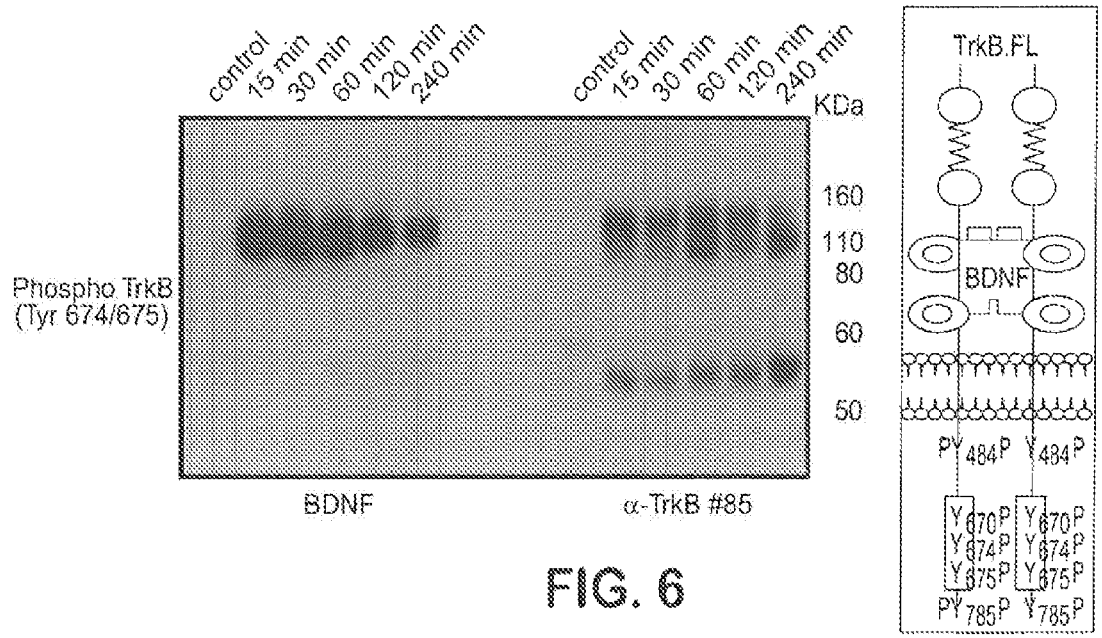
FIG. 6 shows agonist Ab-induced TrkB phosphorylation in cultured mouse cortical neurons.

Canonical signaling of BDNF/TrkB involves phosphorylation cascades through Akt, MAPK and PLCγ pathways. BDNF functions, such as survival, differentiation, neurite outgrowth, and synaptic plasticity have been ascribed to various aspects of these pathways. The identified TrkB agonist Abs were also tested for trophic activity and signaling in primary neurons. It was found that Abs NFAT-85, NFAT-44 and NFAT-27 maintained survival of mouse sensory neurons over 3 days in culture, similar to BDNF (not shown). Incubation of mouse cortical neurons with Ab NFAT-85 resulted in time-dependent tyrosine phosphorylation of TrkB. However, the pattern of TrkB phosphoproteins was distinct from that of BDNF, possibly revealing cleaved TrkB products (FIG. 6). Potential differential signal transduction with TrkB agonist Abs is currently under investigation.

Figure 7:
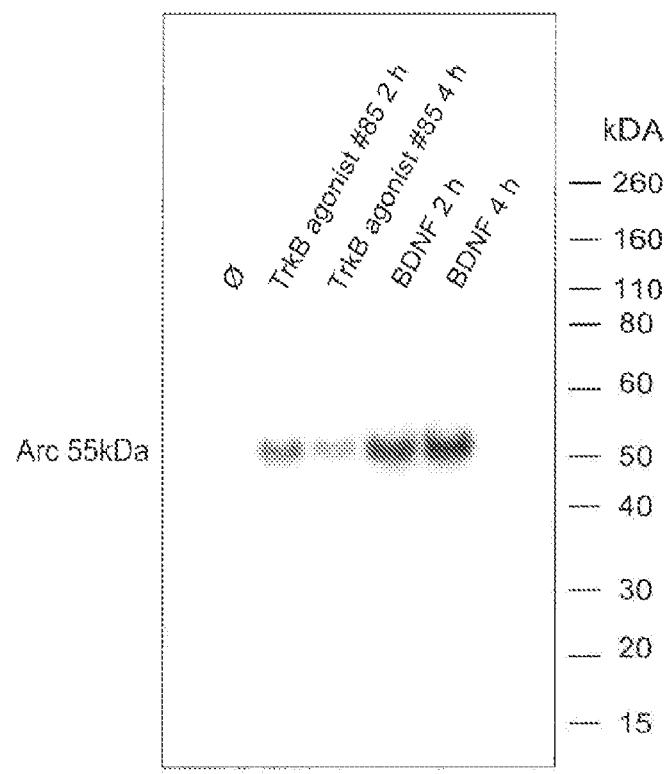
FIG. 7 shows expression of Arc induced by BDNF and TrkB agonist Ab NFAT-85.

To examine downstream targets of BDNF activation, the synaptic protein Arc was measured in mouse primary cortical neurons after Ab or BDNF treatment. Arc was originally identified as a cytoskeleton-associated protein. Recent studies link transient increases in Arc expression to stable expansion of the F-actin network in dendritic spines, which is believed to underlie morphological enlargement of the synapse and stable LTP. BDNF, long implicated in synaptic plasticity and memory storage, activates Arc-dependent consolidation and is necessary for actin-dependent spine enlargement. Current evidence further suggests a possible reciprocal interaction between F-actin formation, Arc, and translation during LTP consolidation. The results from this study are shown in FIG. 7. As with BDNF, antibody NFAT-85 stimulated Arc after 2-4 hr of incubation.

Figure 8:
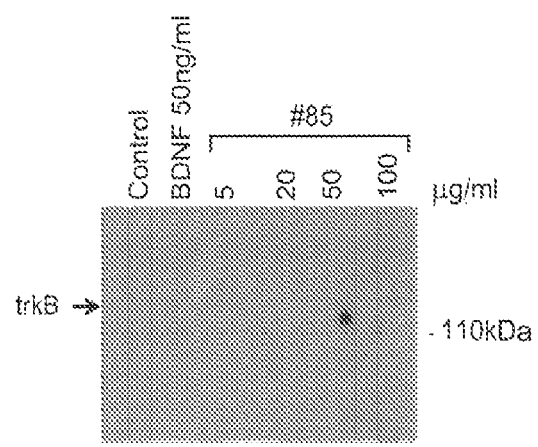
FIG. 8 shows TrkB phosphorylation induced by agonist antibody NFAT-85 in mouse embryonic stem cells.

Since anti-TrkB Agonist Abs were discovered by panning and selection with the human TrkB receptor, we determined the relative potency of Abs to rodent cells for future in vitro and in vivo studies. To examine this, we utilized a mouse embryonic stem cell line cell shown previously to respond to BDNF and compared TrkB phosphorylation stimulated by Ab NFAT-85 and BDNF. It was found that Ab NFAT-85 increased phosphorylation in a concentration-dependent fashion. However, the potency was at least two orders of magnitude less than its effect on the human reporter cell (~1 nM). In both mouse and human cells BDNF gave robust signaling at ~2 nM (FIG. 8).

Collectively, the signal transduction and downstream marker studies are consistent with TrkB engagement by the agonist Abs in a selective manner. Concentration-response in mouse cells defines a relative potency of Ab NFAT-85 for further rodent studies.

Example 3. Effect of TrkB Angonist Abs in Retinal Culture Systems

To initiate studies on the effects of TrkB agonists on retinal physiology in vitro, a mouse retinal explant culture system was established. Briefly, retinae from adult mice were dissected and placed in culture medium (RGC layer facing up) for periods of 0-14 days. By definition the RGC are axotomized; during this period there is progressive loss of various retinal layers and of RGC dendritic fields. RGC dendritic retraction is evident as early 6 hr in culture, as assessed by Sholl analysis, which measures dendritic field parameters as a function of distance from the cell soma. By 3 days in culture there is significant loss of dendrite intersections and dendrite branches.

The 3-day culture period provides a good dynamic range to test for neuroprotectant or neuroregenerative effects of BDNF and of TrkB agonist Abs on dendritic arbors of RGCs. It was observed that incubation of explants with 100 ng/ml BDNF significantly blocks dendrite retraction, such that the area under the Sholl curve and dendritic branchings after 3 days in culture resemble those of time-zero explants, suggesting complete protection of the dendritic retraction response to axotomy. To determine if BDNF was capable of reversing the axotomy-induced dendritic retraction, explants were maintained in culture for 3 days, at which time BDNF was added, and Sholl analysis performed. Strikingly, delayed application of BDNF reversed the retraction response to parameters, again resembling those of time-zero explants, suggesting that BDNF induces a neuroregenerative sprouting response in the damaged neurons.

Figure 9:
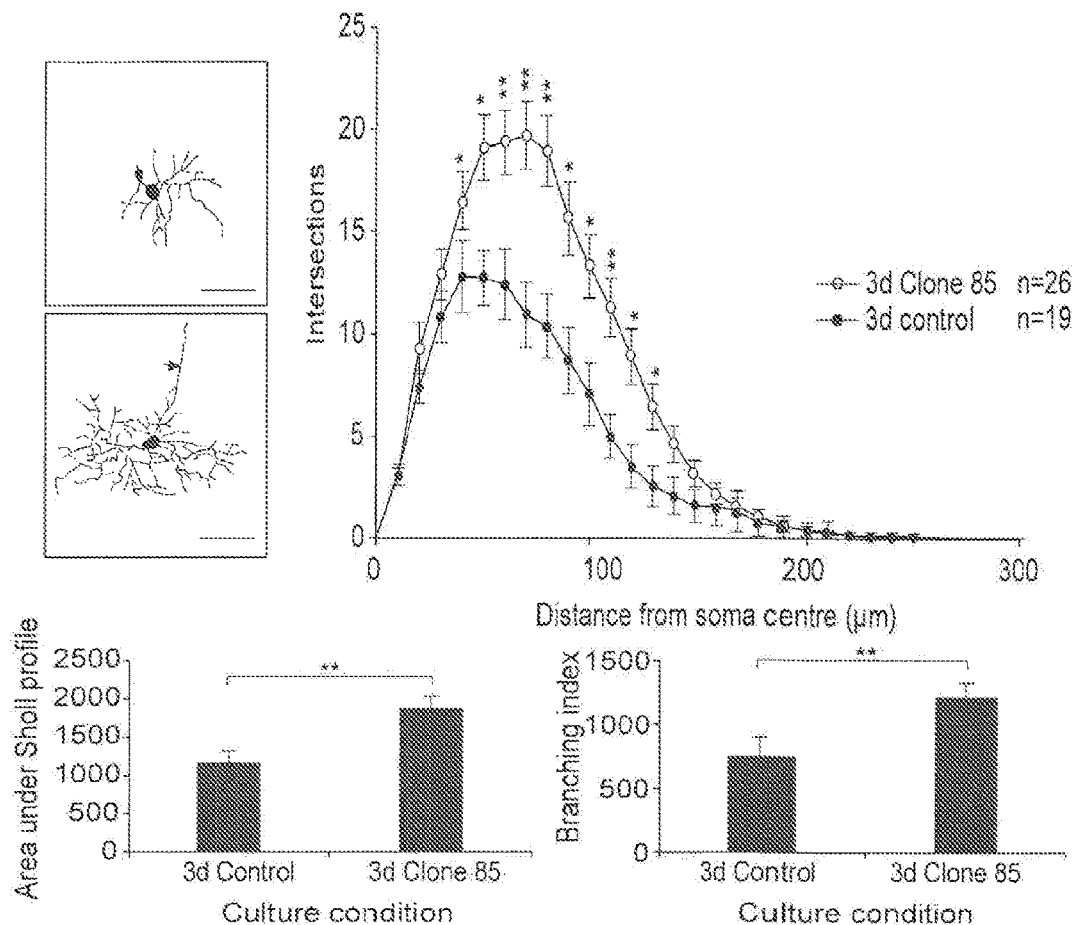
FIG. 9 shows that TrkB agonist Ab NFAT-85 prevents ROC dendrite retraction.

This paradigm establishes the groundwork to test whether TrkB agonist Abs can prevent dendritic retraction in retinal explants similar to that observed for BDNF. FIG. 9 shows that Ab NFAT-85 maintained dendritic parameters of axotomized ROC dendrites identical in magnitude to those of BDNF, corroborating biochemical and signal transduction parameters observed for Ab NFAT-85 in other cell types. Future experiments will determine the effects of delayed Ab NFAT-85 administration, as well as the durability of the effects of agonist Abs in this culture system.

In corroboration of the above, unpublished results, two recent reports have shown trophic effects of BDNF on RGC. First, Johnson et al. (Invest. Ophthalmol. Vis. Sci. 57:253-264, 2016) showed that administration of BDNF+CNTF (ciliary neurotrophic factor) to mouse retinal explants was capable of improving the number of branch segments, junctions and terminal branches of RGCs at 7 days. Also, Domenici et al. (PloS One 9(12):e115579, 2014) showed that intravitreal or topical application of BDNF improved visual function as assessed electrophysiologically in the DBA/2J mouse model of spontaneous glaucoma (not shown). Interestingly these effects occurred independently of elevated IOP.

Example 4. Efficacy of TrkB Agonist Abs in a Rat Model of Glaucoma

The ocular hypertensive (OHT) model of glaucoma was performed in Brown Norway rats by injection of sterile 5 µm magnetic microbeads into the anterior eye chamber. The experimental procedures were essentially carried out as described in Samsel et al., Invest. Ophthalmol. 52:1671, 2011; and Morgan and Tribble, Exp. Eye Res. 141:9-14, 2015. A magnet was used to draw the beads to the iridocorneal canal, disrupting the trabecular meshwork, preventing outflow of vitreous and subsequently elevating intraocular pressure (IOP). Elevations in IOP were measured periodically with a rebound tonometer. Bead injections were made in the left eye with the right eye serving as a control.

Figure 10:
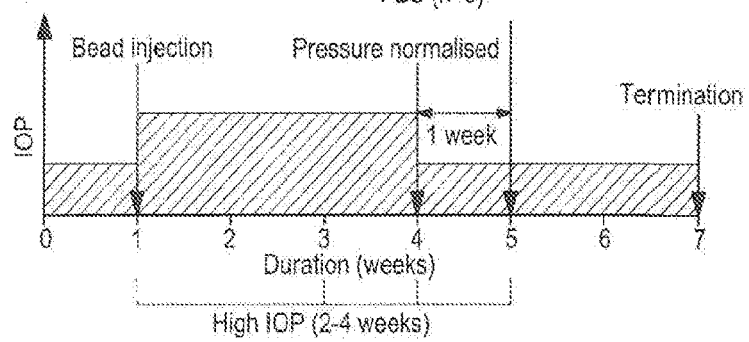
FIG. 10 is an experimental paradigm of efficacy studies of effect of TrkB agonist antibodies in rat model of glaucoma.
Figure 10:
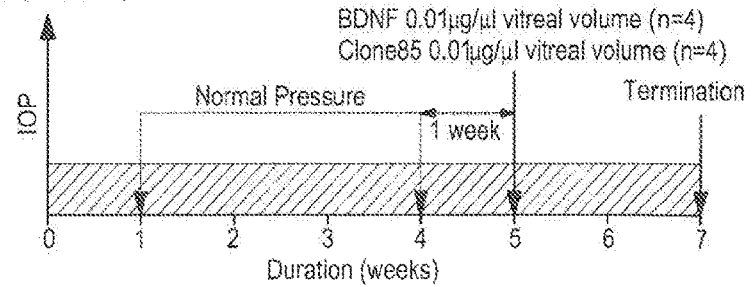

At 5 weeks post bead injection, the rats were administered via intravitreal injection into the left eye a phosphate buffered saline (PBS), 500 ng of TrkB agonist antibody NFAT-85 (Ab85), or 500 ng of BDNF in a volume of 1 µl. In some animals the effect of Ab85 or BDNF were determined in normotensive (NT) eyes (not receiving magnetic microbead injections). Two weeks later (7 weeks post microbead injection) rats were sacrificed, retinae were removed and prepared for diolistic labeling of retinal ganglion cells and their dendritic arbors. Arbor morphology (dendritic branching index, dendritic length and dendrite intersections) was quantified by Sholl analysis. An average of 6-10 cells were analyzed per retina. The experiment paradigm is outlined in FIG. 10.

Figure 11:
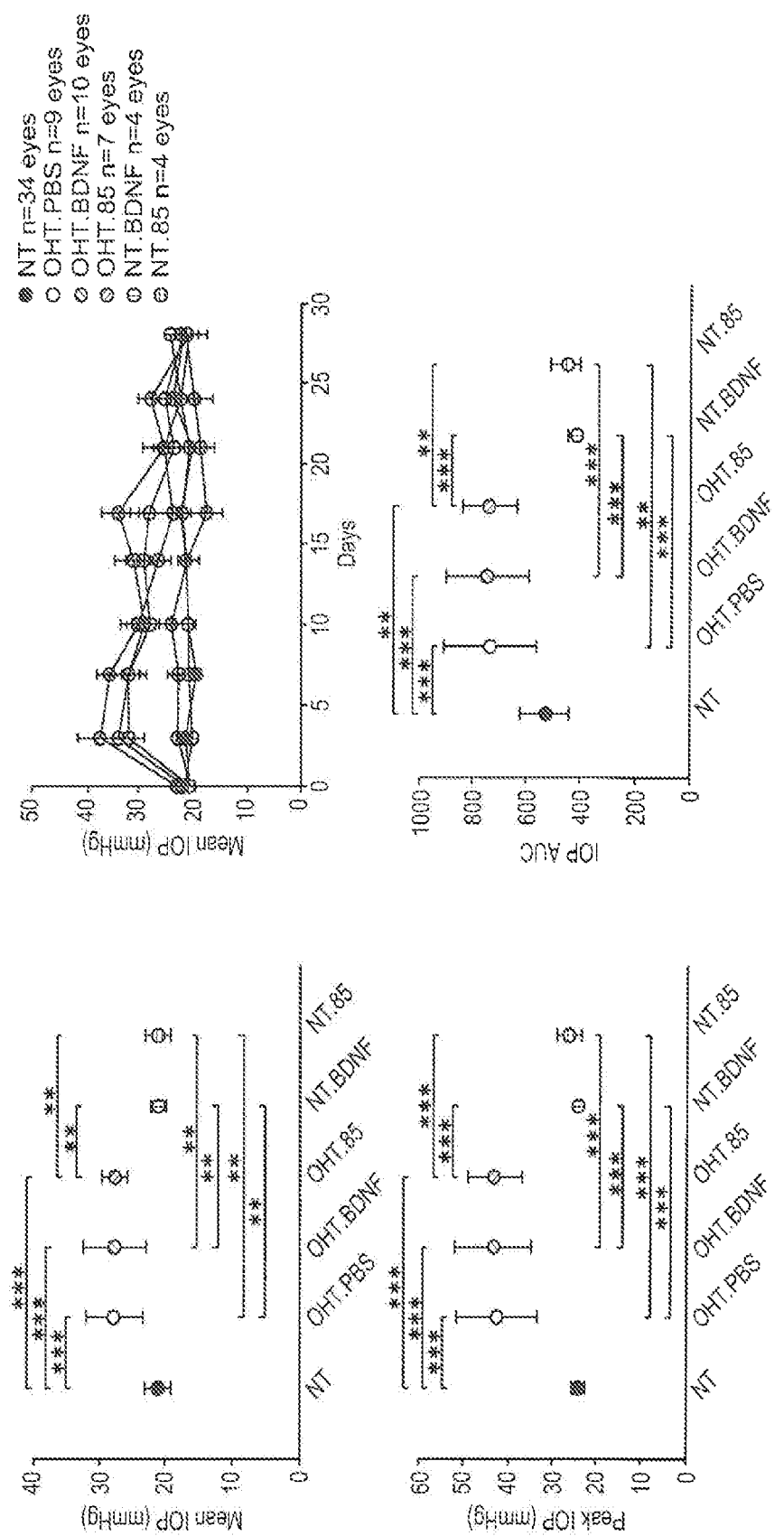
FIG. 11 shows TOP characteristics for the OHT model in rats.

FIG. 11 shows the Mean IOP and Peak IOP levels (in mm Hg) for the OHT and NT groups of rats treated with PBS, Ab85 or BDNF. In this method IOP was elevated early after microbead injection, remained elevated for ~3 weeks and returned to normal levels by 4 weeks.

Figure 12:
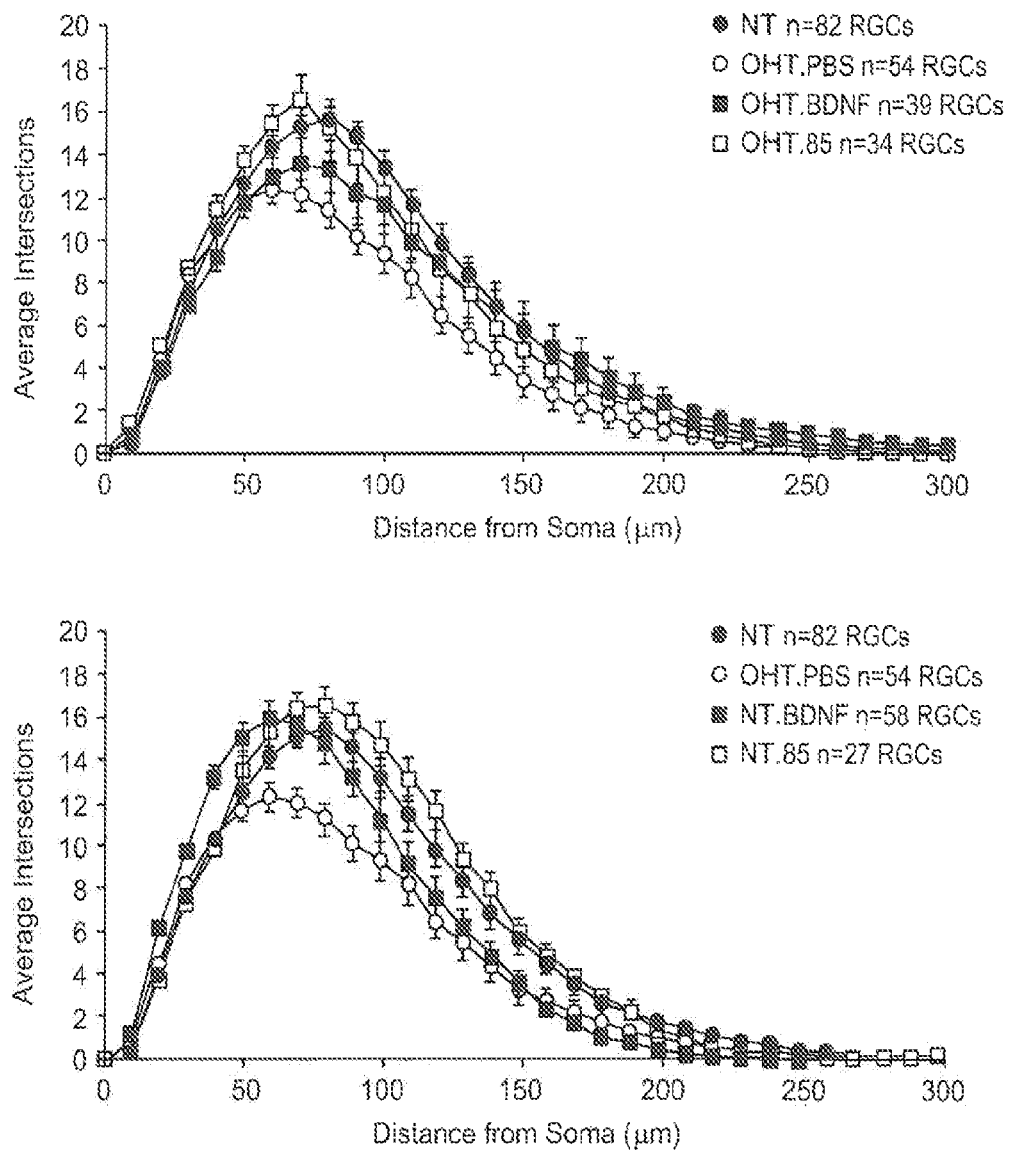
FIG. 12 shows Sholl plot analysis of the effect of TrkB agonist Ab85 and BDNF in OHT rats.

FIG. 12 shows quantification of average dendritic arbor intersections as assessed by Sholl analysis. The top graph compares OHT rats treated with various agents compared to a normotensive eye (NT) control. Both BDNF and to a greater degree Ab85 show increased intersections compared to PBS-treated eyes, and are not different from NT eyes. The bottom plot shows that treatment of NT eyes with BDNF or Ab85 did not significantly alter average intersections (OHT plotted as a point of comparison).

Figure 13:
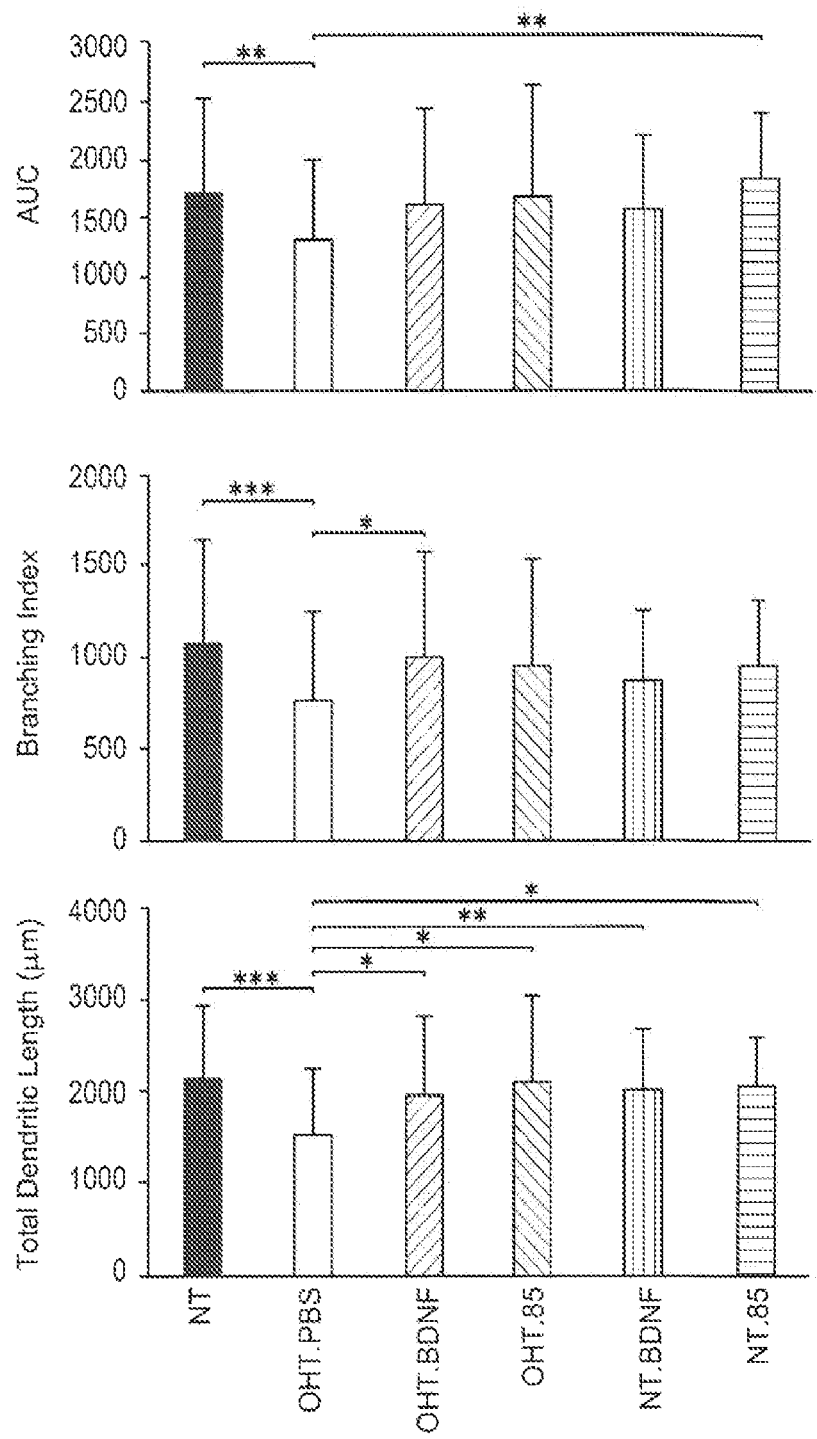
FIG. 13 illustrates dendritic metrics for Sholl analysis shown in FIG. 12.

FIG. 13 represents statistical comparisons of the area under the curve (AUC), branching index and dendritic length for the Sholl analyses shown in FIG. 12. For all measures, OHT+PBS rats were significantly reduced compared to NT eyes. In addition, OHT+either Ab85 or BDNF ameliorated these measures to values equal to NT eyes. Neither Ab85 nor BDNF treatment of NT eyes were different from NT controls.

The results from these studies demonstrated a positive, regenerative effect of TrkB agonist Abs on dendritic arbors of rat retinal ganglion neurons in a model of hypertensive glaucoma. Importantly, these regenerative effects occur after the induction of injury caused by the elevated intraocular pressure, similar to post-lesion treatment paradigm as is practiced clinically for glaucoma.

Example 5. Bispecific Antibody Targeting TrkB and TNF

We then attempted to generate a bispecific antibody from the TrkB agonist antibody Ab85 described herein and the well-known anti-TNF antibody Humira (Adalimumab), and a proof of concept bispecific antibody configuration was created. This bispecific molecule configuration contains one arm of Ab85 (TrkB antibody) and the other arm of Adalimumab. Briefly, Ab85 scFv fragment was fused to a human IgG1 Fc fragment with Y407T mutation, the resulting fusion protein is shown in SEQ ID NO:74 (Ab85-Fc(407)), Meanwhile, Adalimumab Fab heavy chain was fused to a human IgG1 Fc fragment with T366Y mutation. The resulting fusion protein is shown in SEQ ID NO:75 (Adalimumab-heavy-Fc (366)).

For expression and assembly of the bispecific antibody, these two fusion sequences (Ab85-Fc(407), Adalimumab-heavy-Fc (366)) along with an Adalimumab light coding encoding vector are to be transfected together into Expi 293 cells. The assembled antibodies can then purified via Protein G affinity chromatography.

(Ab85-Fc(407)
SEQ ID NO: 74
MAQVQLQQSGPGLVKPSQTLSLTCVISGDSVSDNSGAWNWIRQSPSRGLE

WLGRTYYRSKWYTDYADSVKSRITIIPDIPKNQFSLHLNSVTPEDTAVYY

CVRGYYYAFHIWGQGTMVTVSSGSGGGGSSSELTQDPAVSVALGQTVRIT

CQGDSLRTYYASWYQQKPGQAPVLVAAGKNNRPSGIPDRFSASSSGNTAS

LTITGAQAEDEADYYCSSRDSSRSHHLLFGGGTKVTVLGGLGGLASEPKS

CDKTHTCPPCPAPELLGGPSVFLFPPKPKDTLMISRTPEVTCVVVDVSHE

DPEVKFNWYVDGVEVHNAKTKPREEQYNSTRYVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLTSKLTVDKSRWQQ

GNVFSCSVMHEALHNYHYQKSLSLSPGK (Adalimumab-heavy-Fc (366))
SEQ ID NO: 75
EVQLVESGGGLVQPGRSLRLSCAASGFTFDDYAMHWVRQAPGKGLEWVSA

ITWNSGHIDYADSVEGRFITSRDNAKNSLYLQMNSLRAEDTAVYYCAKVS

YLSTASSLDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLYCLVKGFYPSDIAVEWESNGQPENNYKTTPP

VLDSDGSFFLYSKLTVDKSRWQQGNVFSCSVMHEALHNHYTQKSLSLSPG

K

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

We claim:

1. An isolated tropomyosin receptor kinase B (TrkB) agonist antibody or an antigen-binding fragment that specifically binds to TrkB comprising a heavy chain variable region (VH) comprising three complementarity determining regions (HCDRs1-3) and a light chain variable region (VL) comprising three complementarity determining regions (LCDRs1-3), wherein the HCDR1 comprises VSDNSGAWN (SEQ ID NO:65), the HCDR2 comprises YRSKWYT (SEQ ID NO:66), the HCDR3 comprises VRGYYYAFHI (SEQ ID NO:67), the HCDR1 comprises SLRTYY (SEQ ID NO:68), the HCDR1 comprises GKN, and the HCDR1 comprises SSRDSSRSHHLL (SEQ ID NO:73).

2. The antibody or antigen-binding fragment of claim 1, wherein the VH comprises the amino acid sequence of SEQ ID NO:38 and the VL comprises the amino acid sequence of SEQ ID NO:39.

3. The antibody or antigen-binding fragment of claim 1, wherein the antibody is an IgG antibody and wherein the antigen-binding fragment is a Fab, a scFv, or a dsFv of the antibody.

4. The antibody or antigen-binding fragment of claim 3, wherein the scFV comprises the amino acid sequence of SEQ ID NO: 13.

5. The antibody or antigen-binding fragment according to claim 1, wherein the antibody is recombinant, chimeric or humanized.

6. An antibody-conjugate comprising the antibody or antigen-binding fragment thereof of claim 1, wherein the antibody or the antigen-binding fragment thereof is linked to a synthetic molecule, wherein the synthetic molecule is a conjugate moiety selected from the group consisting of a detectable label, a tissue specific targeting moiety and a binding moiety for covalent or non-covalent conjugation.

7. A pharmaceutical composition comprising a therapeutically effective amount of the antibody or antigen-binding fragment of claim 1 and a pharmaceutically acceptable carrier.

8. A kit comprising the antibody or antigen-binding fragment of claim 1.

9. A method for promoting survival, synaptic function or neurite outgrowth of retinal ganglion cells (RGCs) in a subject suffering from an ocular degenerative disorder characterized by degeneration of RGCs, comprising administering to one or both eyes of the subject a pharmaceutical composition comprising a therapeutically effective amount of the TrkB agonist antibody or antigen-binding fragment of claim 1, thereby promoting survival or neurite outgrowth of RGCs in the subject; wherein the ocular degenerative disorder is selected from the group consisting of glaucoma, optic nerve injury, optic neuritis, optic neuropathy, central retinal artery occlusion, central retinal vein occlusion, diabetic neuropathy, age-related macular degeneration (AMD), anterior ischemic ocular neuropathy (AION) and diabetic retinopathy.

10. A method for promoting survival, synaptic function or neurite outgrowth of retinal ganglion cells (RGCs), comprising administering to cultured retinal ganglion cells a pharmaceutical composition comprising a therapeutically effective amount of the TrkB agonist antibody or antigen-binding fragment of claim 1, thereby promoting survival or neurite outgrowth of the RGCs in vitro.

* * * * *

SEQUENCE LISTING

```
<160> NUMBER OF SEQ ID NOS: 75

<210> SEQ ID NO 1
<211> LENGTH: 244
<212> TYPE: PRT
<213> ORGANISM: Artificial Sequence
<220> FEATURE:
<223> OTHER INFORMATION: Synthetic sequence

<400> SEQUENCE: 1

Met Ala Gln Val Gln Leu Val Gln Ser Gly Ala Glu Val Lys Lys Pro
1               5                   10                  15

Gly Glu Ser Leu Lys Ile Ser Cys Lys Gly Ser Gly Tyr Ser Phe Thr
                20                  25                  30

Ser Tyr Trp Ile Gly Trp Val Arg Gln Met Pro Gly Lys Gly Leu Glu
            35                  40                  45

Trp Met Gly Ile Ile Tyr Pro Gly Asp Ser Asp Thr Arg Tyr Ser Pro
        50                  55                  60

Ser Phe Gln Gly Gln Val Thr Ile Ser Ala Asp Lys Ser Ile Ser Thr
65                  70                  75                  80

Ala Tyr Leu Gln Trp Arg Ser Leu Lys Ala Ser Asp Thr Ala Met Tyr
                85                  90                  95

Tyr Cys Ala Arg Gln Gly Ala Ser Ser Thr Ser Tyr Asp Tyr Trp Gly
                100                 105                 110

Gln Gly Pro Arg Ser Pro Ser Pro Gln Ser Gly Gly Gly Ser Gly Gly
            115                 120                 125

Gly Gly Ser Gly Gly Gly Ser Glu Ile Val Leu Thr Gln Ser Pro
        130                 135                 140
```

```
Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Asn
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ala Asn Ser Phe Pro Val Ala Phe Gly Gln Gly Thr Lys Val
225                 230                 235                 240

Glu Ile Lys Arg

<210> SEQ ID NO 2
<211> LENGTH: 237
<212> TYPE: PRT
<213> ORGANISM: Artificial sequence
<220> FEATURE:
<223> OTHER INFORMATION: Synthetic sequence

<400> SEQUENCE: 2

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
    50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Leu Val Thr
                100                 105                 110

Val Ser Ser Gly Gly Gly Gly Gly Ser Gln Ala Val Leu Thr Gln
            115                 120                 125

Pro Ser Ser Leu Ser Ala Ser Pro Gly Ala Ser Ala Ser Leu Thr Cys
    130                 135                 140

Thr Leu Arg Ser Gly Ile Asn Val Gly Thr Tyr Arg Ile Tyr Trp Tyr
145                 150                 155                 160

Gln Gln Lys Pro Gly Ser Pro Pro Gln Tyr Leu Leu Arg Tyr Lys Ser
                165                 170                 175

Asp Ser Asp Lys His Gln Gly Ser Gly Val Pro Ser Arg Phe Ser Gly
            180                 185                 190

Ser Lys Ala Ala Ser Ala Asn Ala Gly Ile Leu Leu Ile Ser Gly Leu
            195                 200                 205

Gln Ser Glu Asp Glu Ala Asp Tyr Tyr Cys Ala Ile Trp His Ser Ser
        210                 215                 220

Ala Trp Val Phe Gly Gly Gly Thr Gln Leu Thr Val Leu
225                 230                 235

<210> SEQ ID NO 3
<211> LENGTH: 235
```

<212> TYPE: PRT
<213> ORGANISM: Artificial sequence
<220> FEATURE:
<223> OTHER INFORMATION: Synthetic sequence

<400> SEQUENCE: 3

Met Ala Gln Val Gln Leu Val Gln Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Leu Val Thr
            100                 105                 110

Val Ser Ser Gly Gly Gly Gly Ser Gln Ala Val Leu Thr Gln Pro Ser
            115                 120                 125

Ser Leu Ser Ala Ser Pro Gly Ala Ser Val Ser Leu Thr Cys Thr Leu
130                 135                 140

Arg Ser Gly Ile Asn Val Gly Ala Tyr Arg Val Tyr Trp Tyr Gln Gln
145                 150                 155                 160

Lys Pro Gly Ser Pro Pro Gln Phe Leu Leu Arg Tyr Lys Thr Asp Ser
            165                 170                 175

Asp Lys Gln Gln Gly Ser Gly Val Ser Ser Arg Phe Ser Gly Ser Arg
            180                 185                 190

Asp Ala Ser Ala Asn Ala Gly Ile Leu Leu Ile Ser Gly Leu Arg Ser
            195                 200                 205

Glu Asp Glu Ala Asp Tyr Tyr Cys Ala Ile Trp His Ser Ser Ala Trp
210                 215                 220

Val Phe Gly Gly Gly Thr Gln Leu Thr Val Leu
225                 230                 235

<210> SEQ ID NO 4
<211> LENGTH: 236
<212> TYPE: PRT
<213> ORGANISM: Artificial sequence
<220> FEATURE:
<223> OTHER INFORMATION: Synthetic sequence

<400> SEQUENCE: 4

Met Ala Gln Val Gln Leu Gln Glu Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
50                  55                  60

Ser Val Glu Gly Arg Phe Ser Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Thr Val Thr
            100                 105                 110

Val Ser Ser Gly Gly Gly Gly Ser Gln Ala Val Leu Thr Gln Pro
            115                 120                 125

Ser Ser Leu Ser Ala Ser Pro Gly Ala Ser Val Ser Leu Thr Cys Thr
130                 135                 140

Leu Arg Ser Gly Ile Asn Val Gly Ala Tyr Arg Ile Tyr Trp Tyr Gln
145                 150                 155                 160

Gln Lys Pro Gly Ser Pro Gln Phe Leu Arg Tyr Lys Ser Asp
                165                 170                 175

Ser Asp Lys Gln Gln Gly Ser Gly Val Pro Ser Arg Phe Ser Gly Ser
                180                 185                 190

Arg Asp Ala Ser Ala Asn Ala Gly Ile Leu Leu Ile Ser Gly Leu Arg
            195                 200                 205

Ser Glu Asp Glu Ala Asp Tyr Tyr Cys Ala Ile Trp His Ser Ser Ala
            210                 215                 220

Trp Val Phe Gly Gly Gly Thr Gln Leu Thr Val Leu
225                 230                 235

<210> SEQ ID NO 5
<211> LENGTH: 237
<212> TYPE: PRT
<213> ORGANISM: Artificial sequence
<220> FEATURE:
<223> OTHER INFORMATION: Synthetic sequence

<400> SEQUENCE: 5

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
                20                  25                  30

Arg Tyr Asn Met Asn Trp Val Arg Gln Ala Pro Gly Lys Arg Pro Glu
            35                  40                  45

Trp Ile Ser Phe Ile Asn Thr Asp Gly Ser Val Ile His Tyr Ala Asp
        50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Thr Val Thr
            100                 105                 110

Val Ser Ser Gly Ser Gly Gly Gly Ser Gln Ala Val Leu Thr Gln
            115                 120                 125

Pro Ser Ser Leu Ser Ala Ser Pro Gly Ala Ser Val Ser Leu Thr Cys
    130                 135                 140

Thr Leu Arg Ser Gly Ile Asn Val Gly Ala Tyr Arg Val Tyr Trp Tyr
145                 150                 155                 160

Gln Gln Lys Pro Gly Ser Pro Pro Gln Phe Leu Leu Arg Tyr Lys Thr
                165                 170                 175

Asp Ser Asp Lys Gln Gln Gly Ser Gly Val Pro Ser Arg Phe Ser Gly
            180                 185                 190

Ser Arg Asp Ala Ser Ala Asn Ala Gly Ile Leu Leu Ile Ser Gly Leu
        195                 200                 205

Arg Ser Glu Asp Glu Ala Asp Tyr Tyr Cys Ala Ile Trp His Ser Ser
    210                 215                 220

```
Ala Trp Val Phe Gly Gly Gly Thr Lys Leu Thr Val Leu
225                 230                 235

<210> SEQ ID NO 6
<211> LENGTH: 237
<212> TYPE: PRT
<213> ORGANISM: Artificial sequence
<220> FEATURE:
<223> OTHER INFORMATION: Synthetic sequence

<400> SEQUENCE: 6

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
    50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Leu Val Thr
            100                 105                 110

Val Ser Ser Gly Gly Gly Gly Ser Gln Ala Val Leu Thr Gln
            115                 120                 125

Pro Ser Ser Leu Ser Ala Ser Pro Gly Ala Ser Ala Ser Leu Thr Cys
130                 135                 140

Thr Leu Arg Ser Gly Ile Asn Val Gly Thr Tyr Arg Ile Tyr Trp Tyr
145                 150                 155                 160

Gln Gln Lys Pro Gly Ser Pro Pro Gln Tyr Leu Leu Arg Tyr Lys Ser
                165                 170                 175

Asp Ser Asp Lys Gln Gln Gly Ser Gly Val Pro Ser Arg Phe Ser Gly
            180                 185                 190

Ser Arg Asp Ala Ser Ala Asn Ala Gly Ile Leu Leu Ile Ser Gly Leu
        195                 200                 205

Arg Ser Glu Asp Glu Ala Asp Tyr Tyr Cys Ala Ile Trp His Ser Ser
    210                 215                 220

Ala Trp Val Phe Gly Gly Gly Thr Lys Leu Thr Val Leu
225                 230                 235

<210> SEQ ID NO 7
<211> LENGTH: 237
<212> TYPE: PRT
<213> ORGANISM: Artificial sequence
<220> FEATURE:
<223> OTHER INFORMATION: Synthetic sequence

<400> SEQUENCE: 7

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
```

-continued

```
                50                  55                  60
Ser Val Glu Gly Arg Phe Thr Val Ser Arg Asp Asn Val Asn Asn Ser
 65                  70                  75                  80

Leu Tyr Leu Gln Met Asn Asp Leu Arg Asp Asp Thr Ala Val Tyr
                 85                  90                  95

Tyr Cys Val Arg Gln Met Leu Phe Trp Gly Gln Gly Thr Leu Val Thr
                100                 105                 110

Val Ser Ser Gly Gly Gly Gly Gly Ser Gln Ala Val Leu Thr Gln
                115                 120                 125

Pro Ser Ser Leu Ser Ala Ser Pro Gly Ala Ser Ala Ser Leu Thr Cys
                130                 135                 140

Thr Leu Arg Ser Gly Ile Asn Val Gly Thr Tyr Arg Ile Tyr Trp Tyr
145                 150                 155                 160

Gln Gln Lys Pro Gly Ser Pro Pro Gln Tyr Leu Leu Arg Tyr Lys Ser
                165                 170                 175

Asp Ser Asp Lys Gln Gln Gly Ser Gly Val Pro Ser Arg Phe Ser Gly
                180                 185                 190

Ser Arg Asp Ala Ser Ala Asn Ala Gly Ile Leu Leu Ile Ser Gly Leu
                195                 200                 205

Arg Ser Glu Asp Glu Ala Asp Tyr Tyr Cys Ala Ile Trp His Ser Ser
210                 215                 220

Ala Cys Val Phe Gly Gly Gly Thr Lys Leu Thr Val Leu
225                 230                 235
```

<210> SEQ ID NO 8
<211> LENGTH: 236
<212> TYPE: PRT
<213> ORGANISM: Artificial sequence
<220> FEATURE:
<223> OTHER INFORMATION: Synthetic sequence

<400> SEQUENCE: 8

```
Met Ala Gln Val Gln Leu Gln Glu Ser Gly Ala Ala Leu Val Gln Pro
 1                   5                  10                  15

Gly Gly Ser Leu Arg Leu Ser Cys Ala Ala Ser Gly Phe Ile Phe Ser
                 20                  25                  30

Arg Tyr Asn Met Asn Trp Val Arg Gln Ala Pro Gly Lys Arg Pro Glu
                 35                  40                  45

Trp Ile Ser Phe Ile Asn Thr Asp Gly Ser Val Ile His Tyr Ala Asp
 50                  55                  60

Ser Val Glu Gly Arg Phe Ser Val Ser Arg Asp Asn Val Asn Asn Ser
 65                  70                  75                  80

Leu Tyr Leu Gln Met Asn Asp Leu Arg Asp Asp Thr Ala Val Tyr
                 85                  90                  95

Tyr Cys Ala Arg Gln Leu Leu Tyr Trp Gly Gln Gly Thr Val Val Thr
                100                 105                 110

Val Ser Ser Gly Gly Gly Gly Gly Ser Gln Ala Val Leu Thr Gln Pro
                115                 120                 125

Ser Ser Leu Ser Ala Ser Pro Gly Ala Ser Val Ser Leu Thr Cys Thr
                130                 135                 140

Leu Arg Ser Gly Ile Asn Val Gly Ala Tyr Arg Ile Tyr Trp Tyr Gln
145                 150                 155                 160

Gln Lys Pro Gly Ser Pro Pro Gln Phe Leu Leu Arg Tyr Lys Ser Gly
                165                 170                 175

Ser Asp Lys His Gln Gly Ser Gly Val Pro Ser Arg Phe Ser Gly Ser
```

```
                180                 185                 190
Lys Asp Ala Ser Ala Asn Ala Gly Ile Leu Leu Ile Ser Gly Leu Arg
            195                 200                 205

Ser Glu Asp Glu Ala Asp Tyr Tyr Cys Ala Ile Trp His Ser Ser Ala
            210                 215                 220

Trp Val Phe Gly Gly Gly Thr Gln Leu Thr Val Leu
225                 230                 235

<210> SEQ ID NO 9
<211> LENGTH: 245
<212> TYPE: PRT
<213> ORGANISM: Artificial sequence
<220> FEATURE:
<223> OTHER INFORMATION: Synthetic sequence

<400> SEQUENCE: 9

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Val Asp Asn Ser Val Ser Thr Thr Tyr
65                  70                  75                  80

Leu Gln Leu Asn Asn Leu Gln Ala Ser Asp Thr Ala Met Tyr Tyr Cys
                85                  90                  95

Ala Thr Arg Val Leu Pro Ala Gly His Phe Tyr Thr Leu Asp Val Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Ser Tyr Val Leu Thr Gln Pro
    130                 135                 140

Pro Ser Val Ser Val Ala Pro Gly Glu Thr Ala Ile Leu Thr Cys Val
145                 150                 155                 160

Gly Asn Asn Ile Gly Asp Lys Phe Val His Trp Tyr Gln Gln Lys Pro
                165                 170                 175

Gly Gln Ala Pro Val Leu Val Met Tyr Tyr Asp Ser Asp Arg Pro Ser
            180                 185                 190

Gly Ile Pro Glu Arg Phe Ser Gly Ser Asn Ser Gly Asn Thr Ala Thr
        195                 200                 205

Leu Thr Ile Ser Arg Val Glu Ala Gly Asp Glu Gly Glu Tyr Tyr Cys
    210                 215                 220

Gln Val Trp Asp Asn Ser Ser Asn Gln Gly Val Phe Gly Gly Gly Thr
225                 230                 235                 240

Gln Leu Thr Val Leu
            245

<210> SEQ ID NO 10
<211> LENGTH: 237
<212> TYPE: PRT
<213> ORGANISM: Artificial sequence
<220> FEATURE:
<223> OTHER INFORMATION: Synthetic sequence

<400> SEQUENCE: 10
```

Met Ala Gln Val Gln Leu Gln Gln Ser Gly Pro Gly Leu Val Lys Pro
1               5                   10                  15

Ser Gln Thr Leu Ser Leu Thr Cys Val Ile Ser Gly Asp Ser Val Ser
            20                  25                  30

Asp Asn Ser Gly Ala Trp Asn Trp Ile Arg Gln Ser Pro Ser Arg Gly
        35                  40                  45

Leu Glu Trp Leu Gly Arg Thr Tyr Tyr Arg Ser Lys Trp Tyr Thr Asp
50                  55                  60

Tyr Ala Asp Ser Val Lys Ser Arg Ile Thr Ile Pro Asp Ile Pro
65                  70                  75                  80

Lys Asn Gln Phe Ser Leu His Leu Asn Ser Val Thr Pro Glu Asp Thr
                85                  90                  95

Ala Val Tyr Tyr Cys Val Arg Gly Tyr Tyr Ala Phe His Ile Trp
            100                 105                 110

Gly Gln Gly Thr Met Val Thr Val Ser Ser Gly Gly Gly Gly
                115                 120                 125

Ser Ser Ser Glu Leu Thr Gln Asp Pro Ala Val Ser Val Ala Leu Gly
        130                 135                 140

Gln Thr Val Arg Ile Thr Cys Gln Gly Asp Ser Leu Arg Thr Tyr Tyr
145                 150                 155                 160

Ala Ser Trp Tyr Gln Gln Lys Pro Gly Gln Ala Pro Leu Leu Val Ile
                165                 170                 175

Tyr Gly Lys Asn Asn Arg Pro Ser Gly Ile Pro Asp Arg Phe Ser Gly
            180                 185                 190

Ser Ser Ser Gly Asn Thr Ala Ser Leu Thr Ile Thr Gly Ala Gln Ala
        195                 200                 205

Glu Asp Glu Ala Asp Tyr Tyr Cys Asn Ser Arg Asp Gly Ser Gly Asn
210                 215                 220

Asn Val Val Phe Gly Gly Gly Thr Lys Leu Thr Val Leu
225                 230                 235

<210> SEQ ID NO 11
<211> LENGTH: 250
<212> TYPE: PRT
<213> ORGANISM: Artificial sequence
<220> FEATURE:
<223> OTHER INFORMATION: Synthetic sequence

<400> SEQUENCE: 11

Met Ala Gln Val Gln Leu Val Gln Ser Gly Ser Glu Leu Lys Lys Pro
1               5                   10                  15

Gly Ala Ser Val Lys Val Ser Cys Lys Ala Ser Gly Tyr Thr Phe Thr
            20                  25                  30

Ser Tyr Ala Met Asn Trp Val Arg Gln Ala Pro Gly Gln Gly Leu Glu
        35                  40                  45

Trp Met Gly Trp Ile Asn Thr Asn Thr Gly Asn Pro Thr Tyr Ala Gln
50                  55                  60

Gly Phe Thr Gly Arg Phe Val Phe Ser Leu Asp Thr Ser Val Ser Thr
65                  70                  75                  80

Ala Tyr Leu Gln Ile Ser Ser Leu Lys Ala Glu Asp Thr Ala Val Tyr
                85                  90                  95

Tyr Cys Ala Ser Arg Leu Ala Ala Ala Gly Phe Asp Tyr Trp Gly Gln
            100                 105                 110

Gly Thr Leu Val Thr Val Ser Ser Gly Gly Gly Gly Ser Gly Gly Gly
        115                 120                 125

```
Gly Ser Gly Gly Gly Ser Gln Ala Val Leu Thr Gln Pro Ser Ser
    130                 135                 140
Leu Ser Ala Ser Pro Gly Ala Ser Ala Ser Leu Thr Cys Thr Leu Arg
145                 150                 155                 160
Ser Gly Ile Asn Val Gly Thr Tyr Arg Ile Tyr Trp Tyr Gln Gln Lys
                165                 170                 175
Pro Gly Ser Pro Pro Gln Tyr Leu Leu Arg Tyr Lys Ser Asp Ser Asp
            180                 185                 190
Lys Gln Gln Gly Ser Gly Val Pro Ser Arg Phe Ser Gly Ser Lys Asp
        195                 200                 205
Ala Ser Ala Asn Ala Gly Ile Leu Leu Ile Ser Gly Leu Arg Ser Glu
    210                 215                 220
Asp Glu Ala Asp Tyr Tyr Cys Ala Ile Trp His Ser Ser Ala Trp Val
225                 230                 235                 240
Phe Gly Gly Gly Thr Gln Leu Thr Val Leu
                245                 250

<210> SEQ ID NO 12
<211> LENGTH: 237
<212> TYPE: PRT
<213> ORGANISM: Artificial sequence
<220> FEATURE:
<223> OTHER INFORMATION: Synthetic sequence

<400> SEQUENCE: 12

Met Ala Gln Val Gln Leu Val Glu Ser Gly Ala Ala Leu Val Gln Pro
1               5                   10                  15
Gly Gly Ser Leu Arg Leu Ser Cys Ala Ala Ser Gly Phe Ile Phe Ser
            20                  25                  30
Arg Tyr Asn Met Asn Trp Val Arg Gln Ala Pro Gly Lys Arg Pro Glu
        35                  40                  45
Trp Ile Ser Phe Ile Asn Thr Asp Gly Ser Val Ile His Tyr Ala Asp
    50                  55                  60
Ser Val Glu Gly Arg Phe Thr Val Ser Arg Asp Asn Val Asn Asn Ser
65                  70                  75                  80
Leu Tyr Leu Gln Met Asn Asp Leu Arg Asp Asp Thr Ala Val Tyr
                85                  90                  95
Tyr Cys Val Arg Gln Met Leu Phe Trp Gly Gln Gly Thr Leu Val Thr
            100                 105                 110
Val Ser Ser Gly Ser Gly Gly Gly Ser Gln Ala Val Leu Thr Gln
        115                 120                 125
Pro Ser Ser Leu Ser Ala Ser Pro Gly Ala Ser Val Ser Leu Thr Cys
    130                 135                 140
Thr Leu Arg Ser Gly Ile Asn Val Gly Ala Tyr Arg Ile Tyr Trp Tyr
145                 150                 155                 160
Gln Gln Lys Pro Gly Ser Pro Pro Gln Tyr Leu Leu Arg Tyr Lys Ser
                165                 170                 175
Asp Ser Asp Lys Gln Gln Gly Ser Gly Val Pro Ser Arg Phe Ser Gly
            180                 185                 190
Ser Lys Asp Ala Ser Ala Asn Ala Gly Ile Leu Leu Ile Ser Gly Leu
        195                 200                 205
Arg Ser Glu Asp Glu Ala Asp Tyr Tyr Cys Ala Ile Trp His Ser Ser
    210                 215                 220
Ala Trp Val Phe Gly Gly Gly Thr Lys Leu Thr Val Leu
225                 230                 235
```

-continued

<210> SEQ ID NO 13
<211> LENGTH: 238
<212> TYPE: PRT
<213> ORGANISM: Artificial sequence
<220> FEATURE:
<223> OTHER INFORMATION: Synthetic sequence

<400> SEQUENCE: 13

```
Met Ala Gln Val Gln Leu Gln Gln Ser Gly Pro Gly Leu Val Lys Pro
1               5                   10                  15

Ser Gln Thr Leu Ser Leu Thr Cys Val Ile Ser Gly Asp Ser Val Ser
            20                  25                  30

Asp Asn Ser Gly Ala Trp Asn Trp Ile Arg Gln Ser Pro Ser Arg Gly
        35                  40                  45

Leu Glu Trp Leu Gly Arg Thr Tyr Tyr Arg Ser Lys Trp Tyr Thr Asp
    50                  55                  60

Tyr Ala Asp Ser Val Lys Ser Arg Ile Thr Ile Ile Pro Asp Ile Pro
65                  70                  75                  80

Lys Asn Gln Phe Ser Leu His Leu Asn Ser Val Thr Pro Glu Asp Thr
                85                  90                  95

Ala Val Tyr Tyr Cys Val Arg Gly Tyr Tyr Ala Phe His Ile Trp
            100                 105                 110

Gly Gln Gly Thr Met Val Thr Val Ser Ser Gly Ser Gly Gly Gly Gly
        115                 120                 125

Ser Ser Ser Glu Leu Thr Gln Asp Pro Ala Val Ser Val Ala Leu Gly
    130                 135                 140

Gln Thr Val Arg Ile Thr Cys Gln Gly Asp Ser Leu Arg Thr Tyr Tyr
145                 150                 155                 160

Ala Ser Trp Tyr Gln Gln Lys Pro Gly Gln Ala Pro Val Leu Val Ala
                165                 170                 175

Ala Gly Lys Asn Asn Arg Pro Ser Gly Ile Pro Asp Arg Phe Ser Ala
            180                 185                 190

Ser Ser Ser Gly Asn Thr Ala Ser Leu Thr Ile Thr Gly Ala Gln Ala
        195                 200                 205

Glu Asp Glu Ala Asp Tyr Tyr Cys Ser Ser Arg Asp Ser Ser Arg Ser
    210                 215                 220

His His Leu Leu Phe Gly Gly Gly Thr Lys Val Thr Val Leu
225                 230                 235
```

<210> SEQ ID NO 14
<211> LENGTH: 122
<212> TYPE: PRT
<213> ORGANISM: Artificial sequence
<220> FEATURE:
<223> OTHER INFORMATION: Synthetic sequence

<400> SEQUENCE: 14

```
Met Ala Gln Val Gln Leu Val Gln Ser Gly Ala Glu Val Lys Lys Pro
1               5                   10                  15

Gly Glu Ser Leu Lys Ile Ser Cys Lys Gly Ser Gly Tyr Ser Phe Thr
            20                  25                  30

Ser Tyr Trp Ile Gly Trp Val Arg Gln Met Pro Gly Lys Gly Leu Glu
        35                  40                  45

Trp Met Gly Ile Ile Tyr Pro Gly Asp Ser Asp Thr Arg Tyr Ser Pro
    50                  55                  60

Ser Phe Gln Gly Gln Val Thr Ile Ser Ala Asp Lys Ser Ile Ser Thr
65                  70                  75                  80
```

Ala Tyr Leu Gln Trp Arg Ser Leu Lys Ala Ser Asp Thr Ala Met Tyr
                85                  90                  95

Tyr Cys Ala Arg Gln Gly Ala Ser Ser Thr Ser Tyr Asp Tyr Trp Gly
            100                 105                 110

Gln Gly Pro Arg Ser Pro Ser Pro Gln Ser
        115                 120

<210> SEQ ID NO 15
<211> LENGTH: 108
<212> TYPE: PRT
<213> ORGANISM: Artificial sequence
<220> FEATURE:
<223> OTHER INFORMATION: Synthetic sequence

<400> SEQUENCE: 15

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Val
                85                  90                  95

Ala Phe Gly Gln Gly Thr Lys Val Glu Ile Lys Arg
            100                 105

<210> SEQ ID NO 16
<211> LENGTH: 115
<212> TYPE: PRT
<213> ORGANISM: Artificial sequence
<220> FEATURE:
<223> OTHER INFORMATION: Synthetic sequence

<400> SEQUENCE: 16

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
    50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Leu Val Thr
            100                 105                 110

Val Ser Ser
        115

<210> SEQ ID NO 17
<211> LENGTH: 115
<212> TYPE: PRT

<213> ORGANISM: Artificial sequence
<220> FEATURE:
<223> OTHER INFORMATION: Synthetic sequence

<400> SEQUENCE: 17

```
Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
                20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ser Asp Lys His Gln Gly Ser Gly Val
50                  55                  60

Pro Ser Arg Phe Ser Gly Ser Lys Ala Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Ala Ile Trp His Ser Ser Ala Trp Val Phe Gly Gly Gly Thr Gln Leu
            100                 105                 110

Thr Val Leu
        115
```

<210> SEQ ID NO 18
<211> LENGTH: 115
<212> TYPE: PRT
<213> ORGANISM: Artificial sequence
<220> FEATURE:
<223> OTHER INFORMATION: Synthetic sequence

<400> SEQUENCE: 18

```
Met Ala Gln Val Gln Leu Val Gln Ser Gly Ala Ala Leu Val Gln Pro
1               5                   10                  15

Gly Gly Ser Leu Arg Leu Ser Cys Ala Ala Ser Gly Phe Ile Phe Ser
                20                  25                  30

Arg Tyr Asn Met Asn Trp Val Arg Gln Ala Pro Gly Lys Arg Pro Glu
            35                  40                  45

Trp Ile Ser Phe Ile Asn Thr Asp Gly Ser Val Ile His Tyr Ala Asp
50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Leu Val Thr
            100                 105                 110

Val Ser Ser
        115
```

<210> SEQ ID NO 19
<211> LENGTH: 115
<212> TYPE: PRT
<213> ORGANISM: Artificial sequence
<220> FEATURE:
<223> OTHER INFORMATION: Synthetic sequence

<400> SEQUENCE: 19

```
Gln Ala Val Leu Thr Gln Pro Ser Ser Leu Ser Ala Ser Pro Gly Ala
1               5                   10                  15

Ser Val Ser Leu Thr Cys Thr Leu Arg Ser Gly Ile Asn Val Gly Ala
                20                  25                  30
```

```
Tyr Arg Val Tyr Trp Tyr Gln Gln Lys Pro Gly Ser Pro Gln Phe
         35                  40                  45

Leu Leu Arg Tyr Lys Thr Asp Ser Asp Lys Gln Gln Gly Ser Gly Val
 50                  55                  60

Ser Ser Arg Phe Ser Gly Ser Arg Asp Ala Ser Ala Asn Ala Gly Ile
 65                  70                  75                  80

Leu Leu Ile Ser Gly Leu Arg Ser Glu Asp Glu Ala Asp Tyr Tyr Cys
                 85                  90                  95

Ala Ile Trp His Ser Ser Ala Trp Val Phe Gly Gly Gly Thr Gln Leu
                100                 105                 110

Thr Val Leu
        115

<210> SEQ ID NO 20
<211> LENGTH: 115
<212> TYPE: PRT
<213> ORGANISM: Artificial sequence
<220> FEATURE:
<223> OTHER INFORMATION: Synthetic sequence

<400> SEQUENCE: 20

Met Ala Gln Val Gln Leu Gln Glu Ser Gly Ala Ala Leu Val Gln Pro
 1               5                  10                  15

Gly Gly Ser Leu Arg Leu Ser Cys Ala Ala Ser Gly Phe Ile Phe Ser
                 20                  25                  30

Arg Tyr Asn Met Asn Trp Val Arg Gln Ala Pro Gly Lys Arg Pro Glu
         35                  40                  45

Trp Ile Ser Phe Ile Asn Thr Asp Gly Ser Val Ile His Tyr Ala Asp
 50                  55                  60

Ser Val Glu Gly Arg Phe Ser Val Ser Arg Asp Asn Val Asn Asn Ser
 65                  70                  75                  80

Leu Tyr Leu Gln Met Asn Asp Leu Arg Asp Asp Thr Ala Val Tyr
                 85                  90                  95

Tyr Cys Val Arg Gln Met Leu Phe Trp Gly Gln Gly Thr Thr Val Thr
                100                 105                 110

Val Ser Ser
        115

<210> SEQ ID NO 21
<211> LENGTH: 115
<212> TYPE: PRT
<213> ORGANISM: Artificial sequence
<220> FEATURE:
<223> OTHER INFORMATION: Synthetic sequence

<400> SEQUENCE: 21

Gln Ala Val Leu Thr Gln Pro Ser Ser Leu Ser Ala Ser Pro Gly Ala
 1               5                  10                  15

Ser Val Ser Leu Thr Cys Thr Leu Arg Ser Gly Ile Asn Val Gly Ala
                 20                  25                  30

Tyr Arg Ile Tyr Trp Tyr Gln Gln Lys Pro Gly Ser Pro Pro Gln Phe
         35                  40                  45

Leu Leu Arg Tyr Lys Ser Asp Ser Asp Lys Gln Gln Gly Ser Gly Val
 50                  55                  60

Pro Ser Arg Phe Ser Gly Ser Arg Asp Ala Ser Ala Asn Ala Gly Ile
 65                  70                  75                  80

Leu Leu Ile Ser Gly Leu Arg Ser Glu Asp Glu Ala Asp Tyr Tyr Cys
```

```
                85                  90                  95

Ala Ile Trp His Ser Ser Ala Trp Val Phe Gly Gly Thr Gln Leu
            100                 105                 110

Thr Val Leu
        115

<210> SEQ ID NO 22
<211> LENGTH: 115
<212> TYPE: PRT
<213> ORGANISM: Artificial sequence
<220> FEATURE:
<223> OTHER INFORMATION: Synthetic sequence

<400> SEQUENCE: 22

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Thr Val Thr
            100                 105                 110

Val Ser Ser
        115

<210> SEQ ID NO 23
<211> LENGTH: 115
<212> TYPE: PRT
<213> ORGANISM: Artificial sequence
<220> FEATURE:
<223> OTHER INFORMATION: Synthetic sequence

<400> SEQUENCE: 23

Gln Ala Val Leu Thr Gln Pro Ser Ser Leu Ser Ala Ser Pro Gly Ala
1               5                   10                  15

Ser Val Ser Leu Thr Cys Thr Leu Arg Ser Gly Ile Asn Val Gly Ala
            20                  25                  30

Tyr Arg Val Tyr Trp Tyr Gln Gln Lys Pro Gly Ser Pro Pro Gln Phe
        35                  40                  45

Leu Leu Arg Tyr Lys Thr Asp Ser Asp Lys Gln Gly Ser Gly Val
50                  55                  60

Pro Ser Arg Phe Ser Gly Ser Arg Asp Ala Ser Ala Asn Ala Gly Ile
65                  70                  75                  80

Leu Leu Ile Ser Gly Leu Arg Ser Glu Asp Glu Ala Asp Tyr Tyr Cys
                85                  90                  95

Ala Ile Trp His Ser Ser Ala Trp Val Phe Gly Gly Gly Thr Lys Leu
            100                 105                 110

Thr Val Leu
        115

<210> SEQ ID NO 24
<211> LENGTH: 115
```

```
<212> TYPE: PRT
<213> ORGANISM: Artificial sequence
<220> FEATURE:
<223> OTHER INFORMATION: Synthetic sequence

<400> SEQUENCE: 24

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
    50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Leu Val Thr
                100                 105                 110

Val Ser Ser
        115

<210> SEQ ID NO 25
<211> LENGTH: 115
<212> TYPE: PRT
<213> ORGANISM: Artificial sequence
<220> FEATURE:
<223> OTHER INFORMATION: Synthetic sequence

<400> SEQUENCE: 25

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Arg Asp Ala Ser Ala Asn Ala Gly Ile
65                  70                  75                  80

Leu Leu Ile Ser Gly Leu Arg Ser Glu Asp Glu Ala Asp Tyr Tyr Cys
                85                  90                  95

Ala Ile Trp His Ser Ser Ala Trp Val Phe Gly Gly Gly Thr Lys Leu
                100                 105                 110

Thr Val Leu
        115

<210> SEQ ID NO 26
<211> LENGTH: 115
<212> TYPE: PRT
<213> ORGANISM: Artificial sequence
<220> FEATURE:
<223> OTHER INFORMATION: Synthetic sequence

<400> SEQUENCE: 26

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
```

```
                    20                  25                  30

Arg Tyr Asn Met Asn Trp Val Arg Gln Ala Pro Gly Lys Arg Pro Glu
            35                  40                  45

Trp Ile Ser Phe Ile Asn Thr Asp Gly Ser Val Ile His Tyr Ala Asp
 50                  55                  60

Ser Val Glu Gly Arg Phe Thr Val Ser Arg Asp Asn Val Asn Asn Ser
 65                  70                  75                  80

Leu Tyr Leu Gln Met Asn Asp Leu Arg Asp Asp Thr Ala Val Tyr
                    85                  90                  95

Tyr Cys Val Arg Gln Met Leu Phe Trp Gly Gln Gly Thr Leu Val Thr
                100                 105                 110

Val Ser Ser
        115

<210> SEQ ID NO 27
<211> LENGTH: 115
<212> TYPE: PRT
<213> ORGANISM: Artificial sequence
<220> FEATURE:
<223> OTHER INFORMATION: Synthetic sequence

<400> SEQUENCE: 27

Gln Ala Val Leu Thr Gln Pro Ser Ser Leu Ser Ala Ser Pro Gly Ala
 1               5                  10                  15

Ser Ala Ser Leu Thr Cys Thr Leu Arg Ser Gly Ile Asn Val Gly Thr
                20                  25                  30

Tyr Arg Ile Tyr Trp Tyr Gln Gln Lys Pro Gly Ser Pro Gln Tyr
            35                  40                  45

Leu Leu Arg Tyr Lys Ser Asp Ser Asp Lys Gln Gln Gly Ser Gly Val
 50                  55                  60

Pro Ser Arg Phe Ser Gly Ser Arg Asp Ala Ser Ala Asn Ala Gly Ile
 65                  70                  75                  80

Leu Leu Ile Ser Gly Leu Arg Ser Glu Asp Glu Ala Asp Tyr Tyr Cys
                85                  90                  95

Ala Ile Trp His Ser Ser Ala Cys Val Phe Gly Gly Gly Thr Lys Leu
                100                 105                 110

Thr Val Leu
        115

<210> SEQ ID NO 28
<211> LENGTH: 115
<212> TYPE: PRT
<213> ORGANISM: Artificial sequence
<220> FEATURE:
<223> OTHER INFORMATION: Synthetic sequence

<400> SEQUENCE: 28

Met Ala Gln Val Gln Leu Gln Glu Ser Gly Ala Ala Leu Val Gln Pro
 1               5                  10                  15

Gly Gly Ser Leu Arg Leu Ser Cys Ala Ala Ser Gly Phe Ile Phe Ser
                20                  25                  30

Arg Tyr Asn Met Asn Trp Val Arg Gln Ala Pro Gly Lys Arg Pro Glu
            35                  40                  45

Trp Ile Ser Phe Ile Asn Thr Asp Gly Ser Val Ile His Tyr Ala Asp
 50                  55                  60

Ser Val Glu Gly Arg Phe Ser Val Ser Arg Asp Asn Val Asn Asn Ser
 65                  70                  75                  80
```

```
Leu Tyr Leu Gln Met Asn Asp Leu Arg Asp Asp Thr Ala Val Tyr
                 85                  90                  95

Tyr Cys Ala Arg Gln Leu Leu Tyr Trp Gly Gln Gly Thr Val Val Thr
            100                 105                 110

Val Ser Ser
        115

<210> SEQ ID NO 29
<211> LENGTH: 115
<212> TYPE: PRT
<213> ORGANISM: Artificial sequence
<220> FEATURE:
<223> OTHER INFORMATION: Synthetic sequence

<400> SEQUENCE: 29

Gln Ala Val Leu Thr Gln Pro Ser Ser Leu Ser Ala Ser Pro Gly Ala
1               5                   10                  15

Ser Val Ser Leu Thr Cys Thr Leu Arg Ser Gly Ile Asn Val Gly Ala
            20                  25                  30

Tyr Arg Ile Tyr Trp Tyr Gln Gln Lys Pro Gly Ser Pro Pro Gln Phe
        35                  40                  45

Leu Leu Arg Tyr Lys Ser Gly Ser Asp Lys His Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Arg Ser Glu Asp Glu Ala Asp Tyr Tyr Cys
                85                  90                  95

Ala Ile Trp His Ser Ser Ala Trp Val Phe Gly Gly Gly Thr Gln Leu
            100                 105                 110

Thr Val Leu
        115

<210> SEQ ID NO 30
<211> LENGTH: 122
<212> TYPE: PRT
<213> ORGANISM: Artificial sequence
<220> FEATURE:
<223> OTHER INFORMATION: Synthetic sequence

<400> SEQUENCE: 30

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Val Asp Asn Ser Val Ser Thr Thr Tyr
65                  70                  75                  80

Leu Gln Leu Asn Asn Leu Gln Ala Ser Asp Thr Ala Met Tyr Tyr Cys
                85                  90                  95

Ala Thr Arg Val Leu Pro Ala Gly His Phe Tyr Thr Leu Asp Val Trp
            100                 105                 110

Gly Gln Gly Thr Leu Val Thr Val Ser Ser
        115                 120

<210> SEQ ID NO 31
```

<211> LENGTH: 108
<212> TYPE: PRT
<213> ORGANISM: Artificial sequence
<220> FEATURE:
<223> OTHER INFORMATION: Synthetic sequence

<400> SEQUENCE: 31

Ser Tyr Val Leu Thr Gln Pro Pro Ser Val Ser Val Ala Pro Gly Glu
1               5                   10                  15

Thr Ala Ile Leu Thr Cys Val Gly Asn Asn Ile Gly Asp Lys Phe Val
            20                  25                  30

His Trp Tyr Gln Gln Lys Pro Gly Gln Ala Pro Val Leu Val Met Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Gly Glu Tyr Tyr Cys Gln Val Trp Asp Asn Ser Ser Asn Gln
                85                  90                  95

Gly Val Phe Gly Gly Gly Thr Gln Leu Thr Val Leu
            100                 105

<210> SEQ ID NO 32
<211> LENGTH: 122
<212> TYPE: PRT
<213> ORGANISM: Artificial sequence
<220> FEATURE:
<223> OTHER INFORMATION: Synthetic sequence

<400> SEQUENCE: 32

Met Ala Gln Val Gln Leu Gln Gln Ser Gly Pro Gly Leu Val Lys Pro
1               5                   10                  15

Ser Gln Thr Leu Ser Leu Thr Cys Val Ile Ser Gly Asp Ser Val Ser
            20                  25                  30

Asp Asn Ser Gly Ala Trp Asn Trp Ile Arg Gln Ser Pro Ser Arg Gly
        35                  40                  45

Leu Glu Trp Leu Gly Arg Thr Tyr Tyr Arg Ser Lys Trp Tyr Thr Asp
    50                  55                  60

Tyr Ala Asp Ser Val Lys Ser Arg Ile Thr Ile Ile Pro Asp Ile Pro
65                  70                  75                  80

Lys Asn Gln Phe Ser Leu His Leu Asn Ser Val Thr Pro Glu Asp Thr
                85                  90                  95

Ala Val Tyr Tyr Cys Val Arg Gly Tyr Tyr Tyr Ala Phe His Ile Trp
            100                 105                 110

Gly Gln Gly Thr Met Val Thr Val Ser Ser
        115                 120

<210> SEQ ID NO 33
<211> LENGTH: 108
<212> TYPE: PRT
<213> ORGANISM: Artificial sequence
<220> FEATURE:
<223> OTHER INFORMATION: Synthetic sequence

<400> SEQUENCE: 33

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Tyr Tyr Tyr Ala
            20                  25                  30

```
Ser Trp Tyr Gln Gln Lys Pro Gly Gln Ala Pro Leu Leu Val Ile Tyr
        35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Gly Ser Gly Asn Asn
                 85                  90                  95

Val Val Phe Gly Gly Gly Thr Lys Leu Thr Val Leu
            100                 105

<210> SEQ ID NO 34
<211> LENGTH: 120
<212> TYPE: PRT
<213> ORGANISM: Artificial sequence
<220> FEATURE:
<223> OTHER INFORMATION: Synthetic sequence

<400> SEQUENCE: 34

Met Ala Gln Val Gln Leu Val Gln Ser Gly Ser Glu Leu Lys Lys Pro
 1               5                  10                  15

Gly Ala Ser Val Lys Val Ser Cys Lys Ala Ser Gly Tyr Thr Phe Thr
                20                  25                  30

Ser Tyr Ala Met Asn Trp Val Arg Gln Ala Pro Gly Gln Gly Leu Glu
            35                  40                  45

Trp Met Gly Trp Ile Asn Thr Asn Thr Gly Asn Pro Thr Tyr Ala Gln
 50                  55                  60

Gly Phe Thr Gly Arg Phe Val Phe Ser Leu Asp Thr Ser Val Ser Thr
 65                  70                  75                  80

Ala Tyr Leu Gln Ile Ser Ser Leu Lys Ala Glu Asp Thr Ala Val Tyr
                 85                  90                  95

Tyr Cys Ala Ser Arg Leu Ala Ala Ala Gly Phe Asp Tyr Trp Gly Gln
                100                 105                 110

Gly Thr Leu Val Thr Val Ser Ser
            115                 120

<210> SEQ ID NO 35
<211> LENGTH: 115
<212> TYPE: PRT
<213> ORGANISM: Artificial sequence
<220> FEATURE:
<223> OTHER INFORMATION: Synthetic sequence

<400> SEQUENCE: 35

Gln Ala Val Leu Thr Gln Pro Ser Ser Leu Ser Ala Ser Pro Gly Ala
 1               5                  10                  15

Ser Ala Ser Leu Thr Cys Thr Leu Arg Ser Gly Ile Asn Val Gly Thr
                20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ser Asp Lys Gln Gln Gly Ser Gly Val
 50                  55                  60

Pro Ser Arg Phe Ser Gly Ser Lys Asp Ala Ser Ala Asn Ala Gly Ile
 65                  70                  75                  80

Leu Leu Ile Ser Gly Leu Arg Ser Glu Asp Glu Ala Asp Tyr Tyr Cys
                 85                  90                  95

Ala Ile Trp His Ser Ser Ala Trp Val Phe Gly Gly Gly Thr Gln Leu
                100                 105                 110
```

Thr Val Leu
       115

<210> SEQ ID NO 36
<211> LENGTH: 115
<212> TYPE: PRT
<213> ORGANISM: Artificial sequence
<220> FEATURE:
<223> OTHER INFORMATION: Synthetic sequence

<400> SEQUENCE: 36

Met Ala Gln Val Gln Leu Val Glu Ser Gly Ala Ala Leu Val Gln Pro
1               5                   10                  15

Gly Gly Ser Leu Arg Leu Ser Cys Ala Ala Ser Gly Phe Ile Phe Ser
            20                  25                  30

Arg Tyr Asn Met Asn Trp Val Arg Gln Ala Pro Gly Lys Arg Pro Glu
        35                  40                  45

Trp Ile Ser Phe Ile Asn Thr Asp Gly Ser Val Ile His Tyr Ala Asp
    50                  55                  60

Ser Val Glu Gly Arg Phe Thr Val Ser Arg Asp Asn Val Asn Asn Ser
65                  70                  75                  80

Leu Tyr Leu Gln Met Asn Asp Leu Arg Asp Asp Thr Ala Val Tyr
                85                  90                  95

Tyr Cys Val Arg Gln Met Leu Phe Trp Gly Gln Gly Thr Leu Val Thr
            100                 105                 110

Val Ser Ser
       115

<210> SEQ ID NO 37
<211> LENGTH: 115
<212> TYPE: PRT
<213> ORGANISM: Artificial sequence
<220> FEATURE:
<223> OTHER INFORMATION: Synthetic sequence

<400> SEQUENCE: 37

Gln Ala Val Leu Thr Gln Pro Ser Ser Leu Ser Ala Ser Pro Gly Ala
1               5                   10                  15

Ser Val Ser Leu Thr Cys Thr Leu Arg Ser Gly Ile Asn Val Gly Ala
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Arg Ser Glu Asp Glu Ala Asp Tyr Tyr Cys
                85                  90                  95

Ala Ile Trp His Ser Ser Ala Trp Val Phe Gly Gly Gly Thr Lys Leu
            100                 105                 110

Thr Val Leu
       115

<210> SEQ ID NO 38
<211> LENGTH: 122
<212> TYPE: PRT
<213> ORGANISM: Artificial sequence
<220> FEATURE:
<223> OTHER INFORMATION: Synthetic sequence

<400> SEQUENCE: 38

Met Ala Gln Val Gln Leu Gln Gln Ser Gly Pro Gly Leu Val Lys Pro
1               5                   10                  15

Ser Gln Thr Leu Ser Leu Thr Cys Val Ile Ser Gly Asp Ser Val Ser
            20                  25                  30

Asp Asn Ser Gly Ala Trp Asn Trp Ile Arg Gln Ser Pro Ser Arg Gly
        35                  40                  45

Leu Glu Trp Leu Gly Arg Thr Tyr Tyr Arg Ser Lys Trp Tyr Thr Asp
    50                  55                  60

Tyr Ala Asp Ser Val Lys Ser Arg Ile Thr Ile Ile Pro Asp Ile Pro
65                  70                  75                  80

Lys Asn Gln Phe Ser Leu His Leu Asn Ser Val Thr Pro Glu Asp Thr
                85                  90                  95

Ala Val Tyr Tyr Cys Val Arg Gly Tyr Tyr Ala Phe His Ile Trp
            100                 105                 110

Gly Gln Gly Thr Met Val Thr Val Ser Ser
        115                 120

<210> SEQ ID NO 39
<211> LENGTH: 109
<212> TYPE: PRT
<213> ORGANISM: Artificial sequence
<220> FEATURE:
<223> OTHER INFORMATION: Synthetic sequence

<400> SEQUENCE: 39

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ala Ala
        35                  40                  45

Gly Lys Asn Asn Arg Pro Ser Gly Ile Pro Asp Arg Phe Ser Ala Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Arg Ser His
                85                  90                  95

His Leu Leu Phe Gly Gly Gly Thr Lys Val Thr Val Leu
            100                 105

<210> SEQ ID NO 40
<211> LENGTH: 14
<212> TYPE: PRT
<213> ORGANISM: Artificial sequence
<220> FEATURE:
<223> OTHER INFORMATION: Synthetic sequence

<400> SEQUENCE: 40

Gly Gly Gly Ser Gly Gly Gly Ser Gly Gly Gly Ser
1               5                   10

<210> SEQ ID NO 41
<211> LENGTH: 7
<212> TYPE: PRT
<213> ORGANISM: Artificial sequence
<220> FEATURE:
<223> OTHER INFORMATION: Synthetic sequence

```
<400> SEQUENCE: 41

Gly Gly Gly Gly Gly Gly Ser
1               5

<210> SEQ ID NO 42
<211> LENGTH: 5
<212> TYPE: PRT
<213> ORGANISM: Artificial sequence
<220> FEATURE:
<223> OTHER INFORMATION: Synthetic sequence

<400> SEQUENCE: 42

Gly Gly Gly Gly Ser
1               5

<210> SEQ ID NO 43
<211> LENGTH: 6
<212> TYPE: PRT
<213> ORGANISM: Artificial sequence
<220> FEATURE:
<223> OTHER INFORMATION: Synthetic sequence

<400> SEQUENCE: 43

Gly Gly Gly Gly Gly Ser
1               5

<210> SEQ ID NO 44
<211> LENGTH: 7
<212> TYPE: PRT
<213> ORGANISM: Artificial sequence
<220> FEATURE:
<223> OTHER INFORMATION: Synthetic sequence

<400> SEQUENCE: 44

Gly Ser Gly Gly Gly Gly Ser
1               5

<210> SEQ ID NO 45
<211> LENGTH: 15
<212> TYPE: PRT
<213> ORGANISM: Artificial sequence
<220> FEATURE:
<223> OTHER INFORMATION: Synthetic sequence

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 8
<212> TYPE: PRT
<213> ORGANISM: Artificial sequence
<220> FEATURE:
<223> OTHER INFORMATION: Synthetic sequence

<400> SEQUENCE: 46

Gly Tyr Ser Phe Thr Ser Tyr Trp
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic sequence

<400> SEQUENCE: 47
```

```
Ile Tyr Pro Gly Asp Ser Asp Thr
1               5
```

<210> SEQ ID NO 48
<211> LENGTH: 12
<212> TYPE: PRT
<213> ORGANISM: Artificial sequence
<220> FEATURE:
<223> OTHER INFORMATION: Synthetic sequence

<400> SEQUENCE: 48

```
Ala Arg Gln Gly Ala Ser Ser Thr Ser Tyr Asp Tyr
1               5                   10
```

<210> SEQ ID NO 49
<211> LENGTH: 6
<212> TYPE: PRT
<213> ORGANISM: Artificial sequence
<220> FEATURE:
<223> OTHER INFORMATION: Synthetic sequence

<400> SEQUENCE: 49

```
Gln Ser Ile Ser Ser Tyr
1               5
```

<210> SEQ ID NO 50
<211> LENGTH: 9
<212> TYPE: PRT
<213> ORGANISM: Artificial sequence
<220> FEATURE:
<223> OTHER INFORMATION: Synthetic sequence

<400> SEQUENCE: 50

```
Gln Gln Ala Asn Ser Phe Pro Val Ala
1               5
```

<210> SEQ ID NO 51
<211> LENGTH: 8
<212> TYPE: PRT
<213> ORGANISM: Artificial sequence
<220> FEATURE:
<223> OTHER INFORMATION: Synthetic sequence

<400> SEQUENCE: 51

```
Gly Phe Ile Phe Ser Arg Tyr Asn
1               5
```

<210> SEQ ID NO 52
<211> LENGTH: 8
<212> TYPE: PRT
<213> ORGANISM: Artificial sequence
<220> FEATURE:
<223> OTHER INFORMATION: Synthetic sequence

<400> SEQUENCE: 52

```
Ile Asn Thr Asp Gly Ser Val Ile
1               5
```

<210> SEQ ID NO 53
<211> LENGTH: 6
<212> TYPE: PRT
<213> ORGANISM: Artificial sequence
<220> FEATURE:
<223> OTHER INFORMATION: Synthetic sequence

<400> SEQUENCE: 53

```
Val Arg Gln Met Leu Phe
1               5

<210> SEQ ID NO 54
<211> LENGTH: 9
<212> TYPE: PRT
<213> ORGANISM: Artificial sequence
<220> FEATURE:
<223> OTHER INFORMATION: Synthetic sequence

<400> SEQUENCE: 54

Ser Gly Ile Asn Val Gly Thr Tyr Arg
1               5

<210> SEQ ID NO 55
<211> LENGTH: 7
<212> TYPE: PRT
<213> ORGANISM: Artificial sequence
<220> FEATURE:
<223> OTHER INFORMATION: Synthetic sequence

<400> SEQUENCE: 55

Tyr Lys Ser Asp Ser Asp Lys
1               5

<210> SEQ ID NO 56
<211> LENGTH: 9
<212> TYPE: PRT
<213> ORGANISM: Artificial sequence
<220> FEATURE:
<223> OTHER INFORMATION: Synthetic sequence

<400> SEQUENCE: 56

Ala Ile Trp His Ser Ser Ala Trp Val
1               5

<210> SEQ ID NO 57
<211> LENGTH: 9
<212> TYPE: PRT
<213> ORGANISM: Artificial sequence
<220> FEATURE:
<223> OTHER INFORMATION: Synthetic sequence

<400> SEQUENCE: 57

Ser Gly Ile Asn Val Gly Ala Tyr Arg
1               5

<210> SEQ ID NO 58
<211> LENGTH: 7
<212> TYPE: PRT
<213> ORGANISM: Artificial sequence
<220> FEATURE:
<223> OTHER INFORMATION: Synthetic sequence

<400> SEQUENCE: 58

Tyr Lys Thr Asp Ser Asp Lys
1               5

<210> SEQ ID NO 59
<211> LENGTH: 9
<212> TYPE: PRT
<213> ORGANISM: Artificial sequence
<220> FEATURE:
<223> OTHER INFORMATION: Synthetic sequence

<400> SEQUENCE: 59

Ala Ile Trp His Ser Ser Ala Cys Val
```

```
1               5

<210> SEQ ID NO 60
<211> LENGTH: 6
<212> TYPE: PRT
<213> ORGANISM: Artificial sequence
<220> FEATURE:
<223> OTHER INFORMATION: Synthetic sequence

<400> SEQUENCE: 60

Ala Arg Gln Leu Leu Tyr
1               5

<210> SEQ ID NO 61
<211> LENGTH: 7
<212> TYPE: PRT
<213> ORGANISM: Artificial sequence
<220> FEATURE:
<223> OTHER INFORMATION: Synthetic sequence

<400> SEQUENCE: 61

Tyr Lys Ser Gly Ser Asp Lys
1               5

<210> SEQ ID NO 62
<211> LENGTH: 15
<212> TYPE: PRT
<213> ORGANISM: Artificial sequence
<220> FEATURE:
<223> OTHER INFORMATION: Synthetic sequence

<400> SEQUENCE: 62

Ala Thr Arg Val Leu Pro Ala Gly His Phe Tyr Thr Leu Asp Val
1               5                   10                  15

<210> SEQ ID NO 63
<211> LENGTH: 6
<212> TYPE: PRT
<213> ORGANISM: Artificial sequence
<220> FEATURE:
<223> OTHER INFORMATION: Synthetic sequence

<400> SEQUENCE: 63

Asn Ile Gly Asp Lys Phe
1               5

<210> SEQ ID NO 64
<211> LENGTH: 11
<212> TYPE: PRT
<213> ORGANISM: Artificial sequence
<220> FEATURE:
<223> OTHER INFORMATION: Synthetic sequence

<400> SEQUENCE: 64

Gln Val Trp Asp Asn Ser Ser Asn Gln Gly Val
1               5                   10

<210> SEQ ID NO 65
<211> LENGTH: 9
<212> TYPE: PRT
<213> ORGANISM: Artificial sequence
<220> FEATURE:
<223> OTHER INFORMATION: Synthetic sequence

<400> SEQUENCE: 65

Val Ser Asp Asn Ser Gly Ala Trp Asn
1               5
```

<210> SEQ ID NO 66
<211> LENGTH: 7
<212> TYPE: PRT
<213> ORGANISM: Artificial sequence
<220> FEATURE:
<223> OTHER INFORMATION: Synthetic sequence

<400> SEQUENCE: 66

Tyr Arg Ser Lys Trp Tyr Thr
1               5

<210> SEQ ID NO 67
<211> LENGTH: 10
<212> TYPE: PRT
<213> ORGANISM: ARTIFICIAL SEQUENCE
<220> FEATURE:
<223> OTHER INFORMATION: Synthetic sequence

<400> SEQUENCE: 67

Val Arg Gly Tyr Tyr Tyr Ala Phe His Ile
1               5                   10

<210> SEQ ID NO 68
<211> LENGTH: 6
<212> TYPE: PRT
<213> ORGANISM: Artificial sequence
<220> FEATURE:
<223> OTHER INFORMATION: Synthetic sequence

<400> SEQUENCE: 68

Ser Leu Arg Thr Tyr Tyr
1               5

<210> SEQ ID NO 69
<211> LENGTH: 11
<212> TYPE: PRT
<213> ORGANISM: Artificial sequence
<220> FEATURE:
<223> OTHER INFORMATION: Synthetic sequence

<400> SEQUENCE: 69

Asn Ser Arg Asp Gly Ser Gly Asn Asn Val Val
1               5                   10

<210> SEQ ID NO 70
<211> LENGTH: 8
<212> TYPE: PRT
<213> ORGANISM: Artificial sequence
<220> FEATURE:
<223> OTHER INFORMATION: Synthetic sequence

<400> SEQUENCE: 70

Gly Tyr Thr Phe Thr Ser Tyr Ala
1               5

<210> SEQ ID NO 71
<211> LENGTH: 8
<212> TYPE: PRT
<213> ORGANISM: Artificial sequence
<220> FEATURE:
<223> OTHER INFORMATION: Synthetic sequence

<400> SEQUENCE: 71

Ile Asn Thr Asn Thr Gly Asn Pro
1               5

<210> SEQ ID NO 72
<211> LENGTH: 11
<212> TYPE: PRT
<213> ORGANISM: Artificial sequence
<220> FEATURE:
<223> OTHER INFORMATION: Synthetic sequence

<400> SEQUENCE: 72

Ala Ser Arg Leu Ala Ala Ala Gly Phe Asp Tyr
1               5                   10

<210> SEQ ID NO 73
<211> LENGTH: 12
<212> TYPE: PRT
<213> ORGANISM: Artificial sequence
<220> FEATURE:
<223> OTHER INFORMATION: Synthetic sequence

<400> SEQUENCE: 73

Ser Ser Arg Asp Ser Ser Arg Ser His His Leu Leu
1               5                   10

<210> SEQ ID NO 74
<211> LENGTH: 478
<212> TYPE: PRT
<213> ORGANISM: Artificial sequence
<220> FEATURE:
<223> OTHER INFORMATION: Synthetic sequence

<400> SEQUENCE: 74

Met Ala Gln Val Gln Leu Gln Gln Ser Gly Pro Gly Leu Val Lys Pro
1               5                   10                  15

Ser Gln Thr Leu Ser Leu Thr Cys Val Ile Ser Gly Asp Ser Val Ser
                20                  25                  30

Asp Asn Ser Gly Ala Trp Asn Trp Ile Arg Gln Ser Pro Ser Arg Gly
            35                  40                  45

Leu Glu Trp Leu Gly Arg Thr Tyr Tyr Arg Ser Lys Trp Tyr Thr Asp
        50                  55                  60

Tyr Ala Asp Ser Val Lys Ser Arg Ile Thr Ile Ile Pro Asp Ile Pro
65                  70                  75                  80

Lys Asn Gln Phe Ser Leu His Leu Asn Ser Val Thr Pro Glu Asp Thr
                85                  90                  95

Ala Val Tyr Tyr Cys Val Arg Gly Tyr Tyr Ala Phe His Ile Trp
            100                 105                 110

Gly Gln Gly Thr Met Val Thr Val Ser Ser Gly Ser Gly Gly Gly Gly
        115                 120                 125

Ser Ser Ser Glu Leu Thr Gln Asp Pro Ala Val Ser Val Ala Leu Gly
130                 135                 140

Gln Thr Val Arg Ile Thr Cys Gln Gly Asp Ser Leu Arg Thr Tyr Tyr
145                 150                 155                 160

Ala Ser Trp Tyr Gln Gln Lys Pro Gly Gln Ala Pro Val Leu Val Ala
                165                 170                 175

Ala Gly Lys Asn Asn Arg Pro Ser Gly Ile Pro Asp Arg Phe Ser Ala
            180                 185                 190

Ser Ser Ser Gly Asn Thr Ala Ser Leu Thr Ile Thr Gly Ala Gln Ala
        195                 200                 205

Glu Asp Glu Ala Asp Tyr Tyr Cys Ser Ser Arg Asp Ser Ser Arg Ser
    210                 215                 220

His His Leu Leu Phe Gly Gly Gly Thr Lys Val Thr Val Leu Gly Gly

```
                225                 230                 235                 240
Leu Gly Gly Leu Ala Ser Glu Pro Lys Ser Cys Asp Lys Thr His Thr
                245                 250                 255
Cys Pro Pro Cys Pro Ala Pro Glu Leu Leu Gly Gly Pro Ser Val Phe
                260                 265                 270
Leu Phe Pro Pro Lys Pro Lys Asp Thr Leu Met Ile Ser Arg Thr Pro
                275                 280                 285
Glu Val Thr Cys Val Val Val Asp Val Ser His Glu Asp Pro Glu Val
                290                 295                 300
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
                325                 330                 335
Leu Thr Val Leu His Gln Asp Trp Leu Asn Gly Lys Glu Tyr Lys Cys
                340                 345                 350
Lys Val Ser Asn Lys Ala Leu Pro Ala Pro Ile Glu Lys Thr Ile Ser
                355                 360                 365
Lys Ala Lys Gly Gln Pro Arg Glu Pro Gln Val Tyr Thr Leu Pro Pro
                370                 375                 380
Ser Arg Asp Glu Leu Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Asp Ser Asp
                420                 425                 430
Gly Ser Phe Phe Leu Thr Ser Lys Leu Thr Val Asp Lys Ser Arg Trp
                435                 440                 445
Gln Gln Gly Asn Val Phe Ser Cys Ser Val Met His Glu Ala Leu His
                450                 455                 460
Asn His Tyr Thr Gln Lys Ser Leu Ser Leu Ser Pro Gly Lys
465                 470                 475

<210> SEQ ID NO 75
<211> LENGTH: 451
<212> TYPE: PRT
<213> ORGANISM: Artificial sequence
<220> FEATURE:
<223> OTHER INFORMATION: Synthetic sequence

<400> SEQUENCE: 75

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
                20                  25                  30
Ala Met His Trp Val Arg Gln Ala Pro Gly Lys Gly Leu Glu Trp Val
                35                  40                  45
Ser Ala Ile Thr Trp Asn Ser Gly His Ile Asp Tyr Ala Asp Ser Val
                50                  55                  60
Glu Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Val Ser Tyr Leu Ser Thr Ala Ser Ser Leu Asp Tyr Trp Gly
                100                 105                 110
Gln Gly Thr Leu Val Thr Val Ser Ser Ala Ser Thr Lys Gly Pro Ser
```

-continued

```
            115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Tyr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450
```